US011498968B2

(12) United States Patent
Cannarile et al.

(10) Patent No.: US 11,498,968 B2
(45) Date of Patent: Nov. 15, 2022

(54) TREATMENT OF TUMORS WITH AN ANTI-CSF-1R ANTIBODY IN COMBINATION WITH AN ANTI-PD-L1 ANTIBODY AFTER FAILURE OF ANTI-PD-L1/PD1 TREATMENT

(71) Applicant: Hoffmann-La Roche Inc., Little Falls, NJ (US)

(72) Inventors: Michael Cannarile, Penzberg (DE); Anna-Maria Jegg, Penzberg (DE); Francesca Michielin, Basel (CH); Carola Ries, Penzberg (DE); Dominik Ruettinger, Penzberg (DE); Martin Weisser, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 197 days.

(21) Appl. No.: 16/438,256

(22) Filed: Jun. 11, 2019

(65) Prior Publication Data

US 2019/0309078 A1 Oct. 10, 2019

Related U.S. Application Data

(63) Continuation of application No. PCT/EP2017/083696, filed on Dec. 20, 2017.

(30) Foreign Application Priority Data

Dec. 22, 2016 (EP) .................... 16206066

(51) Int. Cl.
*A61K 39/00* (2006.01)
*C07K 16/28* (2006.01)
*A61P 35/00* (2006.01)

(52) U.S. Cl.
CPC .......... *C07K 16/2866* (2013.01); *A61P 35/00* (2018.01); *C07K 16/2827* (2013.01); *A61K 2039/505* (2013.01); *A61K 2039/507* (2013.01); *A61K 2039/545* (2013.01); *C07K 2317/24* (2013.01); *C07K 2317/56* (2013.01); *C07K 2317/76* (2013.01); *C07K 2317/92* (2013.01)

(58) Field of Classification Search
CPC ............................... A61K 2039/505
See application file for complete search history.

(56) References Cited

U.S. PATENT DOCUMENTS

| 5,202,238 A | 4/1993 | Fell et al. |
| 5,204,244 A | 4/1993 | Fell et al. |
| 5,208,020 A | 5/1993 | Chari et al. |
| 5,416,064 A | 5/1995 | Chari et al. |
| 5,635,483 A | 6/1997 | Pettit et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | Mcgahren et al. |
| 5,770,710 A | 6/1998 | Mcgahren et al. |
| 5,773,001 A | 6/1998 | Hamann et al. |
| 5,780,588 A | 7/1998 | Pettit et al. |
| 5,798,229 A | 8/1998 | Strittmatter et al. |
| 5,866,114 A | 2/1999 | Pandit et al. |
| 5,877,296 A | 3/1999 | Hamann et al. |
| 5,961,974 A | 10/1999 | Armitage et al. |
| 5,981,724 A | 11/1999 | Armitage et al. |
| 6,184,354 B1 | 2/2001 | Koths et al. |
| 6,391,637 B1 | 5/2002 | Armitage et al. |
| 6,410,711 B1 | 6/2002 | Armitage et al. |
| 6,630,579 B2 | 10/2003 | Chari et al. |
| 6,946,129 B1 | 9/2005 | Siegall et al. |
| 7,108,852 B2 | 9/2006 | Devalaraja et al. |
| 7,223,741 B2 | 5/2007 | Krieg |
| 7,288,251 B2 | 10/2007 | Bedian et al. |
| 7,338,660 B2 | 3/2008 | Bedian et al. |
| 7,498,298 B2 | 3/2009 | Doronina et al. |
| 8,182,813 B2 | 5/2012 | Brasel et al. |
| 8,217,149 B2 | 7/2012 | Irving et al. |
| 8,263,079 B2 * | 9/2012 | Doody ............. A61K 39/39541 424/143.1 |
| 8,303,955 B2 | 11/2012 | Presta et al. |
| 8,470,977 B2 | 6/2013 | Haegel et al. |
| 8,604,170 B2 | 12/2013 | Haegel et al. |
| 8,993,614 B2 | 3/2015 | Bartkovitz et al. |
| 8,999,327 B2 | 4/2015 | Dimoudis et al. |
| 9,169,323 B2 | 10/2015 | Fertig et al. |
| 9,192,667 B2 | 11/2015 | Hoves et al. |
| 9,221,910 B2 | 12/2015 | Fertig et al. |

(Continued)

FOREIGN PATENT DOCUMENTS

| CN | 101636412 A | 1/2010 |
| CN | 102791738 A | 11/2012 |
| CN | 110636861 A | 12/2019 |
| EP | 0307434 A1 | 3/1989 |
| EP | 0425235 B1 | 9/1996 |
| EP | 0668914 B1 | 8/2000 |
| EP | 1476185 A2 | 11/2004 |
| EP | 2423228 A1 | 2/2012 |
| EP | 2510010 A1 | 10/2012 |
| JP | H0967400 A | 3/1997 |
| JP | 2001523956 A | 11/2001 |
| JP | 2006519163 A | 8/2006 |
| JP | 2008013566 A | 1/2008 |
| JP | 2010512421 A | 4/2010 |
| JP | 2010536378 A | 12/2010 |

(Continued)

OTHER PUBLICATIONS

ClinicalTrials.gov Identifier: NCT02323191 (posted Dec. 23, 2014) (pp. 1-10).*

(Continued)

Primary Examiner — Stephen L Rawlings
(74) Attorney, Agent, or Firm — Morrison & Foerster LLP

(57) ABSTRACT

The current invention relates to the combination therapy of an anti-CSF-1R antibody (especially a CSF-1R dimerization inhibitor) in combination with an anti-PD-L1 antibody after PD1/PD-L1 inhibitor treatment failure, corresponding pharmaceutical compositions or medicaments using such combination therapy.

12 Claims, 4 Drawing Sheets

Specification includes a Sequence Listing.

(56) References Cited

U.S. PATENT DOCUMENTS

| | | |
|---|---|---|
| 9,499,624 B2 | 11/2016 | Dimoudis et al. |
| 9,499,625 B2 | 11/2016 | Dimoudis et al. |
| 9,499,626 B2 | 11/2016 | Dimoudis et al. |
| 9,617,342 B2 | 4/2017 | Fertig et al. |
| 9,624,302 B2 | 4/2017 | Fertig et al. |
| 9,663,580 B2 | 5/2017 | Dimoudis et al. |
| 9,879,085 B2 | 1/2018 | Dimoudis et al. |
| 9,988,458 B2 | 6/2018 | Fertig et al. |
| 10,023,643 B2 | 7/2018 | Fertig et al. |
| 10,030,073 B2 | 7/2018 | Fertig et al. |
| 10,072,087 B2 | 9/2018 | Dimoudis et al. |
| 10,077,314 B1 | 9/2018 | Dimoudis et al. |
| 10,287,358 B2 | 5/2019 | Dimoudis et al. |
| 10,336,830 B2 | 7/2019 | Fertig et al. |
| 2002/0141994 A1 | 10/2002 | Devalaraja et al. |
| 2003/0211100 A1 | 11/2003 | Bedian et al. |
| 2004/0006006 A9 | 1/2004 | Armitage et al. |
| 2007/0122378 A1 | 5/2007 | Freeman et al. |
| 2007/0280935 A1 | 12/2007 | Bohrmann et al. |
| 2009/0155164 A1 | 6/2009 | Brasel et al. |
| 2009/0304687 A1 | 12/2009 | Drachman |
| 2009/0317403 A1 | 12/2009 | Aharinejad |
| 2010/0040614 A1 | 2/2010 | Ahmed et al. |
| 2010/0203056 A1 | 8/2010 | Irving et al. |
| 2011/0081353 A1 | 4/2011 | Haegel et al. |
| 2011/0165156 A1 | 7/2011 | Dimoudis et al. |
| 2011/0178278 A1 | 7/2011 | Haegel et al. |
| 2011/0274683 A1 | 11/2011 | Wong et al. |
| 2012/0251531 A1 | 10/2012 | Baehner et al. |
| 2012/0329997 A1 | 12/2012 | Fertig et al. |
| 2013/0005949 A1 | 1/2013 | Fertig et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0289250 A1 | 10/2013 | Haegel et al. |
| 2013/0302322 A1 | 11/2013 | Wong et al. |
| 2014/0057972 A1 | 2/2014 | Haegel et al. |
| 2014/0065135 A1 | 3/2014 | Irving et al. |
| 2014/0079699 A1 | 3/2014 | Wong et al. |
| 2014/0079706 A1 | 3/2014 | Cannarile et al. |
| 2014/0120088 A1 | 5/2014 | Carpentier et al. |
| 2014/0205608 A1 | 7/2014 | Steidi et al. |
| 2014/0255417 A1 | 9/2014 | Haegel et al. |
| 2014/0314771 A1 | 10/2014 | Hoves et al. |
| 2014/0336363 A1 | 11/2014 | Fertig et al. |
| 2014/0341902 A1 | 11/2014 | Maecker et al. |
| 2015/0073129 A1 | 3/2015 | Herting et al. |
| 2015/0080556 A1 | 3/2015 | Fertig et al. |
| 2015/0158950 A1 | 6/2015 | Dimoudis et al. |
| 2015/0175696 A1 | 6/2015 | Fertig et al. |
| 2015/0274830 A1 | 10/2015 | Dimoudis et al. |
| 2015/0274831 A1 | 10/2015 | Dimoudis et al. |
| 2015/0322153 A1 | 11/2015 | Irving et al. |
| 2016/0053015 A1 | 2/2016 | Fertig et al. |
| 2016/0220669 A1 | 8/2016 | Hoves et al. |
| 2017/0015752 A1 | 1/2017 | Fertig et al. |
| 2017/0029517 A1 | 2/2017 | Dimoudis et al. |
| 2017/0051065 A1 | 2/2017 | Herting et al. |
| 2017/0114139 A1 | 4/2017 | Fertig et al. |
| 2017/0247459 A1 | 8/2017 | Cannarile et al. |
| 2017/0275368 A1 | 9/2017 | Fertig et al. |
| 2017/0320953 A1 | 11/2017 | Dimoudis et al. |
| 2018/0186883 A1* | 7/2018 | Papadopoulos .... C07K 16/2827 |
| 2018/0208662 A1 | 7/2018 | Dimoudis et al. |
| 2018/0244788 A1 | 8/2018 | Dimoudis et al. |
| 2018/0346581 A1 | 12/2018 | Herting et al. |
| 2018/0346582 A1 | 12/2018 | Fertig et al. |
| 2019/0071507 A1 | 3/2019 | Dimoudis et al. |
| 2019/0185572 A1 | 6/2019 | Cannarile et al. |
| 2019/0218296 A1* | 7/2019 | Bjorck ............... C07K 16/2827 |
| 2019/0284284 A1* | 9/2019 | Hoves .................... A61P 37/02 |
| 2019/0300614 A1 | 10/2019 | Dimoudis et al. |
| 2020/0392234 A1 | 12/2020 | Herting et al. |
| 2021/0205453 A1 | 7/2021 | Ravuri et al. |

FOREIGN PATENT DOCUMENTS

| | | | |
|---|---|---|---|
| JP | 2011512851 A | 4/2011 | |
| JP | 2013513367 A | 4/2013 | |
| JP | 2015516369 A | 6/2015 | |
| JP | 2016516798 A | 6/2016 | |
| JP | 2016531150 A | 10/2016 | |
| KR | 20080079301 A | 8/2008 | |
| RU | 94028282 A | 7/1996 | |
| RU | 2008132150 A | 2/2010 | |
| RU | 2434641 C2 | 11/2011 | |
| RU | 2010141584 A | 4/2012 | |
| RU | 2478400 C2 | 4/2013 | |
| WO | WO198807089 A1 | 9/1988 | |
| WO | 199325687 A1 | 12/1993 | |
| WO | 199411026 A2 | 5/1994 | |
| WO | 199411026 A3 | 8/1994 | |
| WO | 199818810 A1 | 5/1998 | |
| WO | 199843089 A1 | 10/1998 | |
| WO | 199852976 A1 | 11/1998 | |
| WO | 199917798 A1 | 4/1999 | |
| WO | 200107055 A1 | 2/2001 | |
| WO | WO2001030381 A2 | 5/2001 | |
| WO | WO2001030381 A3 | 5/2001 | |
| WO | 2003040170 A2 | 5/2003 | |
| WO | 2003040170 A3 | 10/2003 | |
| WO | WO2004045532 A2 | 6/2004 | |
| WO | WO2005046657 A2 | 5/2005 | |
| WO | WO2005046657 A3 | 11/2005 | |
| WO | WO2004045532 A3 | 1/2006 | |
| WO | 2006012451 A2 | 2/2006 | |
| WO | 2006012451 A3 | 3/2006 | |
| WO | WO2006096489 A2 | 9/2006 | |
| WO | 2006133396 A2 | 12/2006 | |
| WO | WO2006096489 A3 | 3/2007 | |
| WO | 2007075326 A2 | 7/2007 | |
| WO | 2007081879 A2 | 7/2007 | |
| WO | 2006133396 A3 | 8/2007 | |
| WO | 2007081879 A3 | 9/2007 | |
| WO | 2008073959 A2 | 6/2008 | |
| WO | 2008083174 A2 | 7/2008 | |
| WO | 2007075326 A3 | 9/2008 | |
| WO | 2008119493 A1 | 10/2008 | |
| WO | 2008073959 A3 | 11/2008 | |
| WO | 2008083174 A3 | 12/2008 | |
| WO | 2008153926 A2 | 12/2008 | |
| WO | WO2009026303 A1 | 2/2009 | |
| WO | 2008153926 A3 | 3/2009 | |
| WO | 2008153926 A4 | 5/2009 | |
| WO | 2009120903 A2 | 10/2009 | |
| WO | WO2009112245 A9 | 11/2009 | |
| WO | 2009120903 A3 | 1/2010 | |
| WO | WO2010077634 A1 | 7/2010 | |
| WO | 2010088395 A2 | 8/2010 | |
| WO | 2010088395 A3 | 11/2010 | |
| WO | 2011066389 A1 | 6/2011 | |
| WO | WO2011070024 A1 | 6/2011 | |
| WO | 2011107553 A1 | 9/2011 | |
| WO | 2011117329 A1 | 9/2011 | |
| WO | 2011131407 A1 | 10/2011 | |
| WO | WO2011123381 A1 | 10/2011 | |
| WO | 2011140249 A2 | 11/2011 | |
| WO | 2012068470 A2 | 5/2012 | |
| WO | 2012085291 A1 | 6/2012 | |
| WO | 2012110360 A1 | 8/2012 | |
| WO | 2013011021 A1 | 1/2013 | |
| WO | 2013019906 A1 | 2/2013 | |
| WO | 2013057281 A2 | 4/2013 | |
| WO | 2013057281 A3 | 6/2013 | |
| WO | 2013079174 A1 | 6/2013 | |
| WO | 2013087699 A1 | 6/2013 | |
| WO | 2011140249 A3 | 8/2013 | |
| WO | 2013119716 A1 | 8/2013 | |
| WO | 2012068470 A3 | 9/2013 | |
| WO | 2013135648 A1 | 9/2013 | |
| WO | WO-2013132044 A1 * | 9/2013 | ............. A61P 35/00 |
| WO | 2013169264 A1 | 11/2013 | |
| WO | 2014072441 A1 | 5/2014 | |
| WO | 2014173814 A1 | 10/2014 | |

(56) References Cited

FOREIGN PATENT DOCUMENTS

| WO | WO2015036511 | A1 | 3/2015 | |
|---|---|---|---|---|
| WO | 2016023960 | A1 | 2/2016 | |
| WO | 2016069727 | A1 | 5/2016 | |
| WO | 2016081384 | A1 | 5/2016 | |
| WO | 2016109310 | A1 | 7/2016 | |
| WO | 2016196935 | A1 | 12/2016 | |
| WO | 2018036852 | A1 | 3/2018 | |
| WO | WO-2018115051 | A1 * | 6/2018 | ............. A61P 35/00 |
| WO | 2018160917 | A1 | 9/2018 | |
| WO | 2016/011160 | | 1/2021 | |

OTHER PUBLICATIONS

Bonelli et al. (FEBS J. Feb. 2018; 285 (4): 777-87).*
Hu-Lieskovan et al. (Ann. Oncol. Nov. 1, 2015; 26 (Suppl. 8): viii5-viii14, Abstract #18TiP); p. 1).*
Ries et al. (Cancer Cell. 2014; 25: 846-59).*
Laoui et al. (Front Immunol. Oct. 7, 2014; 5: 489; pp. 1-15).*
Mitchem et al. (Cancer Res. Feb. 1, 2013; 73 (3): 1128-4).*
Haegel et al. (mAbs. 2013; 5 (5): 736-47).*
Kim et al. (Proc. Natl. Acad. Sci. USA. 2014; 111: 11774-9).*
Zhu et al. (Cancer Res. Sep. 15, 2014; 74 (18): 5057-69).*
Guo et al. (J. Transl. Med. Jul. 29, 2015; 13: 247; pp. 1-13).*
Magiera-Mularz et al. (iScience. 2021; 24: 101960; pp. 1-26).*
Dhupkar et al. (Cancer Med. Jun. 2018; 7 (6): 2654-64).*
Chin et al. (Chang Gung Med J. Jan.-Feb. 2008; 31 (1): 1-15).*
Jiang et al. (J. Biol. Chem. Feb. 11, 2005; 280 (6): 4656-4662).*
Riemer et al. (Mol. Immunol. 2005; 42: 1121-1124).*
Stanley et al. (Cold Spring Harb. Perspect. Biol. Jun. 2014; 6 (6): a021857; pp. 1-21).*
Ingram et al. (Proc. Natl. Acad. Sci. USA. Apr. 10, 2018; 115 (15): 3912-3917).*
Kipps et al. (J. Exp. Med. Jan. 1, 1985; 161 (1): 1-17).*
Zhang et al. (Cell. Apr. 16, 2020; 181 (2): 442-59).*
Swierczak et al. (Cancer Immunol. Res. Aug. 2014; 2 (8): 765-76).*
Callahan et al. (J. Leukoc. Biol. 2013; 94: 41-53).*
Brodská et al. (Cancer Immunol. Res. Oct. 2016; 4 (10): 815-819).*
Nielsen et al. (Cell. Immunol. Jun. 2005; 235 (2):109-16).*
Su et al. (Biochem. Genet. Jun. 2014; 52 (5-6): 310-9).*
Fares et al. (Am. Soc. Clin. Oncol. Educ. Book. Jan. 2019; 39: 147-164).*
Ruffell et al. (Cancer Cell. Apr. 13, 2015; 27 (4): 462-72).*
Columbus (OncLive®; published Feb. 18, 2020; https://www.onclive.com/view/nivolumabcabiralizumab-combo-misses-pfs-endpoint-in-pancreatic-cancer; pp. 1-3).*
ClinicalTrials.gov Identifier: NCT03336216 (posted Nov. 8, 2017) (pp. 1-9).*
Abu-Duhier, F.M. et al. (2003). "Mutational Analysis of Class III Receptor Tyrosine Kinases (C-KIT, C-FMS, FLT3) in Idiopathic Myelofibrosis," Br. J. Haematol. 120(3):464-470.
Anonymous (2016). "NCT02452424: A Combination Clinical Study of PLX3397 and Pembrolizumab to Treat Advanced Melanoma and Other Solid Tumors," pp. 1-7.
Anonymous. (2016). "NCT023231911 A Study of Emactuzumab (RO5509554) and (MPDL3280A) Administered in Combination in Patients With Advanced Solid Tumors," pp. 1-5. MPDL3280A Administered in Combination in Patients With Advanced Solid Tumors, pp. 1-5.
Ashmun, R.A. et al. (1989). "Monoclonal Antibodies to the Human CSF-1 Receptor (c-fms Proto-Oncogene Product) Detect Epitopes on Normal Mononuclear Phagocytes and on Human Myeloid Leukemic Blast Cells," Blood 73 (3):827-837.
Ausubel, F. et al. (1987). Current Protocols in Molecular Biology, Greene Publishing and Wiley Interscience, New York, TOC, 7 pages.
Baker, A.H. et al. (1993). "Expression of the Colony-Stimulating Factor 1 Receptor in B Lymphocytes," Oncogene 8 (2):371-378.
Balkwill, F. (2006). "TNF-α in Promotion and Progression of Cancer," Cancer Metastasis Rev. 25:409-416.
Balkwill, F. et al. (2005). "Smoldering and Polarized Inflammation in the Initiation and Promotion of Malignant Disease," Cancer Cell 7(3):211-217.
Barnes, L.M. et al. (2000). "Advances in Animal Cell Recombinant Protein Production: GS-NS0 Expression System," Cytotechnology 32:109-123.
Barnes, L.M. et al. (2001). "Characterization of the Stability of Recombinant Protein Production in the GS-NS0 Expression System," Biotech. Bioeng. 73:261-270.
Bingle, L. et al. (2002). "The Role of Tumour-Associated Macrophages in Tumour Progression: Implications for Nev Anticancer Therapies," J. Pathol. 196(3):254-265.
Boackle, R.J. et al. (1979). "An IgG Primary Sequence Exposure Theory for Complement Activation Using Synthetic Peptides," Nature 282:742-743.
Boettler, T. et al. (2006). "Expression of the Interleukin-7 Receptor Alpha Chain (CD127) on Virus-Specific CD8+ T Dells Identifies Functionally and Phenotypically Defined Memory T Cells during Acute Resolving Hepatitis B Virus Infection," J. Virol. 80(7):3532-3540.
Bourette, R.P. et al. (2000). "Early Events in M-CSF Receptor Signaling," Growth Factors 17(3):155-166.
Bretscher, P. et al. (1970). "A Theory of Self-Nonself Discrimination," Science 169:1042-1049.
Bretscher, P.A. (1999). "A Two-Step, Two-Signal Model for the Primary Activation of Precursor Helper T Cells," Proc. Natl. Acad. Sci. USA 96:185-190.
Brunhouse, R. et al. (1979). "Isotypes of IgG: Comparison of the Primary Structure of Three Pairs of Isotypes which Differ in Their Ability to Activate Complement," J. Mol. Immunol. 16:907-917.
Burton, D.R. et al. (1980). "The C1q Receptor Site on Immunoglobulin," Nature 288:338-344.
Butte, M.J. et al. (2007). "Programmed Death-1 Ligand 1 Interacts Specifically with the B7-1 Costimulatory Molecule to Inhibit T Cell Responses," Immunity 27:111-122, 22 pages.
Campbell, I.K. et al. (2000). "The Colony-Stimulating Factors and Collagen-Induced Arthritis: Exacerbation of Disease by M-CSF and G-CSF and Requirement for Endogenous M-CSF," J. Leukoc. Biol. 68:144-150.
Carter, L. et al. (2002). "PD-1: PD-L Inhibitory Pathway Affects Both CD4(+) and CD8(+) T Cells and is Overcome by IL-2," Eur. J. Immunol. 32(3):634-643.
Carter, P. et al. (1992). "Humanization of an Anti-p185HER2 Antibody for Human Cancer Therapy," Proc. Natl. Acad. Sci. USA 89:4285-4289.
Cenci, S. et al. (2000). "M-CSF Neutralization and Egr-1 Deficiency Prevent Ovariectomy-Induced Bone Loss," J. Clin. Invest. 105(9):1279-1287.
Chase, A. et al. (2009, e-pub. Oct. 30, 2008). "Imatinib Sensitivity as a Consequence of a CSF1R-Y571D Mutation and CSF1/CSF1R Signaling Abnormalities in the Cell Line GDM1," Leukemia 23(2):358-364.
Choueiri, M.B. et al. (2006). "The Central Role of Osteoblasts in the Metastasis of Prostate Cancer," Cancer Metastasis Rev. 25:601-609.
Coussens, L, et al. (1986). "Structural Alteration of Viral Homologue of Receptor Proto-Oncogene fms at Carboxyl Terminus," Nature 320(60659):277-280.
Da Costa, C.E. et al. (2005). "Presence of Osteoclast-Like Multinucleated Giant Cells in the Bone and Nonostotic Lesions of Langerhans Cell Histiocytosis," J. Exp. Med. 201(5):687-693.
Dai, X.-M. et al. (2002). "Targeted Disruption of the Mouse Colony-Stimulating Factor 1 Receptor Gene Results in Osteopetrosis, Mononuclear Phagocyte Deficiency, Increased Primitive Progenitor Cell Frequencies, and Reproductive Defects," Blood 99(1):111-120.
Daroszewska, A. et al. (2006). "Mechanisms of Disease: Genetics of Paget's Disease of Bone and Related Disorders," Nat. Clin. Pract. Rheumatol. 2(5):270-277.
Denardo, D.G. et al. (2011). "Leukocyte Complexity Predicts Breast Cancer Survival and Functionally Regulates Response to Chemotherapy," Cancer Discovery 1:54-67, 30 pages.
Denardo, D.G. et al. (2009) "CD4+ T Cells Regulate Pulmonary Metastasis of Mammary Carcinomas by Enhancing Protumor Properties of Macrophages," Cancer Cell 16(2):91-102, 24 pages.

(56) References Cited

OTHER PUBLICATIONS

Dong, H. et al. (1999). "B7-H1, A Third Member of the B7 Family, Co-Stimulates T-Cell Proliferation and Interieukin-10 Secretion," Nature Med. 5(12):1365-1369.

Drees, P. et al. (2007). "Mechanisms of Disease: Molecular Insights Into Aseptic Loosening of Orthopedic Implants," Nat. Clin. Pract. Rheumatol. 3(3):165-171.

Durocher, Y. et al. (2002). "High-level and High-Throughput Recombinant Protein Production by Transient Transfection of Suspension-Growing Human 293-EBNA1 Cells," Nucl. Acids. Res. 30(2):e9:1-9.

Eppihimer, M.J. et al. (2002). "Expression and Regulation of the PD-L1 Immunoinhibitory Molecule on Microvascular Endothelial Cells," Microcirculation 9(2):133-145, 20 pages.

Espinosa, I. et al. (2009). "Coordinate Expression of Colony-Stimulating Factor-1 and Colony-Stimulating Factor-1-Related Proteins is Associated with Poor Prognosis in Gynecological and Nongynecological Leiomyosarcoma," Am. J. Pathol. 174(6):2347-2356.

Feldstein, A.C. et al. (2005). "Practice Patterns in Patients at Risk for Glucocorticoid-Induced Osteoporosis," Osteoporos. Int. 16:2168-2174.

Freeman, G.J. et al. (2000, e-pub. Oct. 2, 2000). "Engagement of the PD-1 Immunoinhibitory Receptor by a Novel B7 Family Member Leads to Negative Regulation of Lymphocyte Activation," J. Exp. Med. 192:1027-1034.

Geisse, S. et al. (1996). "Eukaryotic Expression Systems: A Comparison," Protein Expr. Purif. 8(3):271-282.

Guzman-Clark, J.R. et al. (2007). "Barriers in the Management of Glucocorticoid-Induced Osteoporosis," Arthritis Rheum. 57(1):140-146.

Guzman-Montes, G.Y. et al. (2009). "Indirect Patient Expenses for Antituberculosis Treatment in Tijuana, Mexico: is Trealment Really Free?" Clin. Cancer Res. 3(10):778-787.

Hao, A.-J. et al. (2002). "Expression of Macrophage Colony-Stimulating Factor and Its Receptor in Microglia Activation is Linked to Teratogen-Induced Neuronal Damage," Neuroscience 112(4):889-900.

Heckman, K.L. et al. (2007). "Fast-Tracked CTL: Rapid Induction of Potent Anti-Tumor Killer T Cells in situ," Eur. J. Immunol. 37:1827-1835.

Hezareh et al. (2001). "Effector function activities of a panel of mutants of a broadly neutralizing antibody against human immunodeficiency virus type 1" J. Virol. 75(24):12161-12168.

Hoves, S. et al. (2006). "Monocyte-Derived Human Macrophages Mediate Anergy in Allogeneic T Cells and Induce Regulatory T Cells," J. Immunol. 177:2691-2698.

Hume, D.A. et al. (2012). "Therapeutic Applications of Macrophage Colony-Stimulating Factor-1 (CSF-1) and Antagonists of CSF-1 Receptor (CSF-1R) Signaling," Blood 119(8):1810-1820.

Idusogie, E.E. et al. (2000). "Mapping of the C1q Binding Site on Rituxan, a Chimeric Antibody With a Human IgG1 Fc," J. Immunol. 164;4178-4184.

Ikonomidis, I. et al. (2005). "Increased Circulating C-Reactive Protein and Macrophage-Colony Stimulating Factor are Complementary Predictors of Long-Term Outcome in Patients With Chronic Coronary Artery Disease," Eur. Heart. J. 26:1618-1624.

Inaba, T. et al. (1992). "Expression of M-CSF Receptor Encoded by c-fms on Smooth Muscle Cells Derived from Arteriosclerotic Lesion," J. Biol. Chem. 267(8):5693-5699.

International Preliminary Report on Patentability, dated Jun. 25, 2019, for PCT Application No. PCT/EP2017/083696, filed Dec. 20, 2017.

International Search Report and Written Opinion, dated Feb. 19, 2018, for PCT Application No. PCT/EP2017/083696, filed Dec. 20, 2017.

Jenkins, M.K. et al. (1987). "Antigen Presentation y Chemically Modified Splenocytes Induces Antigen-Specific T Cell Unresponsiveness in vitro and in vivo," J. Exp. Med. 165:302-319.

Johnson, G. et al. (2000). "Kabat Database and Its Applications: 30 Years After the First Variability Plot," Nucleic Acids Res. 28:214-218.

Kabat, E.A. et al. (1991). Sequences of Proteins of Immunological Interest, 5th ed., Public Health Service, National Institutes of Health, Bethesda, MD. TOC, 21 pages.

Kacinski, B.M. (1997). "CSF-1 and Its Receptor in Breast Carcinomas and Neoplasms of the Female Reproductive Tract," Mol. Reprod. Dev. 46:71-74.

Kaku, M. et al. (2003). "Amyloid β Protein Deposition and Neuron Loss in Osteopetrotic (op/op) Mice," Brain Res. Brain Res. Protoc. 12:104-108.

Kaufman, R.J. (2000). "Overview of Vector Design for Mammalian Gene Expression," Mol. Biotechnol. 16:151-161.

Kawai, T. et al. (2010, e-pub. Apr. 20, 2010). "The Role of Pattern-Recognition Receptors in Innate Immunity: Update on Toll-Like Receptors," Nature Immunol. 11(5):373-384.

Kawamura, K. et al. (2009). "Detection of M2 Macrophages and Colony-Stimulating Factor 1 Expression in Serous and Mucinous Ovarian Epithelial Tumors," Pathol. Int. 59(5):300-305.

Keir, M.E. et al. (2008, e-pub. Jan. 2, 2008). "PD-1 and Its Ligands in Tolerance and Immunity," Annu. Rev. Immunol. 26:677-704.

Kirma, N. et al. (2007). "Elevated Expression of the Oncogene c-fms and Its Ligand, the Macrophage Colony-Stimulating Factor-1, in Cervical Cancer and the Role of Transforming Growth Factor-B1 in Inducing c-fms Expression," Cancer Res 67(5):1918-1926.

Kitaura, H. et al. (2008). "An Anti-c-Fms antibody Inhibits Orthodontic Tooth Movement," J. Dental Research 87 (4):396-400.

Kitaura, H. et al. (2005). "M-CSF Mediates TNF-lnduced Inflammatory Osteolysis," J. Clin. Invest. 115 (12):3418-3427.

Kuipers, H. et al. (2006). "Contribution of the PD-1 Ligands/PD-1 Signaling Pathway to Dendritic Cell-Mediated CD4+ T Cell Activation," Eur. J. Immunol. 36(9):2472-2482.

Lafferty, K.J. et al. (1975) "A New Analysis of Allogeneic Interactions," Aust. J. Exp. Biol. Med. Sci. 53(pt. 1);27-42.

Latchman, Y. et al. (2001). "PD-L2 is a Second Ligand for PD-1 and Inhibits T Cell Activation," Nature Immunol. 2(3):261-268.

Latchman, Y.E. et al. (2004). "PD-L1-Deficient Mice Show That PD-L1 on T Cells, Antigen-Presenting Cells, and Host Tissues Negatively Regulates T Cells," Proc. Natl. Acad. Sci. USA 101(29):10691-10696.

Lee, P.S.W. et al. (1999). "The Cbl Protooncoprotein Stimulates CSF-1 Receptor Multiubiquitination and Endocytosis, and Attenuates Macrophage Proliferation," EMBO J. 18(13):3616-3628.

Lee, S.J. et al. (2006, e-pub. Jan. 9, 2006). "Interferon Regulatory Factor-1 is Prerequisite to the Constitutive Expression and IFN-γ-Induced Upregulation of B7-H1 (CD274)," FEBS Lett. 580(3)755-762.

Lenda, D.M. et al. (2003). "Reduced Macrophage Recruitment, Proliferation, and Activation in Colony-Stimulating Factor-1-Deficient Mice Results in Decreased Tubular Apoptosis During Renal Inflammation," J. Immunol. 170:3254-3262.

Lenschow, D.J. et al. (1996). "CD28/B7 System of T Cell Costimulation," Ann. Rev. Immunol. 14:233-258.

Lester, J.E. et al. (2006, e-pub. Nov. 29, 2005). "Current management of Treatment-Induced Bone Loss in Women With Breast Cancer Treated in the United Kingdom," Br. J. Cancer 94:30-35.

Li, W. et al. (1991). "Role of Dimerization and Modification of the CSF-1 Receptor in Its Activation and Internalization During the CSF-1 Response," EMBO Journal. 10(2):277-288.

Liang, S.C. et al. (2003). "Regulation of PD-1, PD-L1, and PD-L2 Expression During Normal and Autoimmune Responses," Eur. J. Immunol. 33(10): 2706-2716.

Lin, H et al. (2008). "Discovery of a Cytokine and Its Receptor by Functional Screening of the Extracellular Proteome," Science 320(5877):807-811.

Liu, J. et al. (2007). "Plasma Cells From Multiple Myeloma Patients Express B7-H1 (PD-L1) and Increase Expression After Stimulation With IFN-γ and TLR Ligands Via A MyD88-, TRAF6-, and MEK-Dependent Pathway," Blood 110(1):296-304.

Loke, P. et al. (2003). "PD-L1 and PD-L2 are Differentially Regulated by Th1 and Th2 Cells," Proc. Natl Acad. Sci. USA 100(9):5336-5341.

(56) References Cited

OTHER PUBLICATIONS

Lukas, T.J. et al. (1981). "Inhibition of C1-Mediated Immune Hemolysis by Monomeric and Dimeric Peptides From the Second Constant Domain of Human immunoglobulin G," J. Immunol. 127(6):2555-2560.
Makrides, S.C. (1999). "Components of Vectors for Gene Transfer and Expression in Mammalian Cells," Protein Expr. Purif 17(2):183-202.
Mantovani, A et al. (2004, e-pub. May 19, 2004). "Tumour-Associated Macrophages as a Prototypic Type II Polarised Phagocyte Population: Role in Tumour Progression," Eur. J. Cancer 40(11):1660-1667.
Mantovani, A. et al. (2010, e-pub. Feb. 9, 2010). "Macrophages, Innate Immunity and Cancer: Balance, Tolerance, and Diversity," Curr. Opin. Immunol. 22(2):231-237.
Mantovani, A. et al. (2004). "The Chemokine System in Diverse Forms of Macrophage Activation and Polarization," Trends Immunol. 25(12):677-686.
Morgan, A. et al. (1995). "The N-Terminal End of the CH2 Domain of Chimeric Human IgG1 Anti-HLA-DR is Necessary for C1q, FcγRI and FcγRIII Binding," Immunology 86(2):319-324.
Murayama, T. et al. (1999). "Intraperitoneal Administration of Anti-c-fms Monoclonal Antibody Prevents Initial Events of Atherogenesis but Does Not Reduce the Size of Advanced Lesions in Apolipoprotein E-Deficient Mice," Circulation 99:1740-1746.
Murphy, G.M. Jr. et al. (1998). "Macrophage Colony-Stimulating Factor Augments β-Amyloid-induced Interieukin-1, Interieukin-6, and Nitric Oxide Production by Microglial Cells," J. Biol. Chem. 273(33):20967-20971.
Murphy, G.M., Jr et al. (2000). "Expression of Macrophage Colony-Stimulating Factor Receptor is Increased in the AβPV717F Transgenic Mouse Model of Alzheimer's Disease," Am. J. Pathol. 157(3):895-904.
Nielsen, C. et al. (2005. e-pub. Sep. 19, 2005). "Alternative Splice Variants of the Human PD-1 Gene," Cell. Immunol. 235(2):109-116.
Nishimura, H. et al. (2001). "Autoimmune Dilated Cardiomyopathy in PD-1 Receptor-Deficient Mice," Science 291 (5502):319-322.
Nishimura, H. et al. (1999). "Development of Lupus-Like Autoimmune Diseases by Disruption of the PD-1 Gene Encoding an ITIM Motif-Carrying Immunoreceptor," Immunity 11(2):141-151.
Nishimura, H. et al. (1996). "Developmentally Regulated Expression of the PD-1 Protein on the Surface of Double-Negative (CD4-CD8-) Thymocytes," Int. Immunol. 8(5):773-780.
Norderhaug, L. et al. (1997). "Versatile Vectors for Transient and Stable Expression of Recombinant Antibody Molecules in Mammalian Cells," J. Immunol. Methods 204(1):77-87.
Orlandi, R. et al. (1989). "Cloning Immunoglobulin Variable Domains for Expression by the Polymerase Chain Reaction," Proc. Natl. Acad. Sci. USA 86(10):3833-3837.
Orre, M. et al. (1999). "Macrophages and Microvessel Density in Tumors of the Ovary," Gynecol. Oncol. 73 (1):47-50.
Paulus, P. et al. (2006, e-pub. Apr. 17, 2006). "Colony-Stimulating Factor-1 Antibody Reverses Chemoresistance in Human MCF-7 Breast Cancer Xenografts," Cancer Res. 66:4349-4356.
Pixley, F.J. et al. (2004). "CSF-1 Regulation of the Wandering Macrophage: Complexity in Action," Trends Cell Biol. 14(11):628-638.
Pollard, J.W. (1997). "Role of Colony-Stimulating Factor-1 in Reproduction and Development," Mol. Reprod. Dev. 46(1):54-61.
Pollard, J.W. (2004). "Tumour-Educated Macrophages Promote Tumour Progression and Metastasis," Nat. Rev. Cancer 4:71-78.
Price, F. et al. (1993). "Colony-Stimulating Factor-1 in Primary Ascites of Ovarian Cancer is a Significant Predictor of Survival," Am. J. Obstet. Gynecol. 168(2):520-527.
Rabello, D. et al. (2006, e-pub. Jul. 7, 2016). "CSF1 Gene Associated With Aggressive Periodontitis in the Japanese Population," Biochem. Biophys. Res. Commun. 347:791-796.
Ritchlin, C.T. et al. (2003). "Mechanisms of TNF-α- and RANKL-Mediated Osteoclastogenesis and Bone Resorption in Psoriatic Arthritis," J. Clin. Invest. 111(6):821-831.
Roggia, C. et al. (2004). "Role of TNF-α Producing T-Cells in Bone Loss Inducted by Estrogen Deficiency," Minerva Med. 95(2):125-132.
Roth, P. et al. (1992). "The Biology of CSF-1 and Its Receptor," Curr. Top. Microbiol. Immunol. 181:141-167.
Roussel, M.F. et al. (1987). "Transforming Potential of the c-fms Proto-Oncogene (CSF-1 Receptor)," Nature 325 (6104):549-552.
Saitoh, T. et al. (2000). "Clinical Significance of Increased Plasma Concentalion of Macrophage Colony—Stimulating Factor in Patients With Angina Pectoris," J. Am. Coll. Cardiol. 35(3):655-665.
Sawada, M. et al. (1990). "Activation and Proliferation of the Isolated Microglia by Colony Stimulating Factor-1 and Possible Involvement of Protein Kinase C," Brain Res. 509:119-124.
Schlaeger, E.-J. (1996). "The Protein Hydrolysate, Primatone RL, Is a Cost-Effective Multiple Growth Promoter of Mammalian Cell Culture in Serum-Containing and Serum-Free Media and Displays Anti-Apoptosis Properties," J Immunol. Methods 194(2):191-199.
Schlaeger, E.-J. et al. (1999). "Transient Gene Expression in Mammalian Cells Grown in Serum-Free Suspension Culture," Cytotechnology 30(1-3):71-83.
Scholl, S. et al. (1994). "Circulating Levels of Colony-Stimulating Factor 1 as a Prognostic Indicator in 82 Patients With Epithelial Ovarian Cancer," Br. J. Cancer 62:342-346.
Scholl, S.M. et al. (1994). "Anti-Colony-Stimulating Factor-1 Antibody Staining in Primary Breast Adenocarcinomas Correlates With Marked Inflammatory Cell Infiltrates and Prognosis," J. Natl. Cancer Inst. 86(2):120-126.
Schreiner, B. et al. (2004). "Interferon-Beta Enhances Monocyte and Dendritic Cell Expression of B7-H1 (PD-L1), A Strong Inhibitor of Autologous T-Cell Activation: Relevance for the Immune Modulatory Effect in Multiple Sclerosis," J. Neuroimmunol. 155(1-2):172-182.
Sloan-Lancaster et al. (1993) "Induction of T-Cell Anergy by Altered T-Cell-Receptor Ligand on Live Antigen-Presenting Cells," Nature 363:156-159.
Stanley, E.R. et al. (1983). "CSF-1-A Mononuclear Phagocyte Lineage-Specific Hemopoietic Growth Factor," J. Cellular Biochemistry 21(2):151-159.
Stanley, E.R. et al. (1994). "The Biology and Action of Colony Stimulating Factor-1," Stem Cells 12(Suppl. 1):15-24.
Stanley, E.R. et al. (1997). "Biology and Action of Colony-Stimulating Factor-1," Mol. Reprod. Dev. 46(1):14-10.
Stoch, S.A. et al. (2001). "Bone Loss in Men with Prostate Cancer Treated With Gonadotropin-Releasing Hormone Agonists," J. Clin. Endocrinol. Metab. 86(6):2787-2791.
Tanaka, S. et al. (1993). "Macrophage Colony-stimulating Factor is Indispensable for both Proliferation and Differentiation of Osteoclast Progenitors," J. Clin. Invest. 91(1):257-263.
Thommesen, J.E. et al. (2000). "Lysine 322 in the Human IgG3 C(H)2 Domain is Crucial for Antibody Dependent Complement Activation," Mol. Immunol. 37(16):995-1004.
Tseng, S.-Y. et al. (2001). "B7-Dc, A New Dendritic Cell Molecule with Potent Costimulatory Properties for T Cells," J. Exp. Med. 193(7):839-846.
Ueda, H. et al. (2003, e-pub. Apr. 30, 2003). "Association of the T-Cell Regulatory Gene CTLA4 With Susceptibility to Autoimmune Disease," Nature 423(6939):506-511.
Vessella, R.L. et al. (2006) "Targeting Factors Involved in Bone Remodeling as Treatment Strategies in Prostate Cancer Bone Metastasis," Clin. Cancer Res. 12(20 Pt 2):6285s-6290s.
Viola, A. et al. (1996). "T Cell Activation Determined by T Cell Receptor Number and Tunable Thresholds," Science 273:104-106.
Wan, B. et al. (2006). "Aberrant Regulation of Synovial T Cell Activation by Soluble Costimulatory Molecules in Rheumatoid Arthritis," J. Immunol. 177:8844-8850.
Wang, Z., et al. (1993). "Identification of the Ligand-Binding Regions in the Macrophage Colony-Stimulating Factor Receptor Extracellular Domain," Molecular and Cellular Biology 13(9):5348-5359.

(56) References Cited

OTHER PUBLICATIONS

Werner, R.G. et al. (1998). "Appropriate Mammalian Expression Systems for Biopharmaceuticals," Arzneimittelforschung 48:870-880.
West, R.B. et al. (2006). "A Landscape Effect in Tenosynovial Giant-Cell Tumor From Activation of CSF1 Expression by a Translocation in a Minority of Tumor Cells," Proc. Natl. Acad. Sci. USA 103(3):690-695.
Wyckoff, J.B. et al. (2007). "Direct Visualization of Macrophage-Assisted Tumor Cell Intravasation in Mammary Tumors," Cancer Res. 67(6):2649-2656.
Xiong, Y. et al. (2011). "A CSF-1 Receptor Phosphotyrosine 559 Signaling Pathway Regulates Receptor Ubiquitination and Tyrosine Phosphorylation," J. Biol. Chem. 286(2):952-960.
Yamazaki, T. et al. (2002). "Expression of Programmed Death 1 Ligands by Murine T Cells and APC1," J. Immunol. 169:5538-5545.
Yang, D.-H. et al. (2004). "The Relationship Between Point Mutation and Abnormal Expression of c-fms Oncogene in Hepatocellular Carcinoma," Hepatobiliary Pancreat. Dis. Int. 3(1):86-89.
Yeung, Y.-G. et al. (2003). "Proteomic Approaches to the Analysis of Early Events in Colony-stimulating Factor-1 Signal Transduction," Molecular & Cellular Proteomics 2:1143-1155.
Zhong, X. et al. (2007). "PD-L2 Expression Extends Beyond Dendritic Cells/Macrophages to B1 Cells Enriched for VH11/VH12 and Phosphatidylcholine Binding," Eur. J. Immunol. 37(9):2405-2410.
Zins, K. et al. (2007). "Colon Cancer Cell-Derived Tumor Necrosis Factor-α Mediates the Tumor Growth—Promoting Response in Macrophages by Up-regulating the Colony-Stimulating Factor-1 Pathway," Cancer Res. 67(3):1038-1045.
US 9,951,139, 10/2016, Fertig et al. (withdrawn)
US 9,951,140, 10/2016, Fertig et al. (withdrawn)
Affymetrix Ebioscience. (2000-2014). "Anti-Mouse CD115 (c-fms) Purified," located at http://www.ebioscience.com/mouse-cd115-antibody-purified-afs98.htm, last visited on Mar. 26, 2015, 1 page.
Agrawal, S. et al. (2007) "Synthetic Agonists of Toll-Like Receptors 7, 8 and 9," Biochemical Society Transactions 35(Pt. 6):1461-1467.
Aharinejad, S. et al. (2004). "Colony-Stimulating Factor-1 Blockade by Antisense Oligonucleotides and Small Interfering RNAs Suppresses Growth of Human Mammary Tumor Xenografts in Mice," Cancer Res 64(15):5378-5384.
Albert, M.L. et al. (1998). "Dendritic Cells Acquire Antigen From Apoptotic Cells and Induce Class I-Restricted CTLs," Nature 392(6671):86-89.
Alderson, M.R. et al. (1993). "CD40 Expression by Human Monocytes: Regulation by Cytokines and Activation of Monocytes by the Ligand for CD40," J. Exp. Med. 178:669-674.
Altenburg, A. et al. (1999). "CD40 Ligand-CD40 Interaction Induces Chemokines in Cervical Carcinoma Cells in Synergism With IFN-γ," J. Immmol. 162(7):4140-4147.
Anonymous (1988). "Macrophage Colony-Stimulating Factor 1 Receptor (P07333),", 36 pages.
Anonymous (1988). "MCSF Receptor Antibody (AB 10676),", 2 pages.
Armant, M. et al. (1996). "Functional CD40 Ligand Expression on T Lymphocytes in the Absence of T Cell Receptor Engagement: Involvement in Interleukin-2-Induced Interleukin-12 and Interferon-Gamma Production," Eur. J. Immunol. 26(7):1430-1434.
ATCC CCL 87—"Jiyoye,", retrieved from https//www.atcc.org/Products/All/CCL-87.aspx, last visited Jul. 12, 2019, 3 pages.
Banchereau, J. et al. (1995). "Functional CD40 Antigen on B Cells, Dendritic Cells and Fibroblasts," Adv. Exp. Med. & Biol. 378:79-83.
Bauer, S. et al. (2001). "Human TLR9 Confers Responsiveness to Bacterial DNA Via Species-Specific CpG Motif Recognition," Proc. Natl. Acad. Sci. USA. 98(16):9237-9242.
Bauer, S. et al. (2002). "Bacterial CpG-DNA Licenses TLR9," Current Topics in Microbiology and Immunology 270:145-154.
Beatty, G.L. et al. (2011). "CD40 Agonists Alter Tumor Stroma and Show Efficacy Against Pancreatic Carcinoma in Mice and Humans," Science 331(6024):1612-1616, 9 pages.
Beiboer, S.H.W. et al. (2000). "Guided selection of a pan carcinoma specific antibody reveals similar binding characteristics yet structural divergence between the original murine antibody and its human equivalent," J Mol Biol. 296(3):833-849.
Bellovin, D. I. et al. (2015). "Tumor Weight (mean g SEM) Tumor Weight (mean g SEM) cmFPA008, an Anti-Mouse CSF-IR Antibody, Combines with Multiple Immunotherapies to Reduce Tumor Growth in Nonclinical Models", Poster, 1 page.
Bennett, S.R. et al. (1997). "Induction of a CD8+ Cytotoxic T Lymphocyte Response by Cross-Priming Requires Cognate CD4+ T Cell Help," J. Exp. Med. 186(1):65-70.
Bennett, S.R. et al. (1998). "Help for Cytotoxic-T-Cell Responses is Mediated by CD40 Signalling," Nature 393 (6684):478-480.
Boerner, P. et al. (1991). "Production of a Antigen-Specific Human Monoclonal Antibodies from In Vitro-Primed Human Splenocytes,"J. Immunol. 147(1):86-95.
Bonham et al. (2009). "Antagonistic Antibodies to c-fms Block c-fms-Mediated Activities Reduce Tumor-Associated Macrophages and Decrease Tumor Growth in Preclinical Models," In Proc Am Assoc Cancer Res 50:503. Abstract #2077, 1 page.
Brahmer et al., (2012) "Safety and Activity of anti-PD-L1 Antibody in Patients With Advanced Cancer," N Engl J Med. 366(26): 2455-2465.
Brassard, D.L. et al. (2002). "Interferon-α as an Immunotherapeutic Protein," J Leukoc. Biol. 71(4):565-581.
Bristol-Myers Squibb Cinical Trial (2009). "Multiple Ascending Dose (MDX1105-01) (Anti-PDL1)," retrieved from https://clinicaltrials.gov/ct2/show/NCT00729664 lasted visited on Aug. 10, 2021, 8 pages.
Brossart, P. et al. (1998). "Generation of Functional Human Dendritic Cells From Adherent Peripheral Blood Monocytes by CD40 Ligation in the Absence of Granulocyte-Macrophage Colony-Stimulating Factor," Blood 92 (11):4238-4247.
Brown, M. et al. (1996) "Tolerance to Single, but Not Multiple, Amino Acid Replacements in Antibody VH CDR2," J. Immunol. 156:3285-3291.
Bryne, K.T. et al. (2016). "CSF-IR-Dependent Lethal Hepatotoxicity When Agonistic CD40 Antibody is Given before but Not after Chemotherapy", J. Immunol. 197(1):179-187, 20 pages.
Brüggemann, M. et al. (1993). "Designer Mice: The Production of Human Antibody Repertoires in Transgenic Animals," Year in Immunology. 7:33-40.
Buhlmann J.E. et al., (1995). "In the Absence of a CD40 Signal, B Cells are Tolerogenic," Immunity 2:645-653.
Burmester, G.R. et al. (2011). "Mavrilimumab, A Human Monoclonal Antibody Targeting GM-CSF Receptor[alpha], In Subjects With Rheumatoid Arthritis: A Randomised, Double-Blind, Placebo-Controlled, Phase 1, First-in-Human Study," Ann Rheum Dis. 70(9):1542-1549.
Caldas, C. et al. (2003). "Humanization of the Anti-CD-18 Antibody 6.7: An Unexpected Effect of a Framework Residue in Binding to Antigen," Mol. Immunol. 39(15):941-952.
Carbone, E. et al., (1997). "A New Mechanism of NK Cell Cytotoxicity Activation: The CD40-CD40 Ligand Interaction," J. Exp. Med. 185(12):2053-2060.
Carpentier, A.F. et al. (2006). "Phase 1 Trial of a CpG Oligodeoxynucleotide for Patients With Recurrent Glioblastoma," Neuro-Oncology 8(1):60-66.
CAS No. 880486-59-9, retrieved from https:pubchem.ncbi.nlm.nih.gov/substance/135323347, last visited Jul. 12, 2019. 3 pages.
Casset, F. et al. (2003) "A Peptide Mimetic of an Anti-CD4 Monoclonal Antibody by Rational Design," BBRC 307:198-205.
Caux, C. et al. (1994). "Activation of Human Dendritic Cells Through CD40 Cross-Linking," J. Exp. Med. 180 (4):1263-1272.
Cella, M. et al. (1996). "Ligation of CD40 on Dendritic Cells Triggers Production of High Levels of Interleukin-12 and Enhances T Cell Stimulatory Capacity: T-T Help Via APC Activation," J Exp. Med. 184(2):747-752.
Chambers, S.K. (2009). "Role of CSF-1 in Progression of Epithelial Ovarian Cancer," Future Oncol 5(9):1429-1440, 18 pages.

(56) References Cited

OTHER PUBLICATIONS

Chari, R.V.J. et al., (1992). "Immunoconjugates Containing Noveal maytansinoids: Promising Anticancer Drugs," Cancer Res. 52:127-131.
Chaussabel, D. et al. (1999), "CD40 Ligation Prevents Trypanosoma cruzi Infection through Interleukin-12 Upregulation," Infection & Immunity 67(4):1929-1934.
Coffman, R.L. et al. (2010) "Vaccine Adjuvants: Putting Innate Immunity to Work," Immunity 33(4):492-503, 21 pages.
Cole, S.P.C. et al. (1985), "The EBV-Hybridoma Technique and its Applicaton to Human Lung Cancer," in Monoclonal Antibodies and Cancer Therapy, Alan R. Liss, p. 77-96.
CP-870,893—"CD40 Agonist Monoclonal Antibody CP-870,893,", retrieved from https://www.ncbi.nlm.nih.gov/medgen/?term=CP-870,893, last visited Jul. 12, 2019, 2 pages.
Dalpke, A.H. et al. (2002). "Phosphodiester CpG Oligonucleotides as Adjuvants: Polyguanosine Runs Enhance Cellular Uptake and Improve Immunostimulative Activity of Phosphodiester CpG Oligonucleotides in vitro and in vivo," Immunology 106(1):102-112.
Damiano, V. et al. (2006). "Novel Toll-Like Receptor 9 Agonist Induces Epidermal Growth Factor Receptor (EGFR) Inhibition and Synergistic Antitumor Activity With EGFR Inhibitors," Clin. Cancer Res. 12(2):577-583.
Davies, J. et al. (1996) "Affinity Improvement of Single Antibody VH Domains: Residues in all Three Hypervariable Regions Affect Antigen Binding," Immunol. 2:169-179.
De Palma, M. et al. (2013), "Macrophage Regulation of Tumor Responses to Anticancer Therapies" Cancer Cell 23(3):277-286.
Deckers, J.G.M. et al. (1998). "IL-4 and IL-13 Augment Cytokine- and CD40-Induced RANTES Production by Human Renal Tubular Epithelial Cells in vitro," J. The Am Society of Nephrology 9:1187-1193.
Denardo, D.G. et al. (2011). "Leukocyte Complexity Predicts Breast Cancer Survival an Dfunctionally Regulates Response to Chemotherapy," Cancer Research 1(1):1-14.
Denfeld, R. W. et al. (1996). "CD40 is Functionally Expressed on Human Keratinocytes," Eur. J. Imrmmol. 26 (10):2329-2334.
Dewar, A.L. et al. (2005). "Macrophage Colony-Simulating Factor Receptor c-fms is a Novel Target of Imatinib," Blood, 105(8):3127-3132.
Diehl, L. et al. (1999). "CD40 Activation in Vivo Overcomes Peptide-Induced Peripheral Cytotoxic T-Lymphocyte Tolerance and Augments Anti-Tumor Vaccine Efficacy," Nature Medicine 5(7):774-779.
Donepudi, M. et al. (1999). "Signaling Through CD40 Enhances Cytotoxic T Lymphocyte Generation by CD8+ T Cells From Mice Bearing Large Tumors," Cancer Immunol. Immunother. 48(2-3):153-164.
Dubowchik, G.M. et al. (2002). "Doxorubicin Immunoconjugates Containing Bivalent, Lysosomally-Cleavable Dipeptide Linkages," Bioorganic & Medicinal ChemistryLetters 12:1529-1532.
English Translation of Notification of Reasons for Rejection for Japanese Patent Application No. 2012-542522, dated Feb. 25, 2014 (3 pages).
European Search Report for Application No. EP 09007224.0 pp. 1-9 (dated Nov. 24, 2009).
European Search Report for Application No. EP 09015310 pp. 1-8 (dated Sep. 20, 2010).
Extended Search Report for European Patent Application No. EP 12153519.4, dated Aug. 2, 2012 (8 pages).
Ferlin, W.G. et al. (1998). "The induction of a Protective Response in Leishmania major-infected BALB/c Mice With Anti-CD40 mAb," Eur. J. Immunol. 28(2):525-531.
Flatman, S. et al. (2007, e-pub. Dec. 11, 2006). "Process Analytics for Purification of Monoclonal Antibodies," J. Chromatogr. B. 848:79-87.
Flick, M.B. et al. (1997), "Recognition of Activated CSF-1 Receptor in Breast Carcinomas by a Tyrosine 723 Phosphospecific Antibody," Oncogene 14:2553-2561.

Flores-Romo, L. et al. (1997). "CD40 Ligation on Human Cord Blood CD34+ Hematopoietic Progenitors Induces Their Proliferation and Differentiation into Functional Dendritic Cells," J. Exp. Med. 185(2):341-349.
Flores-Romo, L. et al. (1993). "Anti-CD40 Antibody Stimulates the VLA-4-Dependent Adhesion of Normal and LFA-1-Deficient B Cells to Endothelium," Immunol. 79(3):445-451.
Foy, T.M. et al. (1996). "Immune Regulation by CD40 and Its Ligand GP39," Ann. Rev. of Immunol. 14:591-617.
French, R.R. et al. (1999). "CD40 Antibody Evokes a Cytotoxic T-Cell Response That Eradicates Lymphoma and Bypasses T-Cell Help," Nature Medicine 5(5):548-553.
Funakoshi, S. et al. (1996). "Differential in vitro and in vivo Antitumor Effects Mediated by Anti-CD40 and Anti-CD20 Monoclonal Antibodies Against Human B-Cell Lymphomas," J. Immunotherapy with Emphasis on Tumor Immunol. 19(2):93-101.
Galluzzi, L. et al. (2012). "Trial Watch: Experimental Toll-like Receptor Agonists for Cancer Therapy," OncoImmunology 1(5):699-716.
Genentech. "Our Pipeline," retrieved from https://www.gene.com/medical-professionals/pipeline, last visited Aug. 10, 2021, 7 pages.
Gordon, M.S. et al. (2013). "Abstract. LB-288: A Phase I Study of MPDL3280A, An Engineered PD-L1 Antibody in Patients With Locally Advanced or Metastatic Tumors," Proceedings: AACR 104th Annual Meeting 2013, 4 pages.
Grammar, A.C. et al. (1998). "TNF Receptor-Associated Factor-3 Signaling Mediates Activation of p38 and Jun N-Terminal Kinase, Cytokine Secretion, and Ig Production Following Ligation of CD40 on Human B Cells," J. Immunol. 161:1183-1193.
Grewal, I.S. et al. (1998). "CD40 and CD154 in Cell-Mediated Immunity," Ann. Rev. of Imrmmol. 16:111-135.
Grewal, I.S. et al. (1996). "Requirement for CD40 Ligand in Costimulation Induction, T Cell Activation, and Experimental Allergic Encephalomyelitis," Science 273(5283):1864-1867.
Grewal, I.S. et al. (1995). "Impairment of Antigen-Specific T-Cell Priming in Mice Lacking CD40 Ligand," Nature 378(6557):617-620.
Grousson, J. et al. (1998). "Effects of CD40 Ligation on Human Keratinocyte Accessory Function," Archives of Dermatol. Res. 290(6):325-330.
Gruss, H.J. et al. (1994). "Expression and Function of CD40 on Hodgkin and Reed-Sternberg Cells and the Possible Relevance for Hodgkin's Disease," Blood 84(7):2305-2314.
Hamilton, J.A. (2008). "Colony-Stimulating Factors in Inflammation and Autoimmunity," Nat Rev Immunol.8 (7):533-544.
Haran-Ghera, N. et al. (1997)., "Increased Circulating Colony-Stimulating Factor-1 (CSF-1) in SJL/J Mice Eith Radiation-Induced Acute Myeloid Leukemia (AML) is Associated With Autocrine Regulation of AML Cells by CSF-1," The American Society of Hematology 89(7):2537-2545.
Hayashi, S.-I. et al. (1997). "Osteoclast Precursors in Bone Marrow and Peritoneal Cavity," J. Cell Physiol. 170 (3):241-247.
Heath, A.W. et al. (1994). "Monoclonal Antibodies to Murine CD40 Define Two Distinct Functional Epitopes," Eur. J Immunol. 24(8):1828-1834.
Hemmi, H. et al. (2000). "A Toll-Like Receptor Recognizes Bacterial DNA," Nature 408(6813):740-745.
Hinman, L.M. et al. (1993). "Preparation and Characterization of Monoclonal Antibody Conjugates of the Calicheamicins: A Novel and Potent Family of Antitumor Antibiotics," Cancer Research 53:3336-3342.
Hirano, A. et al. (1999). "Inhibition of Human Breast Carcinoma Growth by a Soluble Recombinant Human CD40 Ligand," Blood 93(9):2999-3007.
Hollenbaugh, D. et al. (1995). "Expression of Functional CD40 by Vascular Endothelial Cells," J. Exp. Med. 182:33-40.
Holt, L. et al. (2003) "Domain Antibodies: Proteins for Therapy," Trends in Biotechnology 21(11): 484-490.
Hoogenboom, H.R. et al. (1992). "By-Passing Immunisation: Human Antibodies from Synthetic Repertoires of Germline VH Gene Segments Rearranged in vitro," Journal of Molecular Biology 227(2):381-388.

(56) References Cited

OTHER PUBLICATIONS

Huang, A.Y. et al. (1994). "Bone Marrow-Derived Cells Present MHC Class I-Restricted Tumour Antigens in Priming of Antitumour Immune Responses," Ciba Foundation Symp. 187:229-244.
Huston, J.S. et al. (1991). "Protein Engineering of Single-Chain Fv Analogs and Fusion Proteins," Methods in Enzymology 203:46-88.
Ide, H. et al. (2002, e-pub. Oct. 15, 2002). "Expression of Colony-Stimulating Factor 1 Receptor During Prostrate Development and Prostate Cancer Progression," Proc. Natl. Acad. Sci. U.S.A. 99(22):14404-14409.
International Preliminary Report on Patentability dated Feb. 26, 2019, for PCT Application No. PCT/EP2017/070570, filed Aug. 14, 2017, 9 pages.
International Search Report and Written for International Patent Application No. PCT/EP2013/054676, dated May 7, 2013, filed Aug. 3, 2013, 18 pages.
International Search Report and Written Opinion for PCT Application No. PCT/EP2014/057909, dated Sep. 1, 2014, filed on Apr. 17, 2014, 14 pages.
International Search Report and Written Opinion for International Patent Application No. PCT/EP2011/053214, dated Apr. 28. 2011, filed Mar. 3, 2011, 13 pages.
International Search Report and Written Opinion for International Patent Application No. PCT/EP2012/075241, dated Feb. 22, 2013, filed Dec. 12, 2012, 14 pages.
International Search Report and Written Opinion for PCT Application No. PCT/EP2014/069451, dated Nov. 18, 2014, filed on Sep. 11, 2014, 13 pages.
International Search Report and Written Opinion dated Dec. 18, 2020, filed Sep. 29, 2020, directed to International Application No. PCT/US2020/053213, 13 pages.
International Search Report and Written Opinion dated Oct. 9, 2017, for PCT Application No. PCT/EP2017/070570, filed Aug. 14, 2017, 12 pages.
Ishida, T.K. et al. (1996). "TRAF5, a Novel Tumor Necrosis Factor Receptor-Associated Factor Family Protein, Mediates CD40 Signaling," Proc. Natl. Acad. Sci. USA 93(18):9437-9442.
Iwai, Y. et al., (2002). "Involvement of PD-L1 on Tumor Cells in the Escape from Host immune System and Tumor Immunotherapy by PD-L1 Blockade," Proc. Natl. Acad. Sci. USA 90(19):12293-12297.
Jakobovits, A. et al. (1993). "Germ-Line Transmission and Expression of a Human-Derived Yeast Artificial Chromosome," Nature 362:255-258.
Jakobovits, A. et al. (1993), "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90 (6):2551-2555.
Jeffrey, S.C. et al. (2006, e-pub. Nov. 3, 2005). "Dipeptide-based Highly Potent Doxorubicin Antibody Conjugates," Bioorganic Medicinal Chemistry Letters 16:358-362.
Jeppson, J.D. et al. (1998). "Requirement, for Dual Signals by Anti-CD40 and IL-4 for the Induction of Nuclear Factor-kB, IL-6, and IgE in Human B Lymphocytes," J. Immunol. 161:1738-1742.
Jones, K.W. et al. (1996). "Activated T Hybridomas induce Upregulation of B7-1 on Bystander B Lymphoma Cells by a Contact-Dependent Interaction Utilizing CD40 Ligand," Cellular Immunol. 174(1):42-53.
Jose, M.D. et al. (2003). "Blockade of Macrophage Colony-Stimulating Factor Reduces Macrophage Proliferation and Accumulation in Renal Allograft Rejection," American Journal of Transplantation 3:294-300.
Kabat, E.A et al. (1983). "Tabulation and Analysis of Amino Acid and Nucleic Acid Sequences of Precursors, v-Regions, c-Regions, j-Chain, beta2-Microglobulins, Major Histocompatibility Antigens, Thy-1, Complement, c-Reactive Protein, Thymopoietin, Post-gamma Globulin, and alpha2macroglobulin," Sequences of Proteins of Immunological Interest. U.S. Dept. of Health and Human Services, 10L, 2 pages.

Kacinski, B.M. et al. (1990). "Ovarian Adenocarcinomas Express fms-Complementary Transcripts and fms Antigen, Often With Coexpression of CSF-1," American Journal of Pathology 137(1):135-147.
Kandimalla, E.R. et al. (2003). "Divergent Synthetic Nucleotide Motif Recognition Pattern: Design and Development of Potent Immunomodulatory Oligodeoxyribonucleotide Agents With Distinct Cytokine Induction Profiles," Nucleic Acids Res. 31(9):2393-2400.
Kandimalla, E.R. et al. (2001). "Effect of Chemical Modifications of Cytosine and Guanine in a CpG-Motif of Oligonucleotides: Structure-Immunostimulatory Activity Relationships," Bioorg. Med. Chem. 9(3):807-813.
Kandimalla, E.R. et al. (2005). "Immunomodulatory Oligonucleotides Containing a Cytosine-Phosphate-2'-Deoxy-7-Deazaguanosine Motif as Potent Toll-Like Receptor 9 Agonists," Proc. Natl. Acad. Sci. USA. 102(19):6925-6930.
Kandimalla, E.R. et al. (2003). "A Dinucleotide Motif in Oligonucleotides Shows Potent Immunomodulatory Activity and Overrides Species-Specific Recognition Observed With CpG Motif," Proc. Natl. Acad. Sci, USA, 100(24):14303-14308.
Katada, Y. et al. (1996). "B Cell-B Cell Interaction Through Intercellular Adhesion Molecule-1 and Lymphocyte Functional Antigen-1 Regulates Immunoglobulin E Synthesis by B Cells Stimulated With Interleukin-4 and Anti-CD40 Antibody," Eur. J. Immunol. 26(1):192-200.
Kawai, O. et al. (2008, e-pub. Jul. 31, 2008). "Predominant Infiltration of Macrophages and CD8+ T Cells in Cancer Nests is a Significant Predictor of Survival in Stage IV Nonsmall Cell Lung Cancer," Cancer 6:1387-1395.
Kawakami, Y. et al. (2000). "Macophage-Colony Stimulating Factor Inhibits the Growth of Human Ovarian Cancer Cells in vitro," European Journal of Cancer 36:1991-1997.
Khalil, M. et ai. (2007). "Anti-CD40 Agonist Antibodies: Preclinical and Clinical Experience," Update Cancer Ther.; 2(2):61-65, 9 pages.
Kiener, P.A et al. (1995). "Stimulation of CD40 With Purified Soluble gp39 Induces Proinflammatory Responses in Human Monocytes," J. Immunol. 155(10):4917-4925.
King, H.D. et al. (2002, e-pub. Aug. 14, 2002). "Monoclonal Antibody Conjugates of Doxorubicin with Branched Peptide Linkers: Inhibition of Aggregation by Methoxytriethyleneglycol Chains," J. Med. Chem. 45(19):4336-4343.
Koch, F. et al. (1996). "High Level IL-12 Production by Murine Dendritic Cells: Upregulation Via MHC Class II and CD40 Molecules and Downregulation by IL-4 and IL-10," J. Exp. Med. 184(2)741-746.
Kommoss, F. et al. (1994). "Co-Expression of M-CSF Transcripts and Protein, Fms (M-CSF Receptor) Transcripts and Protein, and Steroid Receptor Content in Adenocarcinomas of the Ovary," Journal of Pathology 174:111-119.
Kratz, F. et al. (2006). "Prodrugs of Anthracyclines in Cancer Chemotherapy," Current Medicinal Chemistry 13(5):477-523.
Krieg, A.M. (2008). "Toll-Like Receptor 9 (TLR9) Agonists in the Treatment of Cancer," Oncogene 7;27(2):161-167.
Krug, A. et al. (2001). "Identification of CpG Oligonucleotide Sequences With High Induction Of IFN-α/β in Plasmacytoid Dendritic Cells," Eur J Immunol, 31(7):2154-2163.
Kuester, K. et al. (2006). "Pharmacokinetics of Monoclonal Antibodies," Chapter 3 in "Pharmacokinetics and Pharmacodynamics of Biotech Drugs," Meibohm (Ed.), Wiley-VCH, pp. 45-91.
Kuniyoshi, J.S. et al. (1999). "Dendritic Cell Secretion of IL-15 is Induced by Recombinant huCD40LT and Augments the Stimulation of Antigen-Specific Cytolytic T Cells," Cellular Immunol. 193(1):48-58.
Langmead, B. et al. (2012) "Fast Gapped-Read Alignment With Bowtie 2," Nat Methods 9(4):357-359, 8 pages.
Lazaar, A.L. et al. (1998). "CD40-Mediated Signal Transduction in Human Airway Smooth Muscle," J. Immunol. 161:3120-3127.
Lee, A. et al. (1992). "Functional Dissection of Structural Domains in the Receptor for Colony-Stimulating Factor-1," J. Biol. Chem. 267(23):16472-16483.

(56) References Cited

OTHER PUBLICATIONS

Lee, H.H et al. (1999), "Specificities of CD40 Signaling: involvement of TRAF2 in CD40-Induced NF-κB Activation and Intercellular Adhesion Molecule-1 Up-Regulation," Proc. Natl Acad. Sci. USA. 96(4):1421-1426.

Lewis, T.S. et al. (2011, e-pub. May 24, 2011). "Distinct Apoptotic Signaling Characteristics of the Anti-CD40 Monoclonal Antibody Dacetuzumab and Rituximab Produce Enhanced Antitumor Activity in Non-Hodgkin Lymphoma," Clin Cancer Res. 17(14):4672-4681.

Li, et al. (2011). "Inhibitory Fcγ Receptor Engagement Drives Adjuvant and Anti-Tumor Activities of Agonistic CD40 Antibodies," Science 333(6045):1030-1034, 13 pages.

Li, J. et al. (2012). "Abstract P4-04-01: Combination of Intratumoral CpG With SystemicAnti-OX40 and Anti-CTLA4 mAbs Eradicates Established Triple Negative Breast Tumors in Mice," Cancer Research (retrieved Mar. 26, 2015 from http://cancerres.aacrjournals.org/content/72/24_Supplement/P4-04-01.short), 4 pages.

Liang, X. et al., (2010, e-pub. Mar. 25, 2010). "Toll-like Receptor 9 Signaling by CpG-B Oligodeoxynucleotides Induces an Apoptotic Pathway in Human Chronic Lymphocytic Leukemia B Cells," Blood 115(24):5041-5052.

Lin, E.Y. et al. (2001). "Colony-Stimulating Factor 1 Promotes Progression of Mammary Tumors to Malignancy," J. Exp. Med. 193(6):727-740.

Lode, H.N. et al. (1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.

Longhi, M.P. et al. (2009). "Dendritic Cells Require a Systemic Type I Interferon Response to Mature and Induce CD4+ Th1 Immunity With Poly IC as Adjuvant," J Exp Med 206(7):1589-1602.

Maccallum, R.M. et al. (1996). "Antibody-Antigen Interactions: Contact Analysis and Binding Site Topography," J. Mol. Biol. 262:732-745.

Macdonald, K.P.A et al., (2010). "An Antibody Against the Colony-Stimulating Factor 1 Receptor Depletes the Resident Subset of Monocytes and Tissue-and Tumor-Associated Macrophages but Does Not Inhibit Inflammation," Blood 116(19):3955-3963.

Mackey, M.F. et al. (1998). "Cutting Edge: Dendritic Cells Require Maturation via CD40 to Generate Protective Antitumor Immunity," J. Immunol. 161:2094-2098.

Mackey, M.F. et al. (1998). "The Role of CD40/CD154 Interactions in the Priming, Differentiation, and Effector Function of Helper and Cytotoxic T Cell," J. Leukocyte Biol. 63(4):418-428.

Mackey, M.F. et al. (1997), "Protective Immunity Induced by Tumor Vaccines Requires Interaction between CD40andits Ligand, CD154," Cancer Research 57:2569-2574.

Mahl, R.S. et al. (2013, e-pub. Sep. 2, 2013). "Sweeten PAMPs: Role of Sugar Complexed PAMPs in Innate Immunity and Vaccine Biology," Front Immunol 4:248.

Mancinio, A.T. et al. (2001, e-pub. Jul. 24, 2001). "Breast Cancer Increases Osteoclastogenesis by Secreting M-CSF and Upregulating RANKL in Stromal Cells," Journal of Surgical Research 100:18-24.

Marks, J.D. et al. (1991). "By-Passing Immunization. Human Antibodies From V-Gene Libraries Displayed on Phage," J. Mol. Biol. 222:581-597.

Martin, T.A .et al. (2003). "Growth and Angiogenesis of Human Breast Cancer in a Nude Mouse Tumour Model is Reduced by NK4, a HGF/SF Antagonist," Carcinogenesis. 24(8):1317-1323.

Martin-Fontecha, A. et al. (1999). "Triggering of Murine NK Cells by CD40 and CD86 (B7-2)," J. Immunol. 162:5910-5916.

Martinez, F.O. et al. (2013). "Genetic Programs Expressed in Resting and IL-4 Alternatively Activated Mouse and Human Macrophages: Similarities and Differences," Blood 21(9):e57-e69.

Matsusaki, M. et al. (2019). "Three-Dimensional Cell Culture Technique and Pathophysiology," Advanced Drug Delivery Reviews, 74:95-103, 36 pages.

Mayumi, M. et al. (1995), "Session II: Allergy and Intracellular Signal Transmission Mechanisms: Role of LFA-1/ICAM-1-Dependent Cell Adhesion in CD40-Mediated Inhibition of Anti-IgM Antibody-Induced B-Cell Death," J. Allergy & Clin. Immunol. 96(6 Pt. 2):1136-1144.

Mcdyer, J.F. et al. (1999), "Differential Effects of CD40 Ligand/Trimer Stimulation on the Ability of Dendritic Cells to Replicate and Transmit HIV Infection: Evidence for CC-Chemokine-Dependent and -independent Mechanisms," J. Immunol. 162:3711-3717.

Meng, Y. et al. (2005). "Successful Combination of Local CpG-ODN and Radiotherapy in Malignant Glioma," Int J Cancer 116(6):992-997.

Morrison, S.L. et al. (1984), "Chimeric Human Antibody Molecules: Mouse Antigen-Binding Domains With Human Constant Region Domains," Proc. Natl. Acad. Sci. USA 81:6851-6855.

Mortazavi, A. et al. (2008, e-pub. May 30, 2008). "Mapping and Quantifying Mammalian Transcriptomes by RNA-Seq," Nat Methods 5(7):621-628.

Murad, Y.M. et al. (2009). "CpG Oligodeoxynucleotides as TLR9 Agonists: Therapeutic Applications in Cancer," BioDrugs. 23(6):361-375.

Nagy, A. et al. (2000). "Stability of Cytotoxic Luteinizing Hormone-Releasing Hormone Conjugate (AN-152) Containing Doxorubicin 14-O-Hemiglutarate In Mouse and Human Serum in Vitro: Implications for the Design of Preclinical Studies," Proc. Nat'l. Acad. Sci. USA. 97(2):829-834.

Neuberger, M.S. et al. (1985). "A Hapten-Specific Chimaeric IgE Antibody With Human Physiological Effector Function," Nature 314:268-270.

Ngan, H.Y. et al. (1999). "Proto-oncogenes and p53 Protein Expression in Normal Cervical Stratified Squamous Epithelium and Cervical Intra-Epithelial Neoplasia," Eur. J. Cancer 35(10):1546-1550.

Nicola, N.A. et al. (1993). "Neutralizing and Nonneutralizing Monoclonal Antibodies to the Human Granulocyte-Macrophage Colony-Stimulating Factor Receptor α-Chain," Blood 82(6): 1724-1731.

Noelle, R.J (1998). "CD40 and Its Ligand in Cell-Mediated Immunity," Agents & Actions Suppl. 49:17-22.

Parsa, A.T. et al. (2007, e-pub. Dec. 20, 2006). "Loss of Tumor Suppressor PTEN Function Increases B7-H1 Expression and Immunoresistance In Glioma," Nat. Med. 13(1):84-88.

Patel, S. et al. (2009). "Colony-Stimulating Factor-1 Receptor Inhibitors for the Treatment of Cancer and Inflammatory Disease," Curr Top Med Chem. 9(7):599-610.

Paul, W.E. (1993). Chapter 9: Fundamental Immunology, 3rd ed. Raven Press, NY., 292-295, 6 pages.

Paulie, S. et al. (1985), "A p50 Surface Antigen Restricted to Human Urinary Bladder Carcinomas and B LYMphocytes," Cancer Immunol. Immunother. 20(1):23-28.

Pullen S.S. et al. (1999). "CD40 Signaling through Tumor Necrosis Factor Receptor-associated Factors (TRAFs)," J. Biol Chem 274(20):14246-14254.

Pullen, S.S. et al. (1998). "CD40-Tumor Necrosis Factor Receptor-Associated Factor (TRAP) Interactions: Regulation of CD40 Signaling Through Multiple TRAF Binding Sites and TRAF Hetero-Oligomerization," Biochemistry 37(34):11836-11845.

Putta, M.R. et al. (2006, e-pub. Jun. 23, 2006). "Novel Oligodeoxynucleotide Agonists of TLR9 Containing N3-Me-dC or N1-Me-dG Modifications," Nucleic Acids Res. 34(11):3231-3238.

Queen, C. et al. (1989). "A Humanized Antibody That Binds to the Interleukin 2 Receptor," Proc. Natl Acad. Sci. USA 86:10029-10033.

Ridge, S.A. et al. (1990). "FMS Mutations in Myelodysplastic, Leukemic, and Normal Subjects," Proc. Natl. Acad. Sci. USA 87:1377-1380.

Riechmann, L. et al. (1988). "Reshaping Human Antibodies for Therapy," Nature 332:323-327.

Rothenfusser, S. et al. (2002). "Plasmacyloid Dendritic Cells: The Key to CpG," Human Immunology 63 (12):1111-1119.

Roussel, M.F. et al. (1989). "Mouse NIH 3T3 Cells Expressing Human Colony-Stimulating Factor 1 (CSF-1) Receptors Overgrow

(56) References Cited

OTHER PUBLICATIONS in Serum-Free Medium Containing Human CSF-1 as Their Only Growth Factor," Proc Natl Acad Sci US A. 86(20):7924-7927.
Roy, M. et al. (1995). "Studies on the Interdependence of gp39 and B7 Expression and Function During Antigen-Specific Immune Responses," Eur. J. Immunol, 25(2):596-603.
Ruggiero, G. et al. (1996). "CD40 Expressed on Thymic Epithelial Ceils Provides Costimulation for Proliferation but Not for Apoptosis of Human Thymocytes," J. Immunol. 156(10):3737-3746.
Sandmann, T. et al. (2014, e-pub. Oct. 15, 2013). "gCMAP: User-Friendly Connectivity Mapping With R," Bioinformatics 30(1):127-128.
Santos-Argumedo, L. et al. (1994). "Antibodies to Murine CD40 Protect Normal and Malignant B Cells From Induced Growth Arrest," Cellular Immunol. 156(2):272-285.
Sapi, E. et. al. (1999). "Effect of All-trans-Retinoic Acid on c-fms Proto-Oncogene [Colony-Stimulating Factor 1 (CSF-1) Receptor] Expression and CSF-1-Induced invasion andAnchorage-Independent Growth of Human Breast Carcinoma Ceils," Cancer Res. 59:5578-5585.
Schaniel, C. et al. (1998). "Activated Murine B Lymphocytes and Dendritic Cells Produce a Novel CC Chemokine which Acts Selectively on Activated T Cells," J. Exp. Med. 188(3):451-463.
Schmieder, A. et al. (2012, e-pub. Feb. 13, 2012). "Differentiation and Gene Expression Profile of Tumor-Associated Macrophages," Semin Cancer Biol. 22(4):289-297.
Schoenberger, S.P. et al. (1998). "T-Cell Help for Cytotoxic T Lymphocytes is Mediated by CD40-CD40L Interactions," Nature 393(6684):480-483.
Schroder, K. et al. (2007). "PU.1 and ICSBP control constitutive and IFN-γ-regulated Tir9 Gene Expression in Mouse Macrophages," J. Leukoc. Biol. 81(6):1577-1590.
Shadduck, R.K. et al. (1996). "Paradoxical Stimulation of Normal and Leukemic Rat Hematopoiesis by Monoclonal Antibody to CSF-1 Receptor," Experimental Hematology 24:314-317.
Sherr, C.J. et al. (1985). "The c-fms Proto-Oncogene Product is Related to the Receptor for the Mononuclear Phagocyte Growth Factor, CSF-1 " Cell 41(3):665-676.
Sherr, C.J. et al. (1989). "Inhibition of Colony-Stimulating Factor-I Activity by Monoclonal Antibodies to the human CSF-1 Receptor," Blood 73(7):1786-1793.
Shulman, T. et al. (1997).."An Antibody Reactive With Domain 4 of the Platelet-Derived Growth Factor β Receptor Allows BB Binding While Inhibiting Proliferation by Impairing Receptor Dimerization," The Journal of Biological Chemistry 272(28):17400-17404.
Sotomayor, E.M. et al. (1999). "Conversion of Tumor-Specific CD4+ T-Cell Tolerance to T-Cell Priming Through in vivo Ligation of CD40," Nature Medicine 5(7):780-787.
Steidl, C. et al. (2010). "Tumor-Associated Macrophages and Survival in Classic Hodgkins's Lymphoma," N. Engl. J. Med. 362(10):875-885.
Steinhagen, F. et al. (2011, e-pub. Aug. 14, 2011). "TLR-Based Immune Adjuvants," Vaccine 29(17):3341-3355, 33 pages.
Strausberg et al. CSF1R Colony Stimulating Factor 1 Receptor [*Homo Sapiens*] Accession No. AAH47521 (2008, updated Jul. 11, 2021), 15 pages.
Subramanian, A. et al., (2005), "Gene Set Enrichment Analysis: A Knowledge-Based Approach for Interpreting Genome-Wide Expression Profiles," Proc. Natl. Acad. Sci. USA 102(43):15545-15550.
Sudo, T. et al. (1995). "Functional Hierarchy of c-kit and c-fms in Intramarrow Production of CFU-M" Oncogene 11(12):2469-2476.
Sundberg, E.J. (2009, e-pub. Feb. 24, 2009). "Structural Basis of Antibody-Antigen Interactions," Methods Mol Biol. 524:23-36.
Sutherland, C.L. et al. (1999). "An 11-Amino Acid Sequence in the Cytoplasmic Domain of CD40 is Sufficient for Activation of c-Jun N-Terminal Kinase, Activation of MAPKAP Kinase-2, Phosphorylation of IkBa, and Protection of WEHI-231 Cells from Anti-IgM-Induced Growth Arrest," J. Immunol. 162:4720-4730.

Séguin, R. et al. (1999). "Sensitized Lymphocytes and CD40 Ligation Augment lnterleukin-12 Production by Human Dendritic Cells in Response to Toxoplasma gondii," J. Infect. Diseases 179(2):467-474.
Taylor, J.R. et al. (2005). "FMS Receptor for M-CSF (CSF-1) is Sensitive to the Kinase Inhibitor Imatinib and Mutation of Asp-802 to Val Confers Resistance," Oncogene pp. 1-5.
Toes, R.E.M. et al., (1998), "CD40-C040 Ligand Interactions and Their Role in Cytotoxic T Lymphocyte Priming and Anti-Tumor Immunity," Seminars in Immunol. 10(6):443-448.
Torgov, M.Y. et al. (2005; e-published on Apr. 27, 2005). "Generation of an Intensely Potent Anthracycline by a Monoclonal Antibody-β-Galactosidase Conjugate," Bioconjugate Chem. 16:717-721.
Tortora, G. et al. (2010). "Novel Toll-Like Receptor 9 (TLR9) Agonists IMO Inhibits Tumor Growth an Cooperates With Cetuximab in K-Ras Mutant Colon Pancreatic Cancers," Proceedings of the American Association for Cancer Research. 51:146., 1 page.
Tsukamoto, N. et al. (1999). "Two Differently Regulated Nuclear Factor KB Activation Pathways Triggered by the Cytoplasmic Tail of CD40," Proc. Natl. Acad. Sci. USA 96(4):1234-1239.
Tutt, A.L. et al. (1998). "Monoclonal Antibody Therapy of B Cell Lymphoma: Signaling Activity on Tumor Cells Appears More Important Than Recruitment of Effectors," J. Immunol. 161:3176-3185.
Uejima, Y. et al. (1996), "Effect of Interleukin-10 on Anti-CD40- and Interleukin-4-Induced Immunoglobulin E Production by Human Lymphocytes," Int. Arch. of Allergy & Immunol. 110(3):225-232.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Van Dijk, M.A. et al. (2001). "Human Antibodies as Next Generation Therapeutics," Curr. Opin. Chem. Biol. 5:368-374.
Vitetta, E.S. et al. (1987). "Redesigning Nature's Poisons to Creare Anti-Tumor Reagents," Science 238:1098-1104.
Von Leoprechting, A. et al. (1999). "Stimulation of CD40 on Immunogenic Human Malignant Melanomas Augments Their Cytotoxic T Lymphocyte-mediated Lysis and Induces Apoptosis," Cancer Res. 59:1287-1294.
Vonderheide, R.H. et al. (2007). "Clinical Activity and Immune Modulation in Cancer Patients Treated With CP-870,893, A Novel CD40 Agonist Monoclonal Antibody," J Clin Oncol 25(7):876-883.
Waltenbaugh, C. et al. (2008). Immunology Lippincott's Illustrated Reviews. Philadelphia: Wolters Kluwer Health/Lippincott's Williams & Wilkins, p. 17, 5 pages.
Weiner, G.J. et al., (1997). "Immunostimulatory Oligodeoxynucleotides Containing the CpG Motif are Effective as Immune Adjuvants in Tumor Antigen Immunization," Proc. Natl. Acad. Sci. USA 94(20):10833-10837.
Weir, E.C. et al. (1996), "Colony Stimulating Factor-1 Plays a Role in Osteoclast Formation and Function in Bone Resorption Induced by Parathyroid Hormone and Parathyroid Hormone-Related Protein," Journal of Bone and Mineral 11(10):1474-1481.
White A.L. et al. (2011, e-pub. Jul. 8, 2011). "Interaction with FegammaRIIB is Critical for the Agonistic Activity of Anti-C040 Monoclonal Antibody," J Immunol. 187(4):1754-1763.
White, C.A. et al. (2001). "Antibody-Targeted Immunotherapy for Treatment of Malignancy," Annual Review of Medicine 52:125-145.
WHO Drug Information (2014), "International Nonproprietary Names for Pharmaceutical Substances (INN)," 28(2):111, 84 pages.
Yellin, M.J. et al. (1995). "Ligation of CD40 on Fibroblasts Induces CD54 (ICAM-1) and CD106 (VCAM-1) Up-Regulation and IL-6 Production and Proliferation," J. Leukocyte Biol. 58(2):209-216.
Yuzawa, S. et al. (2007). "Structural Basis for Activation of the Receptor Tyrosine Kinase KIT by Stem Cell Factor," Cell 130(2):323-334.
Zheng, G. et al. (2000). "Membrane-Bound Macrophage Colony-Stimulating Factor and Its Receptor Play Adhesion Molecule-Like Roles in Leukemic Cells," Leuk Res, 24(5):375-383.
Lianfang, Q. et al. (1997). "Biological Effect of Monoclonal Antibodies Against CSF1 & CSF1R on Human Hepatic Cancer Cells Transplanted I Nude Mice," Tumor 4:207-208, Chinese with English Translation, 4 pages.

(56) References Cited

OTHER PUBLICATIONS

Ries, C.H. et al. (2015). "CSH-1/CSF-1R Targeting Agents in Clinical Development For Cancer Therapy," Current Opinion in Pharmacology, 23:45-51.

Sica, A. et al. (2014). "Macrophage Plasticity and Polarization in Liver Homeostasis and Pathology," Hepatology 59:2035-2043.

* cited by examiner

```
                          SEQUENCE LISTING

<160> NUMBER OF SEQ ID NOS: 30

<210> SEQ ID NO 1
<211> LENGTH: 116
<212> TYPE: PRT
<213> ORGANISM: Artificial
<220> FEATURE:
<223> OTHER INFORMATION: heavy chain variable domain, anti-CSF-1R
      antibody emactuzumab

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Ser Trp Val Arg Gln Ala Pro Gly Gln Gly Leu Glu Trp Met
            35                  40                  45

Gly Val Ile Trp Thr Asp Gly Gly Thr Asn Tyr Ala Gln Lys Leu Gln
        50                  55                  60

Gly Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Asp Gln Arg Leu Tyr Phe Asp Val Trp Gly Gln Gly Thr Thr Val
                100                 105                 110

Thr Val Ser Ser
        115

<210> SEQ ID NO 2
<211> LENGTH: 106
<212> TYPE: PRT
<213> ORGANISM: Artificial
<220> FEATURE:
<223> OTHER INFORMATION: light chain variable domain, anti-CSF-1R
      antibody emactuzumab

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Asn Thr Tyr
```

```
                20                  25                  30
Val Ser Trp Tyr Gln Gln Lys Pro Gly Lys Ala Pro Lys Leu Leu Ile
            35                  40                  45

Tyr Ala Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Tyr Pro Thr
                85                  90                  95

Phe Gly Gln Gly Thr Lys Leu Glu Ile Lys
            100                 105

<210> SEQ ID NO 3
<211> LENGTH: 118
<212> TYPE: PRT
<213> ORGANISM: Artificial
<220> FEATURE:
<223> OTHER INFORMATION: heavy chain variable domain of anti-PD-L1
      antibody atezolizumab

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 4
<211> LENGTH: 108
<212> TYPE: PRT
<213> ORGANISM: Artificial
<220> FEATURE:
<223> OTHER INFORMATION: light chain variable domain of anti-PD-L1
      antibody atezolizumab

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
```

```
                    85                  90                  95

Thr Phe Gly Gln Gly Thr Lys Val Glu Ile Lys Arg
                100                 105

<210> SEQ ID NO 5
<211> LENGTH: 121
<212> TYPE: PRT
<213> ORGANISM: Artificial
<220> FEATURE:
<223> OTHER INFORMATION: heavy chain variable domain of anti-PD-L1
      antibody durvalumab

<400> SEQUENCE: 5

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
                100                 105                 110

Gln Gly Thr Leu Val Thr Val Ser Ser
            115                 120

<210> SEQ ID NO 6
<211> LENGTH: 108
<212> TYPE: PRT
<213> ORGANISM: Artificial
<220> FEATURE:
<223> OTHER INFORMATION: light chain variable domain of anti-PD-L1
      antibody durvalumab

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
                100                 105

<210> SEQ ID NO 7
<211> LENGTH: 120
<212> TYPE: PRT
<213> ORGANISM: Artificial
<220> FEATURE:
<223> OTHER INFORMATION: heavy chain variable domain of anti-PD1
```

-continued antibody pembrolizumab

<400> SEQUENCE: 7

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 8
<211> LENGTH: 111
<212> TYPE: PRT
<213> ORGANISM: Artificial
<220> FEATURE:
<223> OTHER INFORMATION: light chain variable domain of anti-PD1
      antibody pembrolizumab

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 9
<211> LENGTH: 113
<212> TYPE: PRT
<213> ORGANISM: Artificial
<220> FEATURE:
<223> OTHER INFORMATION: heavy chain variable domain of anti-PD1
      antibody nivolumab

<400> SEQUENCE: 9

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

```
Ala Val Ile Trp Tyr Asp Gly Ser Lys Arg Tyr Tyr Ala Asp Ser Val
         50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
             100                 105                 110

Ser
```

```
<210> SEQ ID NO 10
<211> LENGTH: 107
<212> TYPE: PRT
<213> ORGANISM: Artificial
<220> FEATURE:
<223> OTHER INFORMATION: light chain variable domain of anti-PD1
      antibody nivolumab

<400> SEQUENCE: 10

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
             100                 105
```

```
<210> SEQ ID NO 11
<211> LENGTH: 972
<212> TYPE: PRT
<213> ORGANISM: Homo sapiens

<400> SEQUENCE: 11

Met Gly Pro Gly Val Leu Leu Leu Leu Val Ala Thr Ala Trp His
 1               5                  10                  15

Gly Gln Gly Ile Pro Val Ile Glu Pro Ser Val Pro Glu Leu Val Val
             20                  25                  30

Lys Pro Gly Ala Thr Val Thr Leu Arg Cys Val Gly Asn Gly Ser Val
         35                  40                  45

Glu Trp Asp Gly Pro Pro Ser Pro His Trp Thr Leu Tyr Ser Asp Gly
 50                  55                  60

Ser Ser Ser Ile Leu Ser Thr Asn Asn Ala Thr Phe Gln Asn Thr Gly
 65                  70                  75                  80

Thr Tyr Arg Cys Thr Glu Pro Gly Asp Pro Leu Gly Gly Ser Ala Ala
                 85                  90                  95

Ile His Leu Tyr Val Lys Asp Pro Ala Arg Pro Trp Asn Val Leu Ala
             100                 105                 110

Gln Glu Val Val Val Phe Glu Asp Gln Asp Ala Leu Leu Pro Cys Leu
         115                 120                 125
```

-continued

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Ala Leu Thr Leu Val
        195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Tyr Lys Tyr Lys Gln Lys Pro
530                 535                 540

Lys Tyr Gln Val Arg Trp Lys Ile Ile Glu Ser Tyr Glu Gly Asn Ser

-continued

```
545                 550                 555                 560
Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
                595                 600                 605

Ala Val Leu Lys Val Ala Val Lys Met Leu Lys Ser Thr Ala His Ala
610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
                690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
                755                 760                 765

Leu Ala Ser Lys Asn Cys Ile His Arg Asp Val Ala Ala Arg Asn Val
                770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
                835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
                915                 920                 925

Ser Ser Arg Ser Gly Gly Ser Gly Ser Ser Ser Glu Leu Glu Glu
                930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 12
<211> LENGTH: 493
<212> TYPE: PRT
<213> ORGANISM: Artificial
<220> FEATURE:
<223> OTHER INFORMATION: human CSF-1R Extracellular Domain (domains D1-D5)

<400> SEQUENCE: 12

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
```

```
                355                 360                 365
Gly Trp Arg Ala Leu Thr Phe Glu Leu Thr Leu Arg Tyr Pro Pro Glu
        370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
        450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
                485                 490

<210> SEQ ID NO 13
<211> LENGTH: 292
<212> TYPE: PRT
<213> ORGANISM: Artificial
<220> FEATURE:
<223> OTHER INFORMATION: human CSF-1R fragment domains D1-D3

<400> SEQUENCE: 13

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
```

```
                225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
                275                 280                 285

Asn Leu Ile Gln
    290

<210> SEQ ID NO 14
<211> LENGTH: 218
<212> TYPE: PRT
<213> ORGANISM: Artificial
<220> FEATURE:
<223> OTHER INFORMATION: human CSF-1R fragment domains D4-D5

<400> SEQUENCE: 14

Val Val Glu Ser Ala Tyr Leu Asn Leu Ser Ser Glu Gln Asn Leu Ile
1               5                   10                  15

Gln Glu Val Thr Val Gly Glu Gly Leu Asn Leu Lys Val Met Val Glu
                20                  25                  30

Ala Tyr Pro Gly Leu Gln Gly Phe Asn Trp Thr Tyr Leu Gly Pro Phe
            35                  40                  45

Ser Asp His Gln Pro Glu Pro Lys Leu Ala Asn Ala Thr Thr Lys Asp
        50                  55                  60

Thr Tyr Arg His Thr Phe Thr Leu Ser Leu Pro Arg Leu Lys Pro Ser
65                  70                  75                  80

Glu Ala Gly Arg Tyr Ser Phe Leu Ala Arg Asn Pro Gly Gly Trp Arg
                85                  90                  95

Ala Leu Thr Phe Glu Leu Thr Leu Arg Tyr Pro Pro Glu Val Ser Val
                100                 105                 110

Ile Trp Thr Phe Ile Asn Gly Ser Gly Thr Leu Leu Cys Ala Ala Ser
            115                 120                 125

Gly Tyr Pro Gln Pro Asn Val Thr Trp Leu Gln Cys Ser Gly His Thr
        130                 135                 140

Asp Arg Cys Asp Glu Ala Gln Val Leu Gln Val Trp Asp Asp Pro Tyr
145                 150                 155                 160

Pro Glu Val Leu Ser Gln Glu Pro Phe His Lys Val Thr Val Gln Ser
                165                 170                 175

Leu Leu Thr Val Glu Thr Leu Glu His Asn Gln Thr Tyr Glu Cys Arg
                180                 185                 190

Ala His Asn Ser Val Gly Ser Gly Ser Trp Ala Phe Ile Pro Ile Ser
            195                 200                 205

Ala Gly Ala His Thr His Pro Pro Asp Glu
        210                 215

<210> SEQ ID NO 15
<211> LENGTH: 388
<212> TYPE: PRT
<213> ORGANISM: Artificial
<220> FEATURE:
<223> OTHER INFORMATION: human CSF-1R fragment delD4 (domains 1,2,3 and
      5 of the Extracellular Domain)

<400> SEQUENCE: 15

Ile Pro Val Ile Glu Pro Ser Val Pro Glu Leu Val Val Lys Pro Gly
1               5                   10                  15
```

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Tyr Pro Pro Glu Val Ser Val Ile Trp Thr Phe Ile Asn
        275                 280                 285

Gly Ser Gly Thr Leu Leu Cys Ala Ala Ser Gly Tyr Pro Gln Pro Asn
    290                 295                 300

Val Thr Trp Leu Gln Cys Ser Gly His Thr Asp Arg Cys Asp Glu Ala
305                 310                 315                 320

Gln Val Leu Gln Val Trp Asp Asp Pro Tyr Pro Glu Val Leu Ser Gln
                325                 330                 335

Glu Pro Phe His Lys Val Thr Val Gln Ser Leu Leu Thr Val Glu Thr
            340                 345                 350

Leu Glu His Asn Gln Thr Tyr Glu Cys Arg Ala His Asn Ser Val Gly
        355                 360                 365

Ser Gly Ser Trp Ala Phe Ile Pro Ile Ser Ala Gly Ala His Thr His
    370                 375                 380

Pro Pro Asp Glu
385

<210> SEQ ID NO 16
<211> LENGTH: 554
<212> TYPE: PRT
<213> ORGANISM: homo sapiens

```
<400> SEQUENCE: 16

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro
        355                 360                 365

Arg Val Gly Pro Val Arg Pro Thr Gly Gln Asp Trp Asn His Thr Pro
    370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415
```

```
Ser Thr Leu Ser Ala Gln Pro Gln Leu Ser Arg Ser His Ser Ser Gly
            420                 425                 430

Ser Val Leu Pro Leu Gly Glu Leu Glu Gly Arg Arg Ser Thr Arg Asp
            435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Phe Ser Pro Gln Leu Gln Glu Ser
            485                 490                 495

Val Phe His Leu Leu Val Pro Ser Val Ile Leu Val Leu Leu Ala Val
            500                 505                 510

Gly Gly Leu Leu Phe Tyr Arg Trp Arg Arg Ser His Gln Glu Pro
            515                 520                 525

Gln Arg Ala Asp Ser Pro Leu Glu Gln Pro Glu Gly Ser Pro Leu Thr
            530                 535                 540

Gln Asp Asp Arg Gln Val Glu Leu Pro Val
545                 550

<210> SEQ ID NO 17
<211> LENGTH: 242
<212> TYPE: PRT
<213> ORGANISM: homo sapiens

<400> SEQUENCE: 17

Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
            35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
            115                 120                 125

Val Gln Gln Gly Leu Thr Asp Val Glu Val Ser Pro Lys Val Glu Ser
130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
            195                 200                 205

Ala Thr Gln Leu Tyr Pro Pro Pro Pro Trp Ser Pro Ser Ser Pro Pro
210                 215                 220

His Ser Thr Gly Ser Val Arg Pro Val Arg Ala Gln Gly Glu Gly Leu
```

-continued 225 230 235 240

Leu Pro

<210> SEQ ID NO 18
<211> LENGTH: 290
<212> TYPE: PRT
<213> ORGANISM: homo sapiens

<400> SEQUENCE: 18

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 19
<211> LENGTH: 268
<212> TYPE: PRT
<213> ORGANISM: Homo Sapiens

<400> SEQUENCE: 19

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265

<210> SEQ ID NO 20
<211> LENGTH: 107
<212> TYPE: PRT
<213> ORGANISM: Homo sapiens

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 21
<211> LENGTH: 329
<212> TYPE: PRT
<213> ORGANISM: Homo sapiens

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 22
<211> LENGTH: 329
<212> TYPE: PRT
<213> ORGANISM: Artificial
<220> FEATURE:
<223> OTHER INFORMATION: human heavy chain constant region derived from
      IgG1 mutated on L234A and L235A
```

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 23
<211> LENGTH: 326
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
             100                 105                 110

Glu Phe Leu Gly Gly Pro Ser Val Phe Leu Phe Pro Pro Lys Pro Lys
             115                 120                 125

Asp Thr Leu Met Ile Ser Arg Thr Pro Glu Val Thr Cys Val Val Val
         130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 24
<211> LENGTH: 326
<212> TYPE: PRT
<213> ORGANISM: Artificial
<220> FEATURE:
<223> OTHER INFORMATION: human heavy chain constant region derived from
      IgG4 mutated onS228P

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 25
<211> LENGTH: 120
<212> TYPE: PRT
<213> ORGANISM: Artificial
<220> FEATURE:
<223> OTHER INFORMATION: heavy chain variable domain, anti-CSF-1R
      antibody 1 of US8263079

<400> SEQUENCE: 25

Gln Asp Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95

Ala Arg Gly Asp Tyr Glu Val Asp Tyr Gly Met Asp Val Trp Gly Gln
            100                 105                 110

Gly Thr Thr Val Thr Val Ala Ser
        115                 120

<210> SEQ ID NO 26
<211> LENGTH: 107
<212> TYPE: PRT
<213> ORGANISM: Artificial
<220> FEATURE:
<223> OTHER INFORMATION: light chain variable domain, anti-CSF-1R
      antibody 1 of US8263079

<400> SEQUENCE: 26

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys
            100                 105

<210> SEQ ID NO 27
<211> LENGTH: 450
<212> TYPE: PRT
<213> ORGANISM: Artificial
<220> FEATURE:
<223> OTHER INFORMATION: heavy chain, anti-CSF-1R antibody 1 of
      US8263079

<400> SEQUENCE: 27

Gln Asp Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Glu Val Asp Tyr Gly Met Asp Val Trp Gly Gln
            100                 105                 110

Gly Thr Thr Val Thr Val Ala Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 28
<211> LENGTH: 214
<212> TYPE: PRT
<213> ORGANISM: Artificial
<220> FEATURE:
<223> OTHER INFORMATION: light chain, anti-CSF-1R antibody 1 of
      US8263079

<400> SEQUENCE: 28

Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Ala
                20                  25                  30
Leu Ala Trp Tyr Gln Gln Lys Pro Gly Lys Ala Pro Lys Leu Leu Ile
                35                  40                  45
```

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
210

<210> SEQ ID NO 29
<211> LENGTH: 450
<212> TYPE: PRT
<213> ORGANISM: Artificial
<220> FEATURE:
<223> OTHER INFORMATION: heavy chain of anti-PD-L1 antibody avelumab

<400> SEQUENCE: 29

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 30
<211> LENGTH: 216
<212> TYPE: PRT
<213> ORGANISM: Artificial
<220> FEATURE:
<223> OTHER INFORMATION: light chain of anti-PD-L1 antibody avelumab

<400> SEQUENCE: 30

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95
```

```
Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215
```

TREATMENT OF TUMORS WITH AN ANTI-CSF-1R ANTIBODY IN COMBINATION WITH AN ANTI-PD-L1 ANTIBODY AFTER FAILURE OF ANTI-PD-L1/PD1 TREATMENT

CROSS REFERENCE TO RELATED APPLICATIONS

This application is a continuation of International Patent Application No. PCT/EP2017/083696, filed Dec. 20, 2017, which claims priority to European Patent Application No. 16206066.9, filed Dec. 22, 2016, the disclosure of which are incorporated hereby reference in their entirety.

SEQUENCE LISTING

The instant application contains a Sequence Listing submitted via EFS-Web and hereby incorporated by reference in its entirety. Said ASCII copy, created on May 14, 2019 is named P34043-US-SequenceListing.txt, and is 70,751 bytes in size.

The current invention relates to the combination therapy of an anti-CSF-1R antibody (especially a CSF-1R dimerization inhibitor) in combination with an anti-PD-L1 antibody after disease progression on PD1/PD-L1 inhibitor treatment, corresponding pharmaceutical compositions or medicaments using such combination therapy.

BACKGROUND OF THE INVENTION

CSF-1R and CSF-1R Antibodies

The human CSF-1 receptor (CSF-1R; colony stimulating factor 1 receptor; synonyms: M-CSF receptor; Macrophage colony-stimulating factor 1 receptor, Fms proto-oncogene, c-fms) is known since 1986 (Coussens, L., et al., Nature 320 (1986) 277-280). CSF-1R is a growth factor and encoded by the c-fms proto-oncogene (reviewed e.g. in Roth, P., and Stanley, E. R., Curr. Top. Microbiol. Immunol. 181 (1992) 141-167).

CSF-1R is the receptor for CSF-1 (colony stimulating factor 1, also called M-CSF, macrophage colony-stimulating factor) and mediates the biological effects of this cytokine (Sherr, C. J., et al., Cell 41 (1985) 665-676). The cloning of the colony stimulating factor-1 receptor (CSF-1R) (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628). Recently a second ligand for CSF-1R termed interleukin-34 (IL-34) was identified (Lin, H., et al, Science 320 (2008) 807-811).

Currently two CSF-1R ligands that bind to the extracellular domain of CSF-1R are known. The first one is CSF-1 (colony stimulating factor 1, also called M-CSF, macrophage; SEQ ID NO: 28) and is found extracellularly as a disulfide-linked homodimer (Stanley, E. R. et al., Journal of Cellular Biochemistry 21 (1983) 151-159; Stanley, E. R. et al., Stem Cells 12 Suppl. 1 (1995) 15-24). The second one is IL-34 (Human IL-34; SEQ ID NO: 29) (Hume, D. A., et al, Blood 119 (2012) 1810-1820). The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley, E. R., et al., Mol. Reprod. Dev. 46 (1997)4-10).

The biologically active homodimer CSF-1 binds to the CSF-1R within the subdomains D1 to D3 of the extracellular domain of the CSF-1 receptor (CSF-1R-ECD). The CSF-1R-ECD comprises five immunoglobulin-like subdomains (designated D1 to D5). The subdomains D4 to D5 of the extracellular domain (CSF-1R-ECD) are not involved in the CSF-1 binding (Wang, Z., et al Molecular and Cellular Biology 13 (1993) 5348-5359). The subdomain D4 is involved in dimerization (Yeung, Y-G., et al Molecular & Cellular Proteomics 2 (2003) 1143-1155; Pixley, F. J., et al., Trends Cell Biol. 14 (2004) 628-638).

Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCy, and Cbl (Bourette, R. P. and Rohrschneider, L. R., Growth Factors 17 (2000) 155-166).

CSF-1R signaling has a physiological role in immune responses, in bone remodeling and in the reproductive system. The knockout animals for either CSF-1 (Pollard, J. W., Mol. Reprod. Dev. 46 (1997) 54-61) or CSF-1R (Dai, X. M., et al., Blood 99 (2002) 111-120) have been shown to have osteopetrotic, hematopoietic, tissue macrophage, and reproductive phenotypes consistent with a role for CSF-1R in the respective cell types.

Sherr, C. J., et al., Blood 73 (1989) 1786-1793 relates to some antibodies against CSF-1R that inhibit the CSF-1 activity. Ashmun, R. A., et al., Blood 73 (1989) 827-837 relates to CSF-1R antibodies. Lenda, D., et al., Journal of Immunology 170 (2003) 3254-3262 relates to reduced macrophage recruitment, proliferation, and activation in CSF-1-deficient mice results in decreased tubular apoptosis during renal inflammation. Kitaura, H., et al., Journal of Dental Research 87 (2008) 396-400 refers to an anti-CSF-1 antibody which inhibits orthodontic tooth movement. WO 2001/030381 mentions CSF-1 activity inhibitors including antisense nucleotides and antibodies while disclosing only CSF-1 antisense nucleotides. WO 2004/045532 relates to metastases and bone loss prevention and treatment of metastatic cancer by a CSF-1 antagonist disclosing as antagonist anti-CSF-1-antibodies only. WO 2005/046657 relates to the treatment of inflammatory bowel disease by anti-CSF-1-antibodies. US 2002/0141994 relates to inhibitors of colony stimulating factors. WO 2006/096489 relates to the treatment of rheumatoid arthritis by anti-CSF-1-antibodies. WO 2009/026303 and WO 2009/112245 relate to certain anti-CSF-1R antibodies binding to CSF-1R within the first three subdomains (D1 to D3) of the Extracellular Domain (CSF-1R-ECD). WO 2011/123381, WO 2011/140249, WO 2012/110360 relate to antibodies against CSF-1R. WO 2011/070024 relate to certain anti-CSF-1R antibodies binding to CSF-1R within the dimerization domain (D4 to D5).

WO 2013/132044, and WO 2015/036511 relate inter alia to the combination therapy of anti-CSF-1R antibodies with cancer immunotherapies.

It has now been found surprisingly that a combination therapy of anti-CSF1R antibodies and anti-PDL1 antibodies is highly effective for tumors with anti-PD-L1/PD1 axis treatment failure.

SUMMARY OF THE INVENTION

Combination of cancer immunotherapies to harness the amplifying cytotoxic T cells to fight cancer has become a major focus in the treatment of patients. CSF-1R blocking agents that eliminate T cell suppressive tumor-associated macrophages (TAM) in tumors, represent a novel player for combinatorial immunotherapies.

Surprisingly, we found that that a combination therapy of anti-CSF1R antibodies and anti-PDL1 antibodies is highly effective for tumors with prior treatment failure on or after anti-PD-L1/PD1 axis treatment.

One aspect of the invention is an antibody which binds to human CSF-1R, for use in
  a) the treatment of cancer in combination with an antagonistic PD-L1 antibody, wherein a prior treatment of the cancer with a PD-L1/PD1 inhibitor selected from the group of an antagonistic PD-L1 antibody or an antagonistic PD1 antibody failed,
  or
  b) the treatment of a patient suffering from a cancer with CSF-1R expressing macrophage infiltrate in combination with an antagonistic PD-L1 antibody, wherein a prior treatment of the patient with a PD-L1/PD1 inhibitor selected from the group of an antagonistic PD-L1 antibody or an antagonistic PD1 antibody failed.

In one embodiment of the invention CSF-1R antibody binds to domain D4 or D5 of the extracellular domain (ECD) of CSF-1R.

In one embodiment of the invention the anti-CSF-1R antibody comprises
  a heavy chain variable domain VH of SEQ ID NO: 1 and a light chain variable domain VL of SEQ ID NO:2.

In one embodiment of the invention the anti-CSF-1R antibody comprises
  a heavy chain variable domain VH of SEQ ID NO: 1 and a light chain variable domain VL of SEQ ID NO:2, and
  the antagonistic PD-L antibody comprises
    a) a heavy chain variable domain VH of SEQ ID NO:3 and a light chain variable domain VL of SEQ ID NO:4
    or b) a heavy chain variable domain VH of SEQ ID NO:5 and a light chain variable domain VL of SEQ ID NO:6.

In one embodiment of the invention the anti-CSF-1R antibody comprises
  a heavy chain variable domain VH of SEQ ID NO: 1 and a light chain variable domain VL of SEQ ID NO:2, and
  the antagonistic PD-L1 antibody comprises
  a heavy chain variable domain VH of SEQ ID NO:3 and a light chain variable domain VL of SEQ ID NO:4.

In one embodiment of the invention in the combination treatment the anti-CSF-1R antibody is emactuzumab and the antagonistic PD-L1 antibody is atezolizumab or durvalumab.

In one embodiment of the invention in the combination treatment the anti-CSF-1R antibody is emactuzumab and the antagonistic PD-L1 antibody is atezolizumab or durvalumab.

In one embodiment of the invention anti-CSF-1R antibody comprises
  a heavy chain variable domain VH of SEQ ID NO:25 and a light chain variable domain VL of SEQ ID NO:26, and
  the antagonistic PD-L1 antibody comprises
  a heavy chain variable domain VH of SEQ ID NO:5 and a light chain variable domain VL of SEQ ID NO:6.

In one embodiment of the invention the prior treatment which failed was a atezolizumab or durvalumab treatment.

In one embodiment of the invention the prior treatment which failed was a atezolizumab treatment In one embodiment of the invention the prior treatment which failed was a durvalumab treatment.

One embodiment of the invention is the described anti-CSF-1R antibody for use in one of the above treatments, wherein the combined therapy is for use in treating or delaying progression of an immune related disease such as tumor immunity.

One embodiment of the invention is the described anti-CSF-1R antibody for use in one of the above treatments, wherein the combined therapy is for use in stimulating an immune response or function, such as T cell activity.

DETAILED DESCRIPTION OF THE INVENTION

Figure 1:
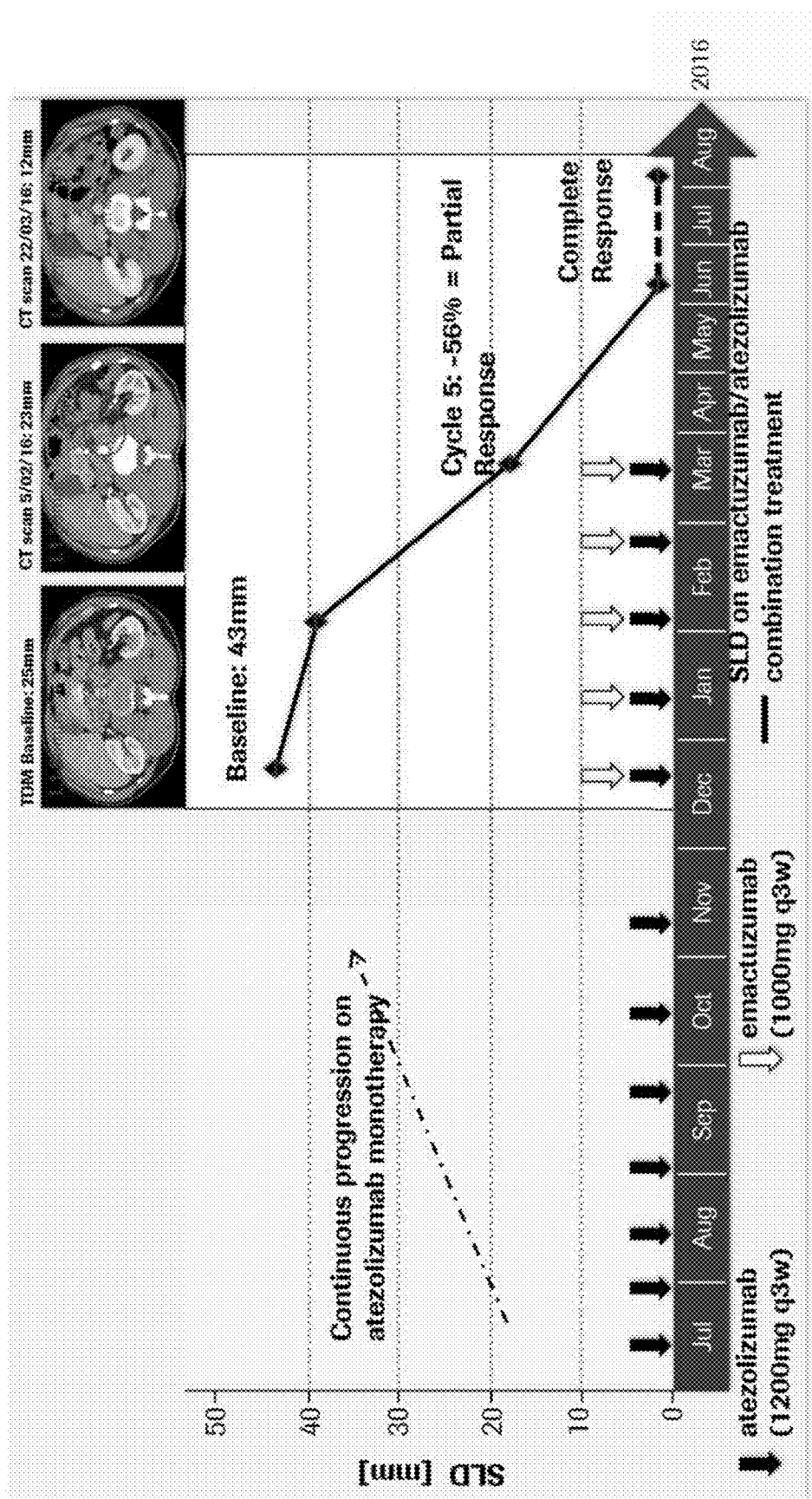
FIG. 1: Emactuzumab in combination with atezolizumab after treatment failure with atezolizumab monotherapy: Readout according to RECIST 1.1. criteria. Sum of the longest diameters (SLD) are shown A complete response could be determined in an UBC (urinary bladder cancer) patient previously progressive on atezolizumab monotherapy.

The term "wherein a prior treatment of the cancer . . . failed" as used herein refers to the situation wherein the cancer showed disease progression (e.g. when the Overall Response is a Progressive Disease (PD) according to the RECIST1.1 criteria for solid tumors) on (and/or after) the prior treatment. The term "wherein a prior treatment of the patient (suffering from a cancer) failed" as used herein refers to the situation wherein the patient (suffering from cancer) showed disease progression (e.g. a Progressive Disease (PD) according to the RECIST1.1 criteria for solid tumors) on (and/or after) the prior treatment. Such patients suffering from cancer or such cancers are non-responsive to the prior treatment.

A "tumor with CSF-1R expressing macrophage infiltrate" refers to a heterogeneous tumor comprising tumor cells and infiltrating CSF-1R-expressing tumor-associated macrophages (TAMs) or tissue resident macrophages.

According to these RECIST 1.1 criteria, tumor response for solid tumors (Eisenhauer E. A., et al. Eur. J. Cancer 45 (2009) 228-247) is categorized in dependency of the volume progression or regression of the tumors and lesions (e.g. measured via CT) into four levels: complete response (CR) or partial response (PR), stable disease (SD) and progressive disease (PD).

CSF-1R is a protein encoded by the CSF-1R gene. It controls the production, differentiation, and function of M2 macrophages, which, in turn, support tumor growth and metastasis formation and secrete immunosuppressive cytokines, leading to a poor prognosis in patients. Furthermore, presence of CSF-1R positive macrophages in several human cancers (such as ovarian and breast carcinoma) has been shown to correlate not only with increased vascular density but also worse clinical outcome. CSF-1R inhibitors, which selectively inhibit M2-like TAMs, have demonstrated activity in preclinical models (DeNardo, D. et al., Cancer Discovery 1 (2011) 54-67; Lin, E. et al., J. Exp. Med. 193 (2001) 727-740). Blockade of CSF-1R activity results in reduced recruitment of TAMs and, in combination with chemotherapy, a synergistic action results in reduced tumor growth and metastatic burden. Recent data have shown that in patients with PVNS and TGCT, overexpression of the CSF-1 is detected and is in part mediated by a translocation of the CSF-1R gene (West, R. B. et al., Proc. Natl. Acad. Sci. USA 3 (2006) 690-695). In breast cancer the presence of a CSF-1 response gene signature predicts risk of recurrence and metastasis (Beck, A. et al., Clin. Cancer Res. 3 (2009) 778-787).

Many tumors are characterized by a prominent immune cell infiltrate, including macrophages. Initially, the immune cells were thought to be part of a defense mechanism against the tumor, but recent data support the notion that several immune cell populations including macrophages may, in fact, promote tumor progression. Macrophages are characterized by their plasticity. Depending on the cytokine microenvironment, macrophages can exhibit so-called M1 or M2-subtypes. M2 macrophages are engaged in the suppression of tumor immunity. They also play an important role in tissue repair functions such as angiogenesis and tissue remodeling which are coopted by the tumor to support growth. In contrast to tumor promoting M2 macrophages, MI macrophages exhibit antitumor activity via the secretion of inflammatory cytokines and their engagement in antigen presentation and phagocytosis (Mantovani, A. et al., Curr. Opin. Immunol. 2 (2010) 231-237).

By secreting various cytokines such as colony stimulating factor 1 (CSF-1) and IL-10, tumor cells are able to recruit and shape macrophages into the M2-subtype, whereas cytokines such as granulocyte macrophage colony stimulating factor (GM-CSF), IFN-gamma program macrophages towards the M1 subtype. Using immunohistochemistry, it is possible to distinguish between a macrophage subpopulation co-expressing CD68 and CD163, which is likely to be enriched for M2 Macrophages, and a subset showing the CD68+/MHC II+, or CD68+/CD80+ immunophenotype, likely to include MI macrophages. Cell shape, size, and spatial distribution of CD68 and CD163 positive macrophages is consistent with published hypotheses on a tumor-promoting role of M2 macrophages, for example by their preferential location in tumor intersecting stroma, and vital tumor areas. In contrast, CD68+/MHC class II+ macrophages are ubiquitously found. Their hypothetical role in phagocytosis is reflected by clusters of the CD68+/MHC class II+, but CD163-immunophenotype near apoptotic cells and necrotic tumor areas.

The subtype and marker expression of different macrophage subpopulations is linked with their functional state. M2 macrophages can support tumorigenesis by:
 a) enhancing angiogenesis via the secretion of angiogenic factors such as VEGF or bFGF,
 b) supporting metastasis formation via secretion of matrix metalloproteinases (MMPs), growth factors and migratory factors guiding the tumor cells to the blood stream and setting up the metastatic niche (Wyckoff, J. et al., Cancer Res. 67 (2007) 2649-2656),
 c) playing a role in building an immunosuppressive milieu by secreting immunosuppressive cytokines such as IL-4, 11-13, IL-Ira and IL-10, which in turn regulate T regulatory cell function. Conversely CD4 positive T cells have been shown to enhance the activity of tumor promoting macrophages in preclinical models (Mantovani, A. et al., Eur. J. Cancer 40 (2004) 1660-1667; DeNardo, D. et al., Cancer Cell 16 (2009) 91-102).

Accordingly, in several types of cancer (e.g. breast, ovarian, Hodgkin's lymphoma) the prevalence of M2 subtype tumor associated macrophages (TAMs) has been associated with poor prognosis (Bingle, L. et al., J. Pathol. 3 (2002) 254-265; Orre, M., and Rogers, P. A., Gynecol. Oncol. 1 (1999) 47-50; Steidl, C. et al., N. Engl. J. Med. 10 (2010) 875-885). Recent data show a correlation of CD163 positive macrophage infiltrate in tumors and tumor grade (Kawamura, K. et al., Pathol. Int. 59 (2009) 300-305). TAMs isolated from patient tumors had a tolerant phenotype and were not cytotoxic to tumor cells (Mantovani, A. et al., Eur. J. Cancer 40 (2004) 1660-1667). However, infiltration of TAMs in the presence of cytotoxic T cells correlates with improved survival in non small cell lung cancer and hence reflects a more prominent MI macrophage infiltrate in this tumor type (Kawai, O. et al., Cancer 6 (2008) 1387-1395).

CSF-1R belongs to the class III subfamily of receptor tyrosine kinases and is encoded by the c-fms proto-oncogene. Binding of CSF-1 or IL-34 induces receptor dimerization, followed by autophosphorylation and activation of downstream signaling cascades. Activation of CSF-1R regulates the survival, proliferation and differentiation of monocytes and macrophages (Xiong, Y. et al., J. Biol. Chem. 286 (2011) 952-960).

In addition to cells of the monocytic lineage and osteoclasts, which derive from the same hematopoietic precursor as the macrophage, CSF-1R/c-fms has also been found to be expressed by several human epithelial cancers such as ovarian and breast cancer and in leiomyosarcoma and TGCT/PVNS, albeit at lower expression levels compared to macrophages. As with TGCT/PVNS, elevated levels of CSF-1, the ligand for CSF-1R, in serum as well as ascites of ovarian cancer patients have been correlated with poor prognosis (Scholl, S. et al., Br. J. Cancer 62 (1994) 342-346; Price, F. et al., Am. J. Obstet. Gynecol. 168 (1993) 520-527). Furthermore, a constitutively active mutant form of CSF1R is able to transform NIH3T3 cells, one of the properties of an oncogene (Chambers, S., Future Oncol 5 (2009) 1429-1440).

As surrogate for the tumor associated macrophages (TAMs) the precursor human CD14+CD16+(positive) monocytes in blood serum are measured, as the recovery of this blood monocytes correlates with the subsequent recovery of the tumor associated macrophages (TAMs). The term "after a significant recovery of CD14+CD16+ positive monocytes in blood serum (in one embodiment the recovery is more than 60%, in one embodiment more than 80%)" as used herein refers to the a reproduction of CD14+CD16+ positive monocytes in blood serum after they have been depleted first by the anti-CSFR antibody treatment and after, when there is a time when no more anti-CSFR antibody treatment is administered (anti-CSF-1R drug holiday) the cell population of CD14+CD16+ positive monocytes in blood serum grows again towards more than 50% percent (in one embodiment the recovery is more than 60%, in one embodiment more than 80%) of the value this population had before anti-CSFR antibody treatment. A pharmacodynamic model can been fitted to the human CD14+CD16+ monocyte data. Based on preliminary population analysis, a dose of 750 mg administered Q6W shows significant recovery of CD14+CD16+ monocytes.

In one embodiment different treatment schedules can be applied. E.g. as the first treatment with the anti-CSF-1R antibody leads to a strong reduction/depletion of tumor associated macrophages (TAMs) and their precursor human CD14+CD16+(positive) monocytes in blood serum, the length of an treatment cycle can be chosen to provide enough time that a significant recovery of the of this human CD14+CD16+(positive) monocytes blood monocytes correlating with the subsequent recovery of the tumor associated macrophages (TAMs), so that the TAMs are not continuously depleted. And the combination treatment with the PD-L1/PD1 inhibitor selected from the group of an antagonistic PD-L1 antibody or an antagonistic PD1 antibody can exert its strong synergistic anti-tumor efficacy.

The human CSF-1R (CSF-1 receptor; synonyms: M-CSF receptor; Macrophage colony-stimulating factor 1 receptor, Fms proto-oncogene, c-fms, SEQ ID NO: 24)) is known since 1986 (Coussens, L., et al., Nature 320 (1986) 277-280). CSF-1R is a growth factor and encoded by the c-fms proto-oncogene (reviewed e.g. in Roth. P. and Stanley, E. R., Curr. Top. Microbiol. Immunol. 181 (1992) 141-167).

CSF-1R is the receptor for the CSF-1R ligands CSF-1 (macrophage colony stimulating factor, also called M-CSF) (SEQ ID No.: 28) and IL-34 (SEQ ID No.: 29) and mediates the biological effects of these cytokines (Sherr, C. J., et al., Cell 41 (1985) 665-676; Lin. H., et al., Science 320 (2008) 807-811). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cbl and thereby regulates receptor down regulation (Lee, P. S., et al., Embo J. 18 (1999) 3616-3628).

CSF-1R is a single chain, transmembrane receptor tyrosine kinase (RTK) and a member of the family of immunoglobulin (Ig) motif containing RTKs characterized by 5 repeated Ig-like subdomains D1-D5 in the extracellular domain (ECD) of the receptor (Wang. Z., et al Molecular and Cellular Biology 13 (1993) 5348-5359). The human CSF-1R Extracellular Domain (CSF-1R-ECD) (SEQ ID NO: 12) comprises all five extracellular Ig-like subdomains D1-D5. The human CSF-1R fragment D1-D3 (SEQ ID NO: 13) comprises the respective subdomains D1-D3. The sequences are listed without the signal peptide. The human CSF-1R fragment D4-D5 (SEQ ID NO: 14) comprises the respective subdomains D4-D5. The human CSF-1R fragment delD4 (SEQ ID NO: 15) comprises the ECD subdomains D1, D2, D3 and D5.

Currently two CSF-1R ligands that bind to the extracellular domain of CSF-1R are known. The first one is CSF-1 (colony stimulating factor 1, also called M-CSF, macrophage; human CSF-1, SEQ ID NO: 16) and is found extracellularly as a disulfide-linked homodimer (Stanley, E. R et al., Journal of Cellular Biochemistry 21 (1983) 151-159; Stanley, E. R. et al., Stem Cells 12 Suppl. 1 (1995) 15-24). The second one is IL-34 (human IL-34; SEQ ID NO: 17) (Hume, D. A., et al, Blood 119 (2012) 1810-1820). Thus in one embodiment the term "CSF-1R ligand" refers to human CSF-1 (SEQ ID NO: 16) and/or human IL-34 (SEQ ID NO: 17).

For experiments often the active 149 amino acid (aa) fragment of human CSF-1 (aa 33-181 of SEQ ID NO: 16) is used. This active 149 aa fragment of human CSF-1 (aa 33-181 of SEQ ID NO: 16) is contained in all 3 major forms of CSF-1 and is sufficient to mediate binding to CSF-1R (Hume, D. A., et al, Blood 119 (2012) 1810-1820).

The main biological effects of CSF-1R signaling are the differentiation, proliferation, migration, and survival of hematopoietic precursor cells to the macrophage lineage (including osteoclast). Activation of CSF-1R is mediated by its CSF-1R ligands, CSF-1 (M-CSF) and IL-34. Binding of CSF-1 (M-CSF) to CSF-1R induces the formation of homodimers and activation of the kinase by tyrosine phosphorylation (Li, W. et al, EMBO Journal. 10 (1991) 277-288; Stanley, E. R., et al., Mol. Reprod. Dev. 46 (1997) 4-10).

As used herein, "binding to human CSF-1R" or "specifically binding to human CSF-1R" or "which binds to human CSF-1R" or "anti-CSF-1R antibody" refers to an antibody specifically binding to the human CSF-1R antigen with a binding affinity of KD-value of $1.0 \times 10^{-8}$ mol/l or lower, in one embodiment of a KD-value of $1.0 \times 10^{-9}$ mol/l or lower. The binding affinity is determined with a standard binding assay, such as surface plasmon resonance technique (BIAcore®, GE-Healthcare Uppsala, Sweden). Thus an "antibody binding to human CSF-1R" as used herein refers to an antibody specifically binding to the human CSF-1R antigen with a binding affinity of KD $1.0 \times 10$ mol/l or lower (in one embodiment $1.0 \times 10$ mol/l-$1.0 \times 10^{-13}$ mol/l), in on embodiment of a KD $1.0 \times 10^{-9}$ mol/l or lower (in one embodiment $1.0 \times 10^{-9}$ mol/l-$1.0 \times 10^{-13}$ mol/l).

In one embodiment the antibody which binds to human CSF-1R used in the combination therapy described herein is selected from the group consisting of hMab 2F11-c11, hMab 2F11-d8, hMab 2F11-e7, hMab 2F11-f12, and hMab 2F11-g1. These antibodies are described in WO 2011/070024.

In one embodiment the antibody which binds to human CSF-1R used in the combination therapy described herein is emactuzumab and is characterized in comprising the following VH and VL sequences as described herein:

TABLE 1

| anti-CSF-1R antibody | amino acid sequence of the heavy chain variable domain VH, SEQ ID NO: | amino acid sequence of the light chain variable domain VL, SEQ ID NO: |
| --- | --- | --- |
| emactuzumab | 1 | 2 |

These anti-CSF-1R antibodies described in the invention bind to the extracellular domain of human CSF-1R. In one preferred embodiment the anti-CSF-1R antibody binds to the membrane proximal domains D4 and D5 which constitute the receptor dimerization interface. So an antibody which binds to CSF-1R and binds to domains D4 and D5 of the extracellular domain (ECD) of human CSF-1R is characterized in that the anti-CSF1R antibody does not bind to the domains D1, D2 and D3 of the extracellular domain (ECD) of human CSF-1R.

In another embodiment the anti-CSF1R antibody binds to the domains DI to D3. In one embodiment, the antibody which binds to human CSF-1R used in the combination therapy described herein is disclosed in WO 2009/026303, WO 2009/112245, WO 2011/123381 and U.S. Pat. No. 8,263,079, WO 2011/140249, and WO 2012/110360, (which all are incorporated by reference).

The anti-CSF-1R antibodies described in the invention block CSF-1, IL-34 mediated as well as ligand-independent activation of the receptor resulting in induction of apoptosis of M2-like macrophages differentiated in vitro in the presence of CSF-1 while sparing the MI-like GM-CSF differentiated macrophages. In human breast cancer tissue, M2 (CD68+/CD163+) macrophages and CSF 1R-expressing macrophages are co-localized.

PD-1/PD-L1/PD-L2 Pathway:

An important negative co-stimulatory signal regulating T cell activation is provided by programmed death-1 receptor (PD-1)(CD279), and its ligand binding partners PD-L1 (B7-H1, CD274; SEQ ID NO: 18) and PD-L2 (B7-DC, CD273). The negative regulatory role of PD-1 was revealed by PD-1 knock outs (Pdcd1−/−), which are prone to autoimmunity. Nishimura et al., Immunity 11: 141-51 (1999): Nishimura et al., Science 291: 319-22 (2001). PD-1 is related to CD28 and CTLA-4, but lacks the membrane proximal cysteine that allows homodimerization. The cytoplasmic domain of PD-1 contains an immunoreceptor tyrosine-based inhibition motif (ITIM, V/IxYxxL/V). PD-1 only binds to PD-L1 and PD-L2. Freeman et al., J. Exp. Med. 192: 1-9 (2000); Dong et al., Nature Med. 5: 1365-1369 (1999); Latchman et al., Nature Immunol. 2: 261-268 (2001); Tseng et al., J. Exp. Med. 193: 839-846 (2001).

PD-1 can be expressed on T cells, B cells, natural killer T cells, activated monocytes and dendritic cells (DCs). PD-1 is expressed by activated, but not by unstimulated human CD4+ and CD8+ T cells, B cells and myeloid cells. This stands in contrast to the more restricted expression of CD28 and CTLA-4. Nishimura et al., Int. Immunol. 8: 773-80 (1996): Boettler et al., J. Virol. 80: 3532-40 (2006). There are at least 4 variants of PD-1 that have been cloned from activated human T cells, including transcripts lacking (i) exon 2, (ii) exon 3, (iii) exons 2 and 3 or (iv) exons 2 through 4. Nielsen et al., Cell. Immunol. 235: 109-16 (2005). With the exception of PD-1 Δex3, all variants are expressed at similar levels as full length PD-1 in resting peripheral blood mononuclear cells (PBMCs). Expression of all variants is significantly induced upon activation of human T cells with anti-CD3 and anti-CD28. The PD-1 Δex3 variants lacks a transmembrane domain, and resembles soluble CTLA-4, which plays an important role in autoimmunity. Ueda et al., Nature 423: 506-11 (2003). This variant is enriched in the synovial fluid and sera of patients with rheumatoid arthritis. Wan et al., J. Immunol. 177: 8844-50 (2006).

The two PD-1 ligands differ in their expression patterns. PD-L1 is constitutively expressed on mouse T and B cells, CDs, macrophages, mesenchymal stem cells and bone marrow-derived mast cells. Yamazaki et al., J. Immunol. 169: 5538-45 (2002). PD-L1 is expressed on a wide range of nonhematopoietic cells (e.g., cornea, lung, vascular epithelium, liver nonparenchymal cells, mesenchymal stem cells, pancreatic islets, placental synctiotrophoblasts, keratinocytes, etc.) [Keir et al., Annu. Rev. Immunol. 26: 677-704 (2008)], and is upregulated on a number of cell types after activation. Both type I and type II interferons IFN's) upregulate PD-L. Eppihimer et al., Microcirculation 9: 133-45 (2002); Schreiner et al., J. Neuroimmunol. 155: 172-82 (2004). PD-L1 expression in cell lines is decreased when MyD88, TRAF6 and MEK are inhibited. Liu et al., Blood 110: 296-304 (2007). JAK2 has also been implicated in PD-L1 induction. Lee et al., FEBS Lett. 580: 755-62 (2006); Liu et al., Blood 110: 296-304 (2007). Loss or inhibition of phosphatase and tensin homolog (PTEN), a cellular phosphatase that modified phosphatidylinositol 3-kinase (PI3K) and Akt signaling, increased post-transcriptional PD-L1 expression in cancers. Parsa et al., Nat. Med. 13: 84-88 (2007).

PD-L2 expression is more restricted than PD-L. PD-L2 is inducibly expressed on DCs, macrophages, and bone marrow-derived mast cells. PD-L2 is also expressed on about half to two-thirds of resting peritoneal B1 cells, but not on conventional B2 B cells. Zhong et al., Eur. J. Immunol. 37: 2405-10 (2007). PD-L2+B1 cells bind phosphatidylcholine and may be important for innate immune responses against bacterial antigens. Induction of PD-L2 by IFN-gamma is partially dependent upon NF-κB. Liang et al., Eur. J. Immunol. 33: 2706-16 (2003). PD-L2 can also be induced on monocytes and macrophages by GM-CF, IL-4 and IFN-gamma. Yamazaki et al., J. Immunol. 169: 5538-45 (2002); Loke et al., PNAS 100:5336-41 (2003).

PD-1 signaling typically has a greater effect on cytokine production than on cellular proliferation, with significant effects on IFN-gamma, TNF-alpha and IL-2 production. PD-1 mediated inhibitory signaling also depends on the strength of the TCR signaling, with greater inhibition delivered at low levels of TCR stimulation. This reduction can be overcome by costimulation through CD28 [Freeman et al., J. Exp. Med. 192: 1027-34 (2000)] or the presence of IL-2 [Carter et al., Eur. J. Immunol. 32: 634-43 (2002)].

Evidence is mounting that signaling through PD-L1 and PD-L2 may be bidirectional. That is, in addition to modifying TCR or BCR signaling, signaling may also be delivered back to the cells expressing PD-L1 and PD-L2. While treatment of dendritic cells with a naturally human anti-PD-L2 antibody isolated from a patient with Waldenstrom's macroglobulinemia was not found to upregulate MHC II or B7 costimulatory molecules, such cells did produce greater amount of proinflammatory cytokines, particularly TNF-alpha and IL-6, and stimulated T cell proliferation. Nguyen et al., J. Exp. Med. 196: 1393-98 (2002). Treatment of mice with this antibody also (1) enhanced resistance to transplanted b16 melanoma and rapidly induced tumor-specific CTL. Radhakrishnan et al., J. Immunol. 170: 1830-38 (2003): Radhakrishnan et al., Cancer Res. 64: 4965-72 (2004): Heckman et al., Eur. J. Immunol. 37: 1827-35 (2007); (2) blocked development of airway inflammatory disease in a mouse model of allergic asthma. Radhakrishnan et al., J. Immunol. 173: 1360-65 (2004); Radhakrishnan et al., J. Allergy Clin. Immunol. 116: 668-74 (2005).

Further evidence of reverse signaling into dendritic cells ("DC's") results from studies of bone marrow derived DC's cultured with soluble PD-1 (PD-1 EC domain fused to Ig constant region—"s-PD-1"). Kuipers et al., Eur. J. Immunol. 36: 2472-82 (2006). This sPD-1 inhibited DC activation and increased IL-10 production, in a manner reversible through administration of anti-PD-1.

Additionally, several studies show a receptor for PD-L1 or PD-L2 that is independent of PD-1. B7.1 has already been identified as a binding partner for PD-L1. Butte et al., Immunity 27: 111-22 (2007). Chemical crosslinking studies suggest that PD-L1 and B7.1 can interact through their IgV-like domains. B7.1:PD-L1 interactions can induce an inhibitory signal into T cells. Ligation of PD-L1 on CD4+ T cells by B7.1 or ligation of B7.1 on CD4+ T cells by PD-L1 delivers an inhibitory signal. T cells lacking CD28 and CTLA-4 show decreased proliferation and cytokine production when stimulated by anti-CD3 plus B7.1 coated beads. In T cells lacking all the receptors for B7.1 (i.e., CD28, CTLA-4 and PD-L1), T cell proliferation and cytokine production were no longer inhibited by anti-CD3 plus B7.1 coated beads. This indicates that B7.1 acts specifically through PD-L on the T-cell in the absence of CD28 and CTLA-4. Similarly, T cells lacking PD-1 showed decreased proliferation and cytokine production when stimulated in the presence of anti-CD3 plus PD-L1 coated beads, demonstrating the inhibitory effect of PD-L1 ligation on B7.1 on T cells. When T cells lacking all known receptors for PD-L1 (i.e., no PD-1 and B7.1), T cell proliferation was no longer impaired by anti-CD3 plus PD-L1 coated beads. Thus, PD-L1 can exert an inhibitory effect on T cells either through B7.1 or PD-1.

The direct interaction between B7.1 and PD-L suggests that the current understanding of costimulation is incomplete, and underscores the significance to the expression of these molecules on T cells. Studies of PD-L1−/− T cells indicate that PD-L1 on T cells can downregulate T cell cytokine production. Latchman et al., Proc. Natl. Acad. Sci. USA 101: 10691-96 (2004). Because both PD-L1 and B7.1 are expressed on T cells, B cells, DCs and macrophages, there is the potential for directional interactions between B7.1 and PD-L1 on these cells types. Additionally, PD-L1 on non-hematopoietic cells may interact with B7.1 as well as PD-1 on T cells, raising the question of whether PD-L1 is involved in their regulation. One possible explanation for the inhibitory effect of B7.1:PD-L1 interaction is that T cell PD-L1 may trap or segregate away APC B7.1 from interaction with CD28.

As a result, the antagonism of signaling through PD-L1, including blocking PD-L1 from interacting with either PD-1. B7.1 or both, thereby preventing PD-L1 from sending a negative co-stimulatory signal to T-cells and other antigen presenting cells is likely to enhance immunity in response to infection (e.g., acute and chronic) and tumor immunity. An exemplary PD-L1 antagonist is the anti-PD-L1 antibody atezolizumab.

In another embodiment, the anti-PD-L1/PD1 interaction can blocked by antagonist anti-PD-1 like the anti-PD1 antibodies pembrolizumab or nivolumab.

The term "human PD-L1" refers to the human protein PD-L1 (SEQ ID NO: 18, PD-1 signaling typically). As used herein, "binding to human PD-L1" or "specifically binding to human PD-L" or "which binds to human PD-L1" or "anti-PD-L1 antibody" or "antagonistic anti-PD-L1" refers to an antibody specifically binding to the human PD-L1 antigen with a binding affinity of KD-value of $1.0 \times 10^{-8}$ mol/l or lower, in one embodiment of a KD-value of $1.0 \times 10^{-9}$ mol/l or lower. The binding affinity is determined with a standard binding assay, such as surface plasmon resonance technique (BIAcore®, GE-Healthcare Uppsala. Sweden). Thus an "antibody binding to human PD-L1" as used herein refers to an antibody specifically binding to the human PD-L1 antigen with a binding affinity of KD $1.0 \times 10^{-8}$ mol/l or lower (in one embodiment $1.0 \times 10^{-8}$ mol/l-$1.0 \times 10^{-13}$ mol/l), in on embodiment of a KD $1.0 \times 10^{-9}$ mol/l or lower (in one embodiment $1.0 \times 10^{-9}$ mol/l-$1.0 \times 10^{-13}$ mol/l).

The term "human PD1" refers to the human protein PD1 (SEQ ID NO: 19, PD-1 signaling typically). As used herein, "binding to human PD1" or "specifically binding to human PD1" or "which binds to human PD1" or "anti-PD1 antibody" or "antagonistic anti-PD1" refers to an antibody specifically binding to the human PD1 antigen with a binding affinity of KD-value of $1.0 \times 10^{-8}$ mol/l or lower, in one embodiment of a KD-value of $1.0 \times 10^{-9}$ mol/l or lower. The binding affinity is determined with a standard binding assay, such as surface plasmon resonance technique (BIAcore®, GE-Healthcare Uppsala, Sweden). Thus an "antibody binding to human PD1" as used herein refers to an antibody specifically binding to the human PD1 antigen with a binding affinity of KD $1.0 \times 10^{-8}$ mol/or lower (in one embodiment $1.0 \times 10^{-8}$ mol/l-$1.0 \times 10^{-13}$ mol/l), in on embodiment of a KD $1.0 \times 10^{-9}$ mol/l or lower (in one embodiment $1.0 \times 10^{-9}$ mol/l-$1.0 \times 10^{-13}$ mol/l).

In one embodiment the antibody which binds to human PD-L1 used in the combination therapy described herein is atezolizumab or durvalumab and is characterized in comprising the following VH and VL sequences as described herein:

TABLE 2

| anti-PD-L1 antibody | amino acid sequence of the heavy chain variable domain VH, SEQ ID NO: | amino acid sequence of the light chain variable domain VL, SEQ ID NO: |
| --- | --- | --- |
| atezolizumab | 3 | 4 |
| durvalumab | 5 | 6 |

In one preferred embodiment of the invention the antibody which binds to human CSF-1R used in the combination therapy comprises
 a heavy chain variable domain VH of SEQ ID NO: 1 and
  a light chain variable domain VL of SEQ ID NO:2, and
the antibody which binds to human PD-L1 used in the combination therapy comprises
 a heavy chain variable domain VH of SEQ ID NO:3 and
  a light chain variable domain VL of SEQ ID NO:4, or
 a heavy chain variable domain VH of SEQ ID NO:5 and
  a light chain variable domain VL of SEQ ID NO:6.

In another preferred embodiment of the invention the antibody which binds to human CSF-1R used in the combination therapy described herein comprises
 a heavy chain variable domain VH of SEQ ID NO: 1 and
  a light chain variable domain VL of SEQ ID NO:2, and
the antibody which binds to human PD-L1 used in the combination therapy comprises
 a heavy chain variable domain VH of SEQ ID NO:3 and
  a light chain variable domain VL of SEQ ID NO:4.

In another preferred embodiment of the invention the antibody which binds to human CSF-1R used in the combination therapy described herein is emactuzumab, and the antibody which binds to human PD-L1 used in the combination therapy is atezolizumab, or durvalumab.

In another preferred embodiment of the invention the antibody which binds to human CSF-1R used in the combination therapy described herein is emactuzumab, and the antibody which binds to human PD-L1 used in the combination therapy is atezolizumab.

In one preferred embodiment of the invention the antibody which binds to human CSF-1R used in the combination therapy described herein comprises
 a heavy chain variable domain VH of SEQ ID NO: 1 and
  a light chain variable domain VL of SEQ ID NO:2, and
the antibody which binds to human PD-L1 used in the combination therapy comprises
 a heavy chain variable domain VH of SEQ ID NO:3 and
  a light chain variable domain VL of SEQ ID NO:4, or
 a heavy chain variable domain VH of SEQ ID NO:5 and
  a light chain variable domain VL of SEQ ID NO:6, and the prior treatment of the cancer which failed was with an antagonistic PD-L1 antibody.

In one preferred embodiment of the invention the antibody which binds to human CSF-1R used in the combination therapy described herein is characterized in comprising
   a heavy chain variable domain VH of SEQ ID NO: 1 and
      a light chain variable domain VL of SEQ ID NO:2, and
the antibody which binds to human PD-L1 used in the combination therapy is characterized in comprising
   a heavy chain variable domain VH of SEQ ID NO:3 and
      a light chain variable domain VL of SEQ ID NO:4, or
   a heavy chain variable domain VH of SEQ ID NO:5 and
      a light chain variable domain VL of SEQ ID NO:6,
and the prior treatment of the cancer which failed, was with an antagonistic PD1 antibody.

In another preferred embodiment of the invention the antibody which binds to human CSF-1R used in the combination therapy described herein is characterized in comprising
   a heavy chain variable domain VH of SEQ ID NO: 1 and
      a light chain variable domain VL of SEQ ID NO:2, and
the antibody which binds to human PD-L1 used in the combination therapy is characterized in comprising
   a heavy chain variable domain VH of SEQ ID NO:3 and
      a light chain variable domain VL of SEQ ID NO:4:
and the prior treatment of the cancer which failed was with an antagonistic PD-L1 antibody (in one embodiment with atezolizumab).

In another preferred embodiment of the invention the antibody which binds to human CSF-1R used in the combination therapy described herein is characterized in comprising
   a heavy chain variable domain VH of SEQ ID NO: 1 and
      a light chain variable domain VL of SEQ ID NO:2, and
the antibody which binds to human PD-L used in the combination therapy is characterized in comprising
   a heavy chain variable domain VH of SEQ ID NO:3 and
      a light chain variable domain VL of SEQ ID NO:4:
and the prior treatment of the cancer which failed, was with an antagonistic PD1 antibody.

In another preferred embodiment of the invention the antibody which binds to human CSF-1R used in the combination therapy described herein is emactuzumab, and the antibody which binds to human PD-L1 used in the combination therapy is atezolizumab, or durvalumab: and the prior treatment of the cancer which failed was with an antagonistic PD-L1 antibody.

In another preferred embodiment of the invention the antibody which binds to human CSF-1R used in the combination therapy described herein is emactuzumab, and the antibody which binds to human PD-L1 used in the combination therapy is atezolizumab; and the prior treatment of the cancer which failed was with an antagonistic PD-L antibody (in one embodiment with atezolizumab or durvalumab).

In another preferred embodiment of the invention the antibody which binds to human CSF-1R used in the combination therapy described herein is emactuzumab, and the antibody which binds to human PD-L1 used in the combination therapy is atezolizumab, or durvalumab; and the prior treatment of the cancer which failed was with an antagonistic PD1 antibody.

In another preferred embodiment of the invention the antibody which binds to human CSF-1R used in the combination therapy described herein is emactuzumab, and the antibody which binds to human PD-L1 used in the combination therapy is atezolizumab: and the prior treatment of the cancer which failed was with an antagonistic PD1 antibody (in one embodiment with pembrolizumab or nivolumab).

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents.

The "variable domain" (light chain variable domain VL, heavy chain variable domain VH) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service. National Institutes of Health. Bethesda, Md. (1991) and/or those residues from a "hypervariable loop". The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy alpha-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boackle, R. J., et al., Nature 282 (1979) 742-743; Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virology 75 (2001) 12161-12168; Morgan, A., et al., Immunology 86 (1995) 319-324; EP 0 307 434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

In one embodiment the antibody according to the invention comprises an Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (in one embodiment with a mutation on L234A+L235A), a Fc part from human IgG4 subclass or a mutated Fc part from human IgG4 subclass (in one embodiment with a mutation on S228P). In one preferred embodiment the human heavy chain constant region of human IgG1 subclass, in another preferred embodiment the human heavy chain constant region is of human IgG1 subclass with mutations L234A, L235A and P329, in another preferred embodiment the human heavy chain constant region is of human IgG4 subclass, and in another preferred embodiment the human heavy chain constant region is of human IgG4 subclass with mutation S228P. In one embodiment said antibodies have reduced or minimal effector function. In one embodiment the minimal effector function results from an effectorless Fc mutation. In one embodiment the effectorless Fc mutation is L234A/L235A or L234A/L235A/P329G or N297A or D265A/N297A. In one embodiment the effectorless Fc mutation is selected for each of the antibodies independently of each other from the group comprising (consisting of) L234A/L235A, L234A/L235A/P329G, N297A and D265A/N297A.

In one embodiment the antibodies described herein are of human IgG class (i.e. of IgG1, IgG2, IgG3 or IgG4 subclass).

In a preferred embodiment the antibodies described herein are of human IgG1 subclass or of human IgG4 subclass. In one embodiment the described herein are of human IgG1 subclass. In one embodiment the antibodies described herein are of human IgG4 subclass.

In one embodiment the antibody described herein is characterized in that the constant chains are of human origin. Such constant chains are well known in the state of the art and e.g. described by Kabat, E. A., (see e.g. Johnson, G. and Wu, T. T., Nucleic Acids Res. 28 (2000) 214-218). For example, a useful human heavy chain constant region comprises an amino acid sequence of SEQ ID NO: 21. For example, a useful human light chain constant region comprises an amino acid sequence of a kappa-light chain constant region of SEQ ID NO: 20.

The invention comprises a method for the treatment of a patient in need of therapy, characterized by administering to the patient a therapeutically effective amount of an antibody according to the invention.

The invention comprises the use of an antibody according to the invention for the described therapy.

One embodiment of the invention are the CSF-1R antibodies described herein in for use in the treatment of cancer in combination with an antagonistic PD-L1 antibody as described herein.

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. In one preferred embodiment such cancer is a breast cancer, colorectal cancer, melanoma, head and neck cancer, lung cancer or prostate cancer. In one preferred embodiment such cancer is a breast cancer, ovarian cancer, cervical cancer, lung cancer or prostate cancer. In another preferred embodiment such cancer is breast cancer, lung cancer, colon cancer, ovarian cancer, melanoma cancer, bladder cancer, renal cancer, kidney cancer, liver cancer, head and neck cancer, colorectal cancer, pancreatic cancer, gastric carcinoma cancer, esophageal cancer, mesothelioma, prostate cancer, leukemia, lymphoma, myelomas. In one preferred embodiment such cancers are further characterized by CSF-1 or CSF-1R expression or overexpression. One further embodiment the invention are the CSF-1R antibodies of the present invention for use in the simultaneous treatment of primary tumors and new metastases. Thus another embodiment of the invention are the CSF-1R antibodies of the present invention for use in the treatment of periodontitis, histiocytosis X, osteoporosis, Paget's disease of bone (PDB), bone loss due to cancer therapy, periprosthetic osteolysis, glucocorticoid-induced osteoporosis, rheumatoid arthritis, psoriatic arthritis, osteoarthritis, inflammatory arthridities, and inflammation.

In one preferred embodiment of the invention the cancer is a lymphoma (preferably B-cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma) c) marginal zone lymphomas (including extranodal marginal zone B cell lymphoma (Mucosa-associated lymphatic tissue lymphomas, MALT), nodal marginal zone B cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma) f) hairy cell leukemia, g) lymphocytic lymphoma, waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma j) Hodgkin's disease.

In one further embodiment, the cancer is a B-cell Non-Hodgkin's lymphomas (NHL). In further embodiment, the cancer is a Mantle cell lymphoma (MCL), acute lymphocytic leukemia (ALL), chronic lymphocytic leukemia (CLL), B-cell diffuse large cell lymphoma (DLCL), Burkitt's lymphoma, hairy cell leukemia, follicular lymphoma, multiple myeloma, marginal zone lymphoma, post transplant lymphoproliferative disorder (PTLD), HIV associated lymphoma, waldenstrom's macroglobulinemia, or primary CNS lymphoma.

In one preferred embodiment the cancer is a Non-Hodgkin lymphoma, in one embodiment a B-cell diffuse large cell lymphoma (DLCL). In one embodiment, the method comprises administering to an individual having DLBLC an effective amount of the CSF-1R antibodies described herein in combination with an antagonistic PD-L1 antibody as described herein wherein a prior treatment of the cancer with a PD-L1/PD1 inhibitor selected from the group of an antagonistic PD-L1 antibody or an antagonistic PD1 antibody failed. In one embodiment, the method further comprises administering to the individual an effective amount of at least one additional therapeutic agent, as described below. The CSF-1R antibodies in combination with an antagonistic PD-L1 antibody as described herein can be used either as anti-CSF-1R-anti-PD-L1 combination alone or in addition in combination with other agents in a therapy. In one embodiment, the one or more additional therapeutic agents are selected from rituximab, obinituzumab, cyclophosphamide, doxorubicin, vincristine, prednisolone, methylprednisolone, ifosfamide, carboplatin, etoposide, dexamethasone, high-dose cytarabine, cisplatin, and bendamustine.

In another preferred embodiment of the invention the cancer is a multiple myeloma. In one embodiment, the method comprises administering to an individual having multiple myeloma an effective amount of the CSF-1R antibodies described herein in combination with an antagonistic PD-L1 antibody as described herein wherein a prior treatment of the cancer with a PD-L1/PD1 inhibitor selected from the group of an antagonistic PD-L1 antibody or an antagonistic PD1 antibody failed.

In another preferred embodiment of the invention the cancer is a solid tumor.

In another preferred embodiment of the invention the cancer is a melanoma, urinary bladder cancer (UCB), or lung cancer (e.g. non small cell lung (NSCL) cancer). In another preferred embodiment of the invention the cancer is a Renal cell carcinoma (RCC) or Head and Neck Squamous Cell Carcinoma (HNSCC).

In another preferred embodiment of the invention the cancer is urinary bladder cancer (UCB). In a further aspect, the invention provides a method for treating a bladder cancer or urothelial carcinoma, such as a transitional cell carcinoma (TCC), by administering an effective amount of the CSF-1R antibodies described herein in combination with an antagonistic PD-L1 antibody as described herein wherein a prior treatment of the cancer with a PD-L1/PD1 inhibitor selected from the group of an antagonistic PD-L1 antibody or an antagonistic PD1 antibody failed. In a further aspect of the embodiment, the bladder cancer is a squamous cell carcinoma. In a further aspect, the bladder cancer is selected from the group consisting of adenocarcinoma, small cell carcinoma and sarcoma. In one embodiment, the method comprises administering to an individual having a bladder cancer an effective amount of the CSF-1R antibodies described herein in combination with an antagonistic PD-L1 antibody as described herein wherein a prior treatment of the cancer with a PD-L/PD1 inhibitor selected from the group of an antagonistic PD-L1 antibody or an antagonistic PD1 antibody failed. In one such embodiment, the method further comprises administering to the individual an effective amount of at least one additional therapeutic agent, as described below. The CSF-1R antibodies in combination with an antagonistic PD-L1 antibody as described herein can be used either as anti-CSF-1R-anti-PD-L1 combination alone or in addition in combination with other agents in a therapy. For instance, one or more additional therapeutic agents selected from gemcitabine, cisplatin, methotrexate, vinblastine, doxorubicin, carboplatin, vinflunine, paclitaxel and docetaxel may be co-administered.

In another preferred embodiment of the invention the cancer is melanoma. In further aspects, the invention provides methods for treating melanoma by administering to a patient in need thereof a therapeutically effective amount of the CSF-1R antibodies described herein in combination with an antagonistic PD-L1 antibody as described herein wherein a prior treatment of the cancer with a PD-L1/PD1 inhibitor selected from the group of an antagonistic PD-L1 antibody or an antagonistic PD1 antibody failed. In one such embodiment, the method further comprises administering to the individual an effective amount of at least one additional therapeutic agent, as described below. The CSF-1R antibodies in combination with an antagonistic PD-L1 antibody as described herein can be used either as anti-CSF-1R/anti-PD-L1 combination alone or in addition in combination with other agents in a therapy. For instance, one or more additional therapeutic agents selected from BRAF inhibitors (vemurafenib and dabrafenib) and MEK inhibitors (trametinib and cobimetinib) for BRAF-mutated melanomas. (e.g. V600 mutant melanoma) may be co-administered.

In another preferred embodiment of the invention the cancer is lung cancer. In one embodiment the lung cancer is Small Cell Lung Cancer (SCLC). In one embodiment, the SCLC is a small cell carcinoma (oat cell cancer), mixed small cell/large cell carcinoma or combined small cell carcinoma. In further aspects, the invention provides methods for treating Small Cell Lung Cancer (SCLC) by administering to a patient in need thereof a therapeutically effective amount of the CSF-1R antibodies described herein in combination with an antagonistic PD-L1 antibody as described herein wherein a prior treatment of the cancer with a PD-L1/PD inhibitor selected from the group of an antagonistic PD-L1 antibody or an antagonistic PD1 antibody failed. In one such embodiment, the method further comprises administering to the individual an effective amount of at least one additional therapeutic agent, as described below. The CSF-1R antibodies in combination with an antagonistic PD-L1 antibody as described herein can be used either as anti-CSF-1R/anti-PD-L1 combination alone or in addition in combination with other agents in a therapy. For instance, one or more additional therapeutic agents selected from etoposide, a platinum compound (cisplatin or carboplatin), irinotecan, topotecan, vinca alkaloids (vinblastine, vincristine, or vinorelbine), alkylating agents (cyclophosphamide or ifosfamide), doxorubicin, taxanes (docetaxel or paclitaxel), and gemcitabine may be co-administered. In one embodiment the lung cancer is Non-Small Cell Lung Cancer (NSCLC). In one embodiment, the SCLC is a small cell carcinoma (oat cell cancer), mixed small cell/large cell carcinoma or combined small cell carcinoma. In further aspects, the invention provides methods for treating Non-Small Cell Lung Cancer (NSCLC) by administering to a patient in need thereof a therapeutically effective amount of the CSF-1R antibodies described herein in combination with an antagonistic PD-L1 antibody as described herein wherein a prior treatment of the cancer with a PD-L1/PD1 inhibitor selected from the group of an antagonistic PD-L1 antibody or an antagonistic PD1 antibody failed. In one such embodiment, the method further comprises administering to the individual an effective amount of at least one additional therapeutic agent, as described below. The CSF-1R antibodies in combination with an antagonistic PD-L1 antibody as described herein can be used either as anti-CSF-1R/anti-PD-L1 combination alone or in addition in combination with other agents in a therapy. For instance, one or more additional therapeutic agents selected from cisplatin, carboplatin, paclitaxel, paclitaxel protein bound, docetaxel, gemcitabine, vinorelbine, etoposide, nintedanib, vinblastine, and pemetrexed, afatinib, bevacizumab, cabozantinib, ceritinib, crizotinib, erlotinib hydrochloride, osimertinib, ramucirumab, gefitinib, necitumumab, alectinib, trastuzumab, cetuximab, ipilimumab, trametinib, dabrafenib, vemurafenib, dacomitinib, tivantinib, onartuzumab, especially EGFR tyrosine kinase inhibitors like e.g. erlotinib for EGFR positive cancers, and ALK inhibitors like e.g. critozinib, alectinib, for ALK positive cancers, may be co-administered.

In another preferred embodiment of the invention the cancer is Head and Neck Squamous Cell Carcinoma (HN-SCC). In further aspects, the invention provides methods for treating Head and Neck Squamous Cell Carcinoma (HN-SCC) by administering to a patient in need thereof a therapeutically effective amount of the CSF-1R antibodies described herein in combination with an antagonistic PD-L1 antibody as described herein wherein a prior treatment of the cancer with a PD-L1/PD inhibitor selected from the group of an antagonistic PD-L antibody or an antagonistic PD1 antibody failed. In one such embodiment, the method further comprises administering to the individual an effective amount of at least one additional therapeutic agent, as described below. The CSF-1R antibodies in combination with an antagonistic PD-L1 antibody as described herein can be used either as anti-CSF-1R/anti-PD-L1 combination alone or in addition in combination with other agents in a therapy. For instance, one or more additional therapeutic agents selected from methotrexate, cetuximab, cisplatin, carboplatin, paclitaxel, paclitaxel protein bound, docetaxel and 5-fluorouracil may be co-administered.

In another preferred embodiment of the invention the cancer is Renal cell carcinoma (RCC) In one embodiment, the method comprises administering to an individual having Renal cell carcinoma (RCC) an effective amount of the CSF-1R antibodies described herein in combination with an antagonistic PD-L1 antibody as described herein wherein a prior treatment of the cancer with a PD-L1/PD1 inhibitor selected from the group of an antagonistic PD-L1 antibody or an antagonistic PD1 antibody failed. The CSF-1R antibodies in combination with an antagonistic PD-L1 antibody as described herein can be used either as anti-CSF-1R/anti-PD-L1 combination alone or in addition in combination with other agents in a therapy. For instance, one or more additional therapeutic agents selected from e.g. bevacizumab may be co-administered.

The antibodies described herein are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or *E. coli* cells, and the antibody is recovered from the cells (from the supernatant or after cells lysis).

Recombinant production of antibodies is well-known in the state of the art and described, for example, in the review articles of Makrides, S. C., Protein Expr. Purif. 17 (1999) 183-202: Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A Sepharose®, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The terms "administered in combination with" or "co-administration", "co-administering", "combination therapy" or "combination treatment" refer to the administration of the anti-CSF-1R as described herein, and the antagonistic PD-L1 antibody, as described herein e.g. as separate formulations/applications (or as one single formulation/application). The co-administration can be simultaneous or sequential in either order, wherein there is a time period while both (or all) active agents simultaneously exert their biological activities. The co-administration is either simultaneously or sequentially (e.g. intravenous (i.v.) through a continuous infusion. In one embodiment the co-administration is simultaneously. In one embodiment the co-administration is sequentially. The co-administration is either simultaneously or sequentially (e.g. intravenous (i.v.) through a continuous infusion.

It is self-evident that the antibodies are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician.

The amount of co-administration and the timing of co-administration will depend on the type (species, gender, age, weight, etc.) and condition of the patient being treated and the severity of the disease or condition being treated. Said anti-CSF-1R antibody and further agent are suitably co-administered to the patient at one time or over a series of treatments e.g. on the same day or on the day after.

In one embodiment such additional chemotherapeutic agents, which may be administered with the anti-CSF-1R antibody as described herein and the antagonistic PD-L1 antibody, as described herein, include, but are not limited to, anti-neoplastic agents including alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); Temodal® (temozolamide), ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil (5FU), fluorodeoxyuridine, gemcitabine, cytosine arabinoside (AraC, cytarabine), 5-azacytidine, 2,2'-difluorodeoxycytidine, purine analogs such as 6-merca.rho..topurine, 6-thioguamne, azathioprine, T-deoxycoformycin (pentostatin), erythrohydroxynonyladenine (EHNA), fludarabine phosphate, and 2-chlorodeoxyadeno sine (cladribine, 2-CdA); natural products including antimitotic drugs such as paclitaxel, vinca alkaloids including vinblastine (VLB), vincristine, and vinorelbine, taxotere, estramustine, and estramustine phosphate; pipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL 2, G-CSF and GM-CSF; miscellaneous agents including platinum coordination complexes such as oxaliplatin, cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o, p-DDD) and aminoglutethimide; hormones and antagonists including adrenocorticosteroid antagonists such as prednisone and equivalents, dexamethasone and aminoglutethimide; Gemzar® (gemcitabine), progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Therapies targeting epigenetic mechanism including, but not limited to, histone deacetylase inhibitors, demethylating agents (e.g., Vidaza®) and release of transcriptional repression (ATRA) therapies can also be combined with the antigen binding proteins. In one embodiment the chemotherapeutic agent is selected from the group consisting of taxanes (like e.g. paclitaxel (Taxol™), docetaxel (Taxotere® Taxotcro), modified paclitaxel (e.g., Abraxane® and Opaxio™), doxorubicin, sunitinib (Sutent®), sorafenib (Nexavar®), and other multikinase inhibitors, oxaliplatin, cisplatin and carboplatin, etoposide, gemcitabine, and vinblastine. In one embodiment the chemotherapeutic agent is selected from the group consisting of taxanes (like e.g. Taxol™ (paclitaxel), docetaxel (Taxotere®), modified paclitaxel (e.g. Abraxane® and Opaxio™). In one embodiment, the additional chemotherapeutic agent is selected from 5-fluorouracil (5-FU), leucovorin, irinotecan, or oxaliplatin. In one embodiment the chemotherapeutic agent is 5-fluorouracil, leucovorin and irinotecan (FOLFIRI). In one embodiment the chemotherapeutic agent is 5-fluorouracil, and oxaliplatin (FOLFOX).

In one preferred embodiment, no additional chemotherapeutic agent is administered together with the anti-CSF-1R antibody in combination with the PD1/PD-L1 inhibitor.

Description of the Amino Acid Sequences

SEQ ID NO: 1 heavy chain variable domain, anti-CSF-1R antibody emactuzumab
SEQ ID NO: 2 light chain variable domain, anti-CSF-1R antibody emactuzumab
SEQ ID NO: 3 heavy chain variable domain of anti-PD-L1 antibody atezolizumab
SEQ ID NO: 4 light chain variable domain of anti-PD-L1 antibody atezolizumab
SEQ ID NO: 5 heavy chain variable domain of anti-PD-L1 antibody durvalumab
SEQ ID NO: 6 light chain variable domain of anti-PD-L1 antibody durvalumab
SEQ ID NO: 7 heavy chain variable domain of anti-PD1 antibody pembrolizumab
SEQ ID NO: 8 light chain variable domain of anti-PD1 antibody pembrolizumab
SEQ ID NO: 9 heavy chain variable domain of anti-PD1 antibody nivolumab
SEQ ID NO: 10 light chain variable domain of anti-PD1 antibody nivolumab
SEQ ID NO: 11 exemplary human CSF-1R (wt CSF-1R)
SEQ ID NO: 12 human CSF-1R Extracellular Domain (domains DI-D5)
SEQ ID NO: 13 human CSF-1R fragment domains DI-D3
SEQ ID NO: 14 human CSF-1R fragment domains D4-D5
SEQ ID NO: 15 human CSF-1R fragment delD4 (domains 1, 2, 3 and 5 of the Extracellular Domain)
SEQ ID NO: 16 exemplary human CSF-1
SEQ ID NO: 17 exemplary human IL-34
SEQ ID NO: 18 exemplary human PD-L1
SEQ ID NO: 19 exemplary human PD1
SEQ ID NO: 20 human kappa light chain constant region
SEQ ID NO: 21 human heavy chain constant region derived from IgG1
SEQ ID NO: 22 human heavy chain constant region derived from IgG1 mutated on L234A and L235A
SEQ ID NO: 23 human heavy chain constant region derived from IgG4
SEQ ID NO: 24 human heavy chain constant region derived from IgG4 mutated on S228P
SEQ ID NO: 25 heavy chain variable domain, anti-CSF-1R antibody 1 of U.S. Pat. No. 8,263,079
SEQ ID NO: 26 light chain variable domain, anti-CSF-1R antibody 1 of U.S. Pat. No. 8,263,079
SEQ ID NO: 27 heavy chain, anti-CSF-1R antibody 1 of U.S. Pat. No. 8,263,079
SEQ ID NO: 28 light chain, anti-CSF-1R antibody 1 of U.S. Pat. No. 8,263,079
SEQ ID NO: 29 heavy chain of anti-PD-L1 antibody avelumab
SEQ ID NO: 30 light chain of anti-PD-L1 antibody avelumab In the following, specific embodiments of the invention are described:

1A. An antibody which binds to human CSF-1R for use in
  a) the treatment of cancer in combination with an antagonistic PD-L1 antibody, wherein a prior treatment of the cancer with a PD-L1-PD1 inhibitor selected from the group of an antagonistic PD-L1 antibody or an antagonistic PD1 antibody failed,
  or
  b) the treatment of a patient suffering from a cancer with CSF-1R expressing macrophage infiltrate in combination with an antagonistic PD-L1 antibody, wherein a prior treatment of the patient with a PD-L1/PD1 inhibitor selected from the group of an antagonistic PD-L antibody or an antagonistic PD1 antibody failed.

1B. An antibody which binds to human CSF-1R, for use in
a) the treatment of cancer in combination with an antagonistic PD-L1 antibody, wherein the cancer showed disease progression (in one embodiment a Progressive Disease (PD) according to the RECIST1.1 criteria for solid tumors) on (and/or after) the prior treatment of the cancer with a PD-L1/PD1 inhibitor selected from the group of an antagonistic PD-L1 antibody or an antagonistic PD1 antibody,
or
b) the treatment of a patient suffering from a cancer with CSF-1R expressing macrophage infiltrate in combination with an antagonistic PD-L antibody, wherein the patient (suffering from cancer) showed disease progression on (and/or after) the prior treatment of the patient with a PD-L1/PD1 inhibitor selected from the group of an antagonistic PD-L1 antibody or an antagonistic PD1 antibody.

2. The anti-CSF-1R antibody for use in the treatment according to embodiment 1, wherein the CSF-1R antibody binds to domain D4 or D5 of the extracellular domain (ECD) of CSF-1R.

3. The anti-CSF-1R antibody for use in the treatment according to any one of embodiments 1 to 6, wherein the anti-CSF-1R antibody comprises
a heavy chain variable domain VH of SEQ ID NO: 1 and a light chain variable domain VL of SEQ ID NO:2.

4. The anti-CSF-1R antibody for use in the treatment according to embodiment 1,
wherein anti-CSF-1R antibody comprises
a heavy chain variable domain VH of SEQ ID NO: 1 and a light chain variable domain VL of SEQ ID NO:2, and
the antagonistic PD-L1 antibody comprises
a) a heavy chain variable domain VH of SEQ ID NO:3 and a light chain variable domain VL of SEQ ID NO:4
or b) a heavy chain variable domain VH of SEQ ID NO:5 and a light chain variable domain VL of SEQ ID NO:6.

5. The anti-CSF-1R antibody for use in the treatment according to embodiment 1,
wherein anti-CSF-1R antibody comprises
a heavy chain variable domain VH of SEQ ID NO: 1 and a light chain variable domain VL of SEQ ID NO:2, and
the antagonistic PD-L1 antibody comprises
a heavy chain variable domain VH of SEQ ID NO:3 and a light chain variable domain VL of SEQ ID NO:4.

6. The anti-CSF-1R antibody for use in the treatment according to any one of embodiments 1 to 5, wherein in the combination treatment the anti-CSF-1R antibody is emactuzumab and the antagonistic PD-L1 antibody is atezolizumab or durvalumab or avelumab.

7. The anti-CSF-1R antibody for use in the treatment according to any one of embodiments 1 to 5, wherein in the combination treatment the anti-CSF-1R antibody is emactuzumab and the antagonistic PD-L1 antibody is atezolizumab or durvalumab or avelumab.

8. The anti-CSF-1R antibody for use in the treatment according to embodiment 1,
wherein anti-CSF-1R antibody comprises
a heavy chain variable domain VH of SEQ ID NO:25 and a light chain variable domain VL of SEQ ID NO:26, and
the antagonistic PD-L1 antibody comprises
a heavy chain variable domain VH of SEQ ID NO:5 and a light chain variable domain VL of SEQ ID NO:6.

9. The anti-CSF-1R antibody for use in the treatment according to any one of embodiments 1 to 8, wherein the prior treatment which failed was a atezolizumab or durvalumab or avelumab treatment (In one embodiment a atezolizumab or durvalumab or avelumab monotherapy).

10. The anti-CSF-1R antibody for use in the treatment according to any one of embodiments 1 to 8, wherein the prior treatment which failed was a atezolizumab treatment (In one embodiment a atezolizumab monotherapy).

11. The anti-CSF-1R antibody for use in the treatment according to any one of embodiments 1 to 8, wherein the prior treatment which failed was a durvalumab or avelumab treatment (In one embodiment a durvalumab or avelumab monotherapy).

12. The anti-CSF-1R antibody for use in the treatment according to any one of embodiments 1 to 8, wherein the prior treatment which failed was a pembrolizumab or nivolumab treatment (In one embodiment a pembrolizumab or nivolumab monotherapy).

13. The anti-CSF-1R antibody for use in the treatment according to any one of embodiments 1 to 12, wherein the antagonistic PD-L1 antibody used in combination is administered at a dose of 1100-1300 mg (in one embodiment at a dose of 1200 mg) at each cycle.

14. The anti-CSF-1R antibody for use in the treatment according to any one of embodiments 1 to 13, wherein the anti-CSF-1R antibody is administered at a dose of 900-1100 mg (in one embodiment at a dose of 1000 mg) at each cycle.

15. The anti-CSF-1R antibody for use in the treatment according to any one of embodiments 1 to 14, wherein the combined therapy is for use in treating or delaying progression of tumor growth (or of an immune related disease such as tumor immunity).

16. The anti-CSF-1R antibody for use in the treatment according to any one of embodiments 1 to 14, wherein the combined therapy is for use in stimulating an immune response or function, such as T cell activity.

In the Following, Specific Embodiments of the Invention are Described:

1A. A pharmaceutical composition or medicament comprising an antibody which binds to human CSF-1R, for use in
a) the treatment of cancer in combination with an antagonistic PD-L1 antibody, wherein a prior treatment of the cancer with a PD-L/PD1 inhibitor selected from the group of an antagonistic PD-L1 antibody or an antagonistic PD1 antibody failed,
or
b) the treatment of a patient suffering from a cancer with CSF-1R expressing macrophage infiltrate in combination with an antagonistic PD-L1 antibody, wherein a prior treatment of the patient with a PD-L1/PD1 inhibitor selected from the group of an antagonistic PD-L1 antibody or an antagonistic PD1 antibody failed.

1B. A pharmaceutical composition or medicament comprising an antibody which binds to human CSF-1R, for use in
a) the treatment of cancer in combination with an antagonistic PD-L1 antibody, wherein the cancer showed disease progression (in one embodiment a Progressive Disease (PD) according to the RECIST1.1 criteria for solid tumors) on (and/or after) the prior treatment of the cancer with a PD-L/PD1 inhibitor selected from the group of an antagonistic PD-L1 antibody or an antagonistic PD1 antibody,
or
b) the treatment of a patient suffering from a cancer with CSF-1R expressing macrophage infiltrate in combination with an antagonistic PD-L1 antibody, wherein the patient (suffering from cancer) showed disease progression on (and/or after) the prior treatment of the patient with a PD-L1/PD1 inhibitor selected from the group of an antagonistic PD-L1 antibody or an antagonistic PD1 antibody.
2. The pharmaceutical composition or medicament according to embodiment 1, wherein the CSF-1R antibody binds to domain D4 or D5 of the extracellular domain (ECD) of CSF-1R.
3. The pharmaceutical composition or medicament according to any one of embodiments 1 to 6, wherein the anti-CSF-1R antibody comprises a heavy chain variable domain VH of SEQ ID NO: 1 and a light chain variable domain VL of SEQ ID NO:2.
4. The pharmaceutical composition or medicament according to embodiment 1, wherein anti-CSF-1R antibody comprises
 a heavy chain variable domain VH of SEQ ID NO: 1 and a light chain variable domain VL of SEQ ID NO:2, and
 the antagonistic PD-L1 antibody comprises
 a) a heavy chain variable domain VH of SEQ ID NO:3 and a light chain variable domain VL of SEQ ID NO:4 or b) a heavy chain variable domain VH of SEQ ID NO:5 and a light chain variable domain VL of SEQ ID NO:6.
5. The pharmaceutical composition or medicament according to embodiment 1,
 wherein anti-CSF-1R antibody comprises
 a heavy chain variable domain VH of SEQ ID NO: 1 and a light chain variable domain VL of SEQ ID NO:2, and
 the antagonistic PD-L1 antibody comprises
 a heavy chain variable domain VH of SEQ ID NO:3 and a light chain variable domain VL of SEQ ID NO:4.
6. The pharmaceutical composition or medicament according to any one of embodiments 1 to 5, wherein in the combination treatment the anti-CSF-1R antibody is emactuzumab and the antagonistic PD-L1 antibody is atezolizumab or durvalumab or avelumab.
7. The pharmaceutical composition or medicament according to any one of embodiments 1 to 5, wherein in the combination treatment the anti-CSF-1R antibody is emactuzumab and the antagonistic PD-L1 antibody is atezolizumab or durvalumab or avelumab.
8. The pharmaceutical composition or medicament according to embodiment 1, wherein anti-CSF-1R antibody comprises
 a heavy chain variable domain VH of SEQ ID NO:25 and a light chain variable domain VL of SEQ ID NO:26, and
 the antagonistic PD-L1 antibody comprises
 a heavy chain variable domain VH of SEQ ID NO:5 and a light chain variable domain VL of SEQ ID NO:6.
9. The pharmaceutical composition or medicament according to any one of embodiments 1 to 8, wherein the prior treatment which failed was a atezolizumab or durvalumab or avelumab treatment (In one embodiment a atezolizumab or durvalumab or avelumab monotherapy).
10. The pharmaceutical composition or medicament according to any one of embodiments 1 to 8, wherein the prior treatment which failed was a atezolizumab treatment (In one embodiment a atezolizumab monotherapy).
11. The pharmaceutical composition or medicament according to any one of embodiments 1 to 8, wherein the prior treatment which failed was a durvalumab or avelumab treatment (In one embodiment a durvalumab or avelumab monotherapy).
12. The pharmaceutical composition or medicament according to any one of embodiments 1 to 8, wherein the prior treatment which failed was a pembrolizumab or nivolumab treatment (In one embodiment a pembrolizumab or nivolumab monotherapy).
13. The pharmaceutical composition or medicament according to any one of embodiments 1 to 12, wherein the antagonistic PD-L1 antibody used in combination is administered at a dose of 1100-1300 mg (in one embodiment at a dose of 1200 mg) at each cycle.
14. The pharmaceutical composition or medicament according to any one of embodiments 1 to 13, wherein the anti-CSF-1R antibody is administered at a dose of 900-1100 mg (in one embodiment at a dose of 1000 mg) at each cycle.
15. The pharmaceutical composition or medicament according to any one of embodiments 1 to 14, wherein the combined therapy is for use in treating or delaying progression of tumor growth (or of an immune related disease such as tumor immunity).
16. The pharmaceutical composition or medicament according to any one of embodiments 1 to 14, wherein the combined therapy is for use in stimulating an immune response or function, such as T cell activity.
17. The pharmaceutical composition or medicament according to any one of embodiments 1 to 16, wherein the cancer is melanoma, urinary bladder cancer (UCB), or non small cell lung (NSCL) cancer.
18. The pharmaceutical composition or medicament according to any one of embodiments 1 to 16, wherein the cancer is urinary bladder cancer (UCB), or non small cell lung (NSCL) cancer.
19. The pharmaceutical composition or medicament according to any one of embodiments 1 to 16, wherein the cancer is Renal cell carcinoma (RCC) or Head and Neck Squamous Cell Carcinoma (HNSCC).

In the Following, Specific Embodiments of the Invention are Described:

1A. Use of an antibody which binds to human CSF-1R in the manufacture of a medicament for use in
 a) the treatment of cancer in combination with an antagonistic PD-L1 antibody, wherein a prior treatment of the cancer with a PD-L1/PD1 inhibitor selected from the group of an antagonistic PD-L1 antibody or an antagonistic PD1 antibody failed,
 or
 b) the treatment of a patient suffering from a cancer with CSF-1R expressing macrophage infiltrate in combination with an antagonistic PD-L1 antibody, wherein a prior treatment of the patient with a PD-L1/PD1 inhibitor selected from the group of an antagonistic PD-L1 antibody or an antagonistic PD1 antibody failed.

1B. Use of an antibody which binds to human CSF-1R in the manufacture of a medicament for use in
 a) the treatment of cancer in combination with an antagonistic PD-L1 antibody, wherein the cancer showed disease progression (in one embodiment a Progressive Disease (PD) according to the RECIST1.1 criteria for solid tumors) on (and/or after) the prior treatment of the cancer with a PD-L1/PD1 inhibitor selected from the group of an antagonistic PD-L1 antibody or an antagonistic PD1 antibody,
 or
 b) the treatment of a patient suffering from a cancer with CSF-1R expressing macrophage infiltrate in combination with an antagonistic PD-L1 antibody, wherein the patient (suffering from cancer) showed disease progression on (and/or after) the prior treatment of the patient with a PD-L1/PD1 inhibitor selected from the group of an antagonistic PD-L1 antibody or an antagonistic PD1 antibody.
2. The use according to embodiment 1, wherein the CSF-1R antibody binds to domain D4 or D5 of the extracellular domain (ECD) of CSF-1R.
3. The use according to any one of embodiments 1 to 6, wherein the anti-CSF-1R antibody comprises
 a heavy chain variable domain VH of SEQ ID NO: 1 and a light chain variable domain VL of SEQ ID NO:2.
4. The use according to embodiment 1,
 wherein anti-CSF-1R antibody comprises
 a heavy chain variable domain VH of SEQ ID NO: 1 and a light chain variable domain VL of SEQ ID NO:2, and
 the antagonistic PD-L1 antibody comprises
 a) a heavy chain variable domain VH of SEQ ID NO:3 and a light chain variable domain VL of SEQ ID NO:4 or b) a heavy chain variable domain VH of SEQ ID NO:5 and a light chain variable domain VL of SEQ ID NO:6.
5. The use according to embodiment 1,
 wherein anti-CSF-1R antibody comprises
 a heavy chain variable domain VH of SEQ ID NO: 1 and a light chain variable domain VL of SEQ ID NO:2, and
 the antagonistic PD-L1 antibody comprises
 a heavy chain variable domain VH of SEQ ID NO:3 and a light chain variable domain VL of SEQ ID NO:4.
6. The use according to any one of embodiments 1 to 5, wherein in the combination treatment the anti-CSF-1R antibody is emactuzumab and the antagonistic PD-L1 antibody is atezolizumab or durvalumab or avelumab.
7. The use according to any one of embodiments 1 to 5, wherein in the combination treatment the anti-CSF-1R antibody is emactuzumab and the antagonistic PD-L1 antibody is atezolizumab or durvalumab or avelumab.
8. The use according to embodiment 1,
 wherein anti-CSF-1R antibody comprises
 a heavy chain variable domain VH of SEQ ID NO:25 and a light chain variable domain VL of SEQ ID NO:26, and
 the antagonistic PD-L1 antibody comprises
 a heavy chain variable domain VH of SEQ ID NO:5 and a light chain variable domain VL of SEQ ID NO:6.
9. The use according to any one of embodiments 1 to 8, wherein the prior treatment which failed was a atezolizumab or durvalumab or avelumab treatment (In one embodiment a atezolizumab or durvalumab or avelumab monotherapy).
10. The use according to any one of embodiments 1 to 8, wherein the prior treatment which failed was a atezolizumab treatment (In one embodiment a atezolizumab monotherapy).
11. The use according to any one of embodiments 1 to 8, wherein the prior treatment which failed was a durvalumab or avelumab treatment (In one embodiment a durvalumab or avelumab monotherapy).
12. The use according to any one of embodiments 1 to 8, wherein the prior treatment which failed was a pembrolizumab or nivolumab treatment (In one embodiment a pembrolizumab or nivolumab monotherapy).
13. The use according to any one of embodiments 1 to 12, wherein the antagonistic PD-L1 antibody used in combination is administered at a dose of 1100-1300 mg (in one embodiment at a dose of 1200 mg) at each cycle.
14. The use according to any one of embodiments 1 to 13, wherein the anti-CSF-1R antibody is administered at a dose of 900-1100 mg (in one embodiment at a dose of 1000 mg) at each cycle.
15. The use according to any one of embodiments 1 to 14, wherein the combined therapy is for use in treating or delaying progression of tumor growth (or of an immune related disease such as tumor immunity).
16. The use according to any one of embodiments 1 to 14, wherein the combined therapy is for use in stimulating an immune response or function, such as T cell activity.
17. The use according to any one of embodiments 1 to 16, wherein the cancer is melanoma, urinary bladder cancer (UCB), or non small cell lung (NSCL) cancer.
18. The use according to any one of embodiments 1 to 16, wherein the cancer is urinary bladder cancer (UCB), or non small cell lung (NSCL) cancer.
19. The use according to any one of embodiments 1 to 16, wherein the cancer is Renal cell carcinoma (RCC) or Head and Neck Squamous Cell Carcinoma (HNSCC).

In the Following, Specific Embodiments of the Invention are Described:

1A. A method of treatment, the method comprising administering (an effective amount of) an antibody which binds to human CSF-1R, for
 a) the treatment of cancer in combination with an antagonistic PD-L1 antibody, wherein a prior treatment of the cancer with a PD-L1/PD1 inhibitor selected from the group of an antagonistic PD-L1 antibody or an antagonistic PD1 antibody failed,
 or
 b) the treatment of a patient suffering from a cancer with CSF-1R expressing macrophage infiltrate in combination with an antagonistic PD-L1 antibody, wherein a prior treatment of the patient with a PD-L1/PD1 inhibitor selected from the group of an antagonistic PD-L1 antibody or an antagonistic PD1 antibody failed.

1B. A method of treatment, the method comprising administering (an effective amount of) an antibody which binds to human CSF-1R, for
 a) the treatment of cancer in combination with an antagonistic PD-L1 antibody, wherein the cancer showed disease progression (in one embodiment a Progressive Disease (PD) according to the RECIST1.1 criteria for solid tumors) on (and/or after) the prior treatment of the cancer with a PD-L/PD1 inhibitor selected from the group of an antagonistic PD-L1 antibody or an antagonistic PD1 antibody,
 or
 b) the treatment of a patient suffering from a cancer with CSF-1R expressing macrophage infiltrate in combination with an antagonistic PD-L1 antibody, wherein the patient (suffering from cancer) showed disease progression on (and/or after) the prior treatment of the patient with a PD-L1/PD1 inhibitor selected from the group of an antagonistic PD-L1 antibody or an antagonistic PD1 antibody.
2. The method according to embodiment 1, wherein the CSF-1R antibody binds to domain D4 or D5 of the extracellular domain (ECD) of CSF-1R.
3. The method according to any one of embodiments 1 to 6, wherein the anti-CSF-1R antibody comprises
 a heavy chain variable domain VH of SEQ ID NO: 1 and a light chain variable domain VL of SEQ ID NO:2.

4. The method according to embodiment 1,
   wherein anti-CSF-1R antibody comprises
   a heavy chain variable domain VH of SEQ ID NO: 1 and a light chain variable domain VL of SEQ ID NO:2, and
   the antagonistic PD-L1 antibody comprises
   a) a heavy chain variable domain VH of SEQ ID NO:3 and a light chain variable domain VL of SEQ ID NO:4
   or b) a heavy chain variable domain VH of SEQ ID NO:5 and a light chain variable domain VL of SEQ ID NO:6 or c) a heavy chain variable domain VH of SEQ ID NO:5 and a light chain variable domain VL of SEQ ID NO:6.
5. The method according to embodiment 1,
   wherein anti-CSF-1R antibody comprises
   a heavy chain variable domain VH of SEQ ID NO: 1 and a light chain variable domain VL of SEQ ID NO:2, and
   the antagonistic PD-L1 antibody comprises
   a heavy chain variable domain VH of SEQ ID NO:3 and a light chain variable domain VL of SEQ ID NO:4.
6. The method according to any one of embodiments 1 to 5, wherein in the combination treatment the anti-CSF-1R antibody is emactuzumab and the antagonistic PD-L1 antibody is atezolizumab or durvalumab or avelumab.
7. The method according to any one of embodiments 1 to 5, wherein in the combination treatment the anti-CSF-1R antibody is emactuzumab and the antagonistic PD-L1 antibody is atezolizumab or durvalumab or avelumab.
8. The method according to embodiment 1,
   wherein anti-CSF-1R antibody comprises
   a heavy chain variable domain VH of SEQ ID NO:25 and a light chain variable domain VL of SEQ ID NO:26, and
   the antagonistic PD-L1 antibody comprises
   a heavy chain variable domain VH of SEQ ID NO:5 and a light chain variable domain VL of SEQ ID NO:6.
9. The method according to any one of embodiments 1 to 8, wherein the prior treatment which failed was a atezolizumab or durvalumab or avelumab treatment (In one embodiment a atezolizumab or durvalumab or avelumab monotherapy).
10. The method according to any one of embodiments 1 to 8, wherein the prior treatment which failed was a atezolizumab treatment (In one embodiment a atezolizumab monotherapy).
11. The method according to any one of embodiments 1 to 8, wherein the prior treatment which failed was a durvalumab or avelumab treatment (In one embodiment a durvalumab or avelumab monotherapy).
12. The method according to any one of embodiments 1 to 8, wherein the prior treatment which failed was a pembrolizumab or nivolumab treatment (In one embodiment a pembrolizumab or nivolumab monotherapy).
13. The method according to any one of embodiments 1 to 12, wherein the antagonistic PD-L1 antibody used in combination is administered at a dose of 1100-1300 mg (in one embodiment at a dose of 1200 mg) at each cycle.
14. The method according to any one of embodiments 1 to 13, wherein the anti-CSF-1R antibody is administered at a dose of 900-1100 mg (in one embodiment at a dose of 1000 mg) at each cycle.
15. The method according to any one of embodiments 1 to 14, wherein the combined therapy is for use in treating or delaying progression of tumor growth (or of an immune related disease such as tumor immunity).
16. The method according to any one of embodiments 1 to 14, wherein the combined therapy is for use in stimulating an immune response or function, such as T cell activity.
17. The method according to any one of embodiments 1 to 16, wherein the cancer is melanoma, urinary bladder cancer (UCB), or non small cell lung (NSCL) cancer.
18. The method according to any one of embodiments 1 to 16, wherein the cancer is urinary bladder cancer (UCB), or non small cell lung (NSCL) cancer.
19. The method according to any one of embodiments 1 to 16, wherein the cancer is Renal cell carcinoma (RCC) or Head and Neck Squamous Cell Carcinoma (HNSCC).

In the Following, Specific Embodiments of the Invention are Described:

1A. An antagonistic PD-L1 antibody, for use in
   a) the treatment of cancer in combination with an antibody which binds to human CSF-1R, wherein a prior treatment of the cancer with a PD-L1/PD1 inhibitor selected from the group of an antagonistic PD-L antibody or an antagonistic PD1 antibody failed,
   or
   b) the treatment of a patient suffering from a cancer with CSF-1R expressing macrophage infiltrate in combination with an antibody which binds to human CSF-1R, wherein a prior treatment of the patient with a PD-L1/PD1 inhibitor selected from the group of an antagonistic PD-L1 antibody or an antagonistic PD1 antibody failed.

1B. An antagonistic PD-L1 antibody, for use in
   a) the treatment of cancer in combination with an antibody which binds to human CSF-1R, wherein the cancer showed disease progression (in one embodiment a Progressive Disease (PD) according to the RECIST 1.1 criteria for solid tumors) on (and/or after) the prior treatment of the cancer with a PD-L1/PD1 inhibitor selected from the group of an antagonistic PD-L1 antibody or an antagonistic PD1 antibody,
   or
   b) the treatment of a patient suffering from a cancer with CSF-1R expressing macrophage infiltrate in combination with an antibody which binds to human CSF-1R, wherein the patient (suffering from cancer) showed disease progression on (and/or after) the prior treatment of the patient with a PD-L1/PD1 inhibitor selected from the group of an antagonistic PD-L1 antibody or an antagonistic PD1 antibody.

2. The antagonistic PD-L1 antibody for use in the treatment according to embodiment 1, wherein the CSF-1R antibody binds to domain D4 or D5 of the extracellular domain (ECD) of CSF-1R.

3. The antagonistic PD-L1 antibody for use in the treatment according to any one of embodiments 1 to 6, wherein the anti-CSF-1R antibody comprises
   a heavy chain variable domain VH of SEQ ID NO: 1 and a light chain variable domain VL of SEQ ID NO:2.

4. The antagonistic PD-L antibody for use in the treatment according to embodiment 1,
   wherein anti-CSF-1R antibody comprises
   a heavy chain variable domain VH of SEQ ID NO: 1 and a light chain variable domain VL of SEQ ID NO:2, and
   the antagonistic PD-L1 antibody comprises
   a) a heavy chain variable domain VH of SEQ ID NO:3 and a light chain variable domain VL of SEQ ID NO:4
   or b) a heavy chain variable domain VH of SEQ ID NO:5 and a light chain variable domain VL of SEQ ID NO:6.

5. The antagonistic PD-L1 antibody for use in the treatment according to embodiment 1,
   wherein anti-CSF-1R antibody comprises
   a heavy chain variable domain VH of SEQ ID NO: 1 and a light chain variable domain VL of SEQ ID NO:2, and
   the antagonistic PD-L1 antibody comprises
   a heavy chain variable domain VH of SEQ ID NO:3 and a light chain variable domain VL of SEQ ID NO:4.
6. The antagonistic PD-L1 antibody for use in the treatment according to any one of embodiments 1 to 5, wherein in the combination treatment the anti-CSF-1R antibody is emactuzumab and the antagonistic PD-L1 antibody is atezolizumab or durvalumab or avelumab.
7. The antagonistic PD-L1 antibody for use in the treatment according to any one of embodiments 1 to 5, wherein in the combination treatment the anti-CSF-1R antibody is emactuzumab and the antagonistic PD-L1 antibody is atezolizumab or durvalumab or avelumab.
8. The antagonistic PD-L1 antibody for use in the treatment according to embodiment 1,
   wherein anti-CSF-1R antibody comprises
   a heavy chain variable domain VH of SEQ ID NO:25 and a light chain variable domain VL of SEQ ID NO:26, and
   the antagonistic PD-L1 antibody comprises
   a heavy chain variable domain VH of SEQ ID NO:5 and a light chain variable domain VL of SEQ ID NO:6.
9. The antagonistic PD-L1 antibody for use in the treatment according to any one of embodiments 1 to 8, wherein the prior treatment which failed was a atezolizumab or durvalumab or avelumab treatment (In one embodiment a atezolizumab or durvalumab or avelumab monotherapy).
10. The antagonistic PD-L1 antibody for use in the treatment according to any one of embodiments 1 to 8, wherein the prior treatment which failed was a atezolizumab treatment (In one embodiment a atezolizumab monotherapy).
11. The antagonistic PD-L1 antibody for use in the treatment according to any one of embodiments 1 to 8, wherein the prior treatment which failed was a durvalumab or avelumab treatment (In one embodiment a durvalumab or avelumab monotherapy).
12. The antagonistic PD-L1 antibody for use in the treatment according to any one of embodiments 1 to 8, wherein the prior treatment which failed was a pembrolizumab or nivolumab treatment (In one embodiment a pembrolizumab or nivolumab monotherapy).
13. The antagonistic PD-L1 antibody for use in the treatment according to any one of embodiments 1 to 12, wherein the antagonistic PD-L1 antibody used in combination is administered at a dose of 1100-1300 mg (in one embodiment at a dose of 1200 mg) at each cycle.
14. The antagonistic PD-L1 antibody for use in the treatment according to any one of embodiments 1 to 13, wherein the anti-CSF-1R antibody is administered at a dose of 900-1100 mg (in one embodiment at a dose of 1000 mg) at each cycle.
15. The antagonistic PD-L1 antibody for use in the treatment according to any one of embodiments 1 to 14, wherein the combined therapy is for use in treating or delaying progression of tumor growth (or of an immune related disease such as tumor immunity).
16. The antagonistic PD-L1 antibody for use in the treatment according to any one of embodiments 1 to 14, wherein the combined therapy is for use in stimulating an immune response or function, such as T cell activity.
17. The antagonistic PD-L1 antibody for use in the treatment according to any one of embodiments 1 to 16, wherein the cancer is melanoma, urinary bladder cancer (UCB), or non small cell lung (NSCL) cancer.
18. The antagonistic PD-L1 antibody for use in the treatment according to any one of embodiments 1 to 16, wherein the cancer is urinary bladder cancer (UCB), or non small cell lung (NSCL) cancer.
19. The antagonistic PD-L1 antibody for use in the treatment according to any one of embodiments 1 to 16, wherein the cancer is Renal cell carcinoma (RCC) or Head and Neck Squamous Cell Carcinoma (HNSCC).

EXAMPLES

Determination of the Binding of Anti-CSF-1R Antibodies to Human CSF-1R Fragment delD4 and to Human CSF-1R Extracellular Domain (CSF-1R-ECD)

The binding of anti-CSF-1R antibodies to human CSF-1R fragment delD4 (SEQ ID NO: 15) and to human CSF-1R Extracellular Domain (CSF-1R-ECD) (SEQ ID NO: 12) was measured as described in Example 4 of WO 2011/070024. Results of the binding signal in Relative Units (RU) are shown below.

TABLE

Binding of <CSF-1R> MAbs to human CSF-1R fragment delD4 and CSF-1R-ECD, measured by SPR

|  | Binding to delD4 [RU] | Binding to CSF-1R-ECD [RU] |
| --- | --- | --- |
| emactuzumab | 0 | 237 |

Anti-CSF-1R emactuzumab showed binding to the human CSF-1R Extracellular Domain (CSF-1R-ECD): however no binding was detected to CSF-1R fragment delD4.

Determination of the Binding of Anti-CSF-1R Antibodies to Human CSF-1R Fragment D1-D3

The binding of anti-CSF-1R antibodies to f anti-CSF-1R antibodies to human CSF-1R fragment D1-D3 (SEQ ID NO:13) was measured as described in Example 10 of WO2011/070024. Results are shown below.

TABLE

Binding of human CSF-1R fragment D1-D3 measured by SPR

| CSF-1R Mab | Sub domain | $K_D$ (nM) |
| --- | --- | --- |
| emactuzumab | D1-D3 | no binding |

Combination of Anti-CSF-1R Antibody and an Antagonistic Anti-PD-L1 Antibody after PD1/PD-L1 Treatment Failure:

Clinical efficacy in the sense of anti-tumor activity was/will be assessed as follows:

Best overall response.

Overall response rate (ORR), defined as partial response rate plus complete response rate, confirmed by repeated assessments ≥4 weeks after initial documentation.

Progressive-free survival (PFS), defined as the time from first study treatment to the first occurrence of disease progression or death, whichever occurs first.

Duration of response (DOR), defined as the time from the first occurrence of a documented objective response to the time of progression or death from any cause, whichever occurs first.

Clinical benefit rate (CBR), defined as partial response rate plus complete response rate plus stable disease rate.

Best overall response, objective response and disease progression will be determined by Investigator assessment and by central review using both conventional RECIST v1.1 and modified RECIST criteria. Optional submission of the latest (not older than 6 months prior to Cycle 1 Day 1) pre-study computed tomography (CT) scans (historical CT scans) is highly encouraged if available. This scan will be compared to those collected during the study to determine longitudinal tumor-growth kinetics.

Example 1.1: Combination of Anti-CSF-1R Antibody and Anti-PDL1 Antibody after Anti-PDL1 Antibody Treatment Failure in Urothelial Bladder Cancer (UBC)

The example presents the case of a 52 y/o male patient diagnosed with UBC in October 2013. The patient had received 6 cycles of methotrexate, vinblastine, adriamycine and CDDP.

Because of progressive disease under this treatment, the patient was included in the clinical trial GO029294 (IMvigor211) and received a total of seven infusions of the anti-PD-L1 antibody atezolizumab (TECENTRIQ) (1200 mg every 3 weeks). The patient showed continuous disease progression (Progressive Disease (PD) according to RECIST 1.1) and treatment was discontinued. The patient then entered clinical study BP29428 and received combination treatment of anti-CSF1R antibody emactuzumab (1000 mg) and atezolizumab (1200 mg) every 3 weeks. Under this regimen the patient, previously unresponsive to anti-PD-L1 monotherapy, showed initially a partial response (PR according to RECIST 1.1) followed by a complete response (CR). Results are shown in FIG. 1.

Example 1.2: Combination of Anti-CSF-1R Antibody and Anti-PDL1 Antibody after Anti-PDL1 Antibody Treatment Failure in Urothelial Bladder Cancer (UBC)

The example presents the case of a 64 y/o female patient diagnosed with UBC in February 2013. The patient had received 3 cycles of neoadjuvant treatment with gemcitabine and cisplatine; subsequent curative cystectomy and lymph node removal; adjuvant radiotherapy of the bladder (total cumulative dose: 45 Gy): 6 cycles of methotrexate as first line treatment for metastatic disease (best RECIST response: unknown); and 25 cycles of an anti-PD-L1 antibody (not further specified) as a second line treatment for metastatic disease under which the patient experienced a complete response (CR according to RECIST 1.1) but ultimately developed progressive disease.

Figure 2:
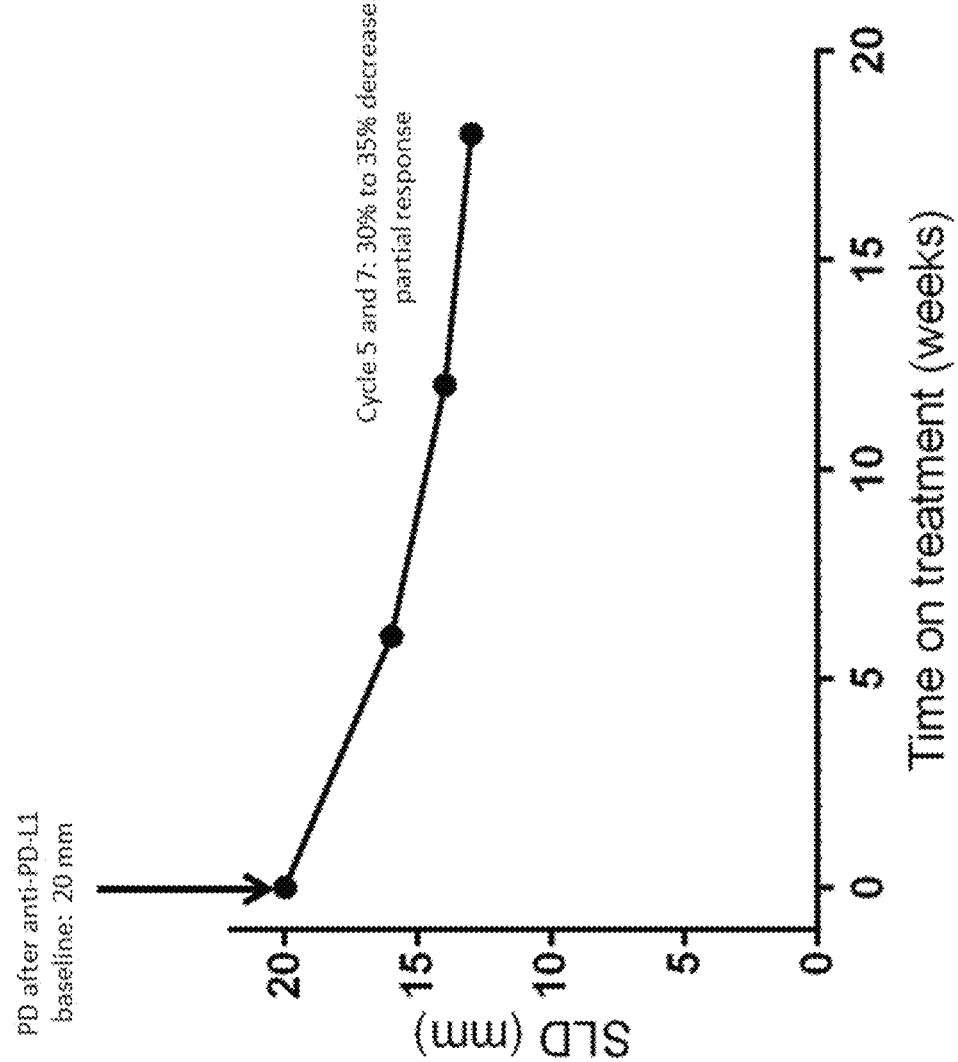
FIG. 2: Emactuzumab in combination with atezolizumab after treatment failure with an anti-PD-L1 antibody (not further specified): Readout according to RECIST 1.1. criteria. Sum of the longest diameters (SLD) are shown A partial response could be determined in a urinary bladder cancer patient previously progressive on anti-PD-L1 monotherapy (not further specified).

The patient then entered clinical study BP29428 and received combination treatment of anti-CSF1R antibody emactuzumab (1000 mg) and atezolizumab (1200 mg) every 3 weeks. Under this regimen the patient showed initially a stable disease (SD) which further improved to a PR during subsequent tumor assessments. As of today the patient is still ongoing on Study BP29428. Results are shown in FIG. 2.

Figure 4:
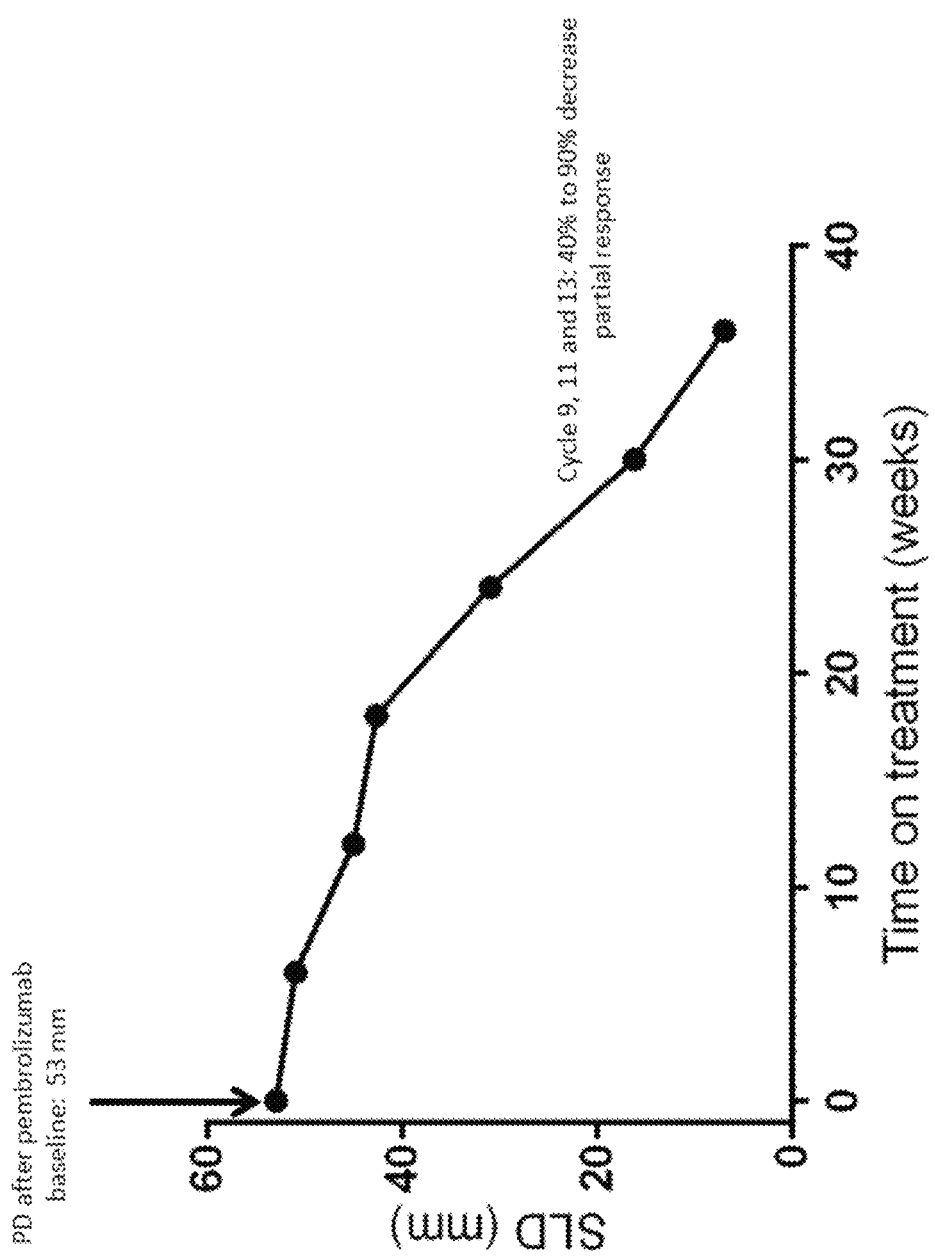
FIG. 4: Emactuzumab in combination with atezolizumab after treatment failure with pembrolizumab monotherapy: Readout according to RECIST 1.1. criteria. Sum of the longest diameters (SLD) are shown. A partial response could be determined in a non-small cell lung cancer patient previously progressive on pembrolizumab monotherapy.

The patient then entered clinical study BP29428 and received combination treatment of anti-CSF1R antibody emactuzumab (1000 mg) and atezolizumab (1200 mg) every 3 weeks. Under this regimen the patient showed initially a SD which further improved to a PR during subsequent tumor assessments. As of today the patient is still ongoing on Study BP29428. Results are shown in FIG. 4.

Example 2: Combination of Anti-CSF-1R Antibody and Anti-PD-L1 Antibody after Anti-PD-L1 Antibody Treatment Failure in Melanoma Analogously as described in Examples 1 to 4, patients suffering from a melanoma which show progression (progressive disease PD according to RECIST 1.1) under anti-PD-L1 treatment (atezolizumab (1200 mg every 3 weeks)), receive a combination treatment of anti-CSF1R antibody emactuzumab (1000 mg) and atezolizumab (1200 mg) every 3 weeks. Responses are determined as described in Examples 1.

Example 3: Combination of Anti-CSF-1R Antibody and Anti-PD-L1 Antibody after Anti-PD-L1 Antibody Treatment Failure in Urinary Bladder Cancer (UBC), Lung Cancer or Melanoma Analogously as described in Examples 1 to 4, patients suffering from urinary bladder cancer (UBC), lung cancer or melanoma which show progression (progressive disease PD according to RECIST 1.1) under anti-PD-L1 treatment (durvalumab or avelumab), receive a combination treatment of anti-CSF1R antibody emactuzumab (1000 mg) and atezolizumab (1200 mg) every 3 weeks. Responses are determined as described in Examples 1 to 2.

Example 4: Combination of Anti-CSF-1R Antibody and Anti-PD-L1 Antibody after Anti-PD1 Antibody Treatment Failure in Urinary Bladder Cancer (UBC), Lung Cancer or Melanoma Analogously as described in Examples 1 to 4, patients suffering from urinary bladder cancer (UBC), lung cancer or melanoma which show progression (progressive disease PD according to RECIST 1.1) under anti-PD1 treatment (pembrolizumab or nivolumab), receive a combination treatment of anti-CSF1R antibody emactuzumab (1000 mg) and atezolizumab (1200 mg) every 3 weeks. Responses are determined as described in Examples 1 to 3.

Example 4.1: Combination of Anti-CSF-1R Antibody and Anti-PDL1 Antibody after Anti-PD1 Antibody Treatment Failure in Non-Small Cell Lung Cancer (NSCLC)

The example presents the case of a 62 y/o male patient diagnosed with NSCLC in January 2016. The patient had received 6 cycles of cisplatine or carboplatine together with gemcitabine as first line treatment for metastatic disease (best RECIST response: PR): and 12 cycles of nivolumab as a second line treatment for metastatic disease under which the patient experienced a SD but ultimately developed progressive disease.

Figure 3:
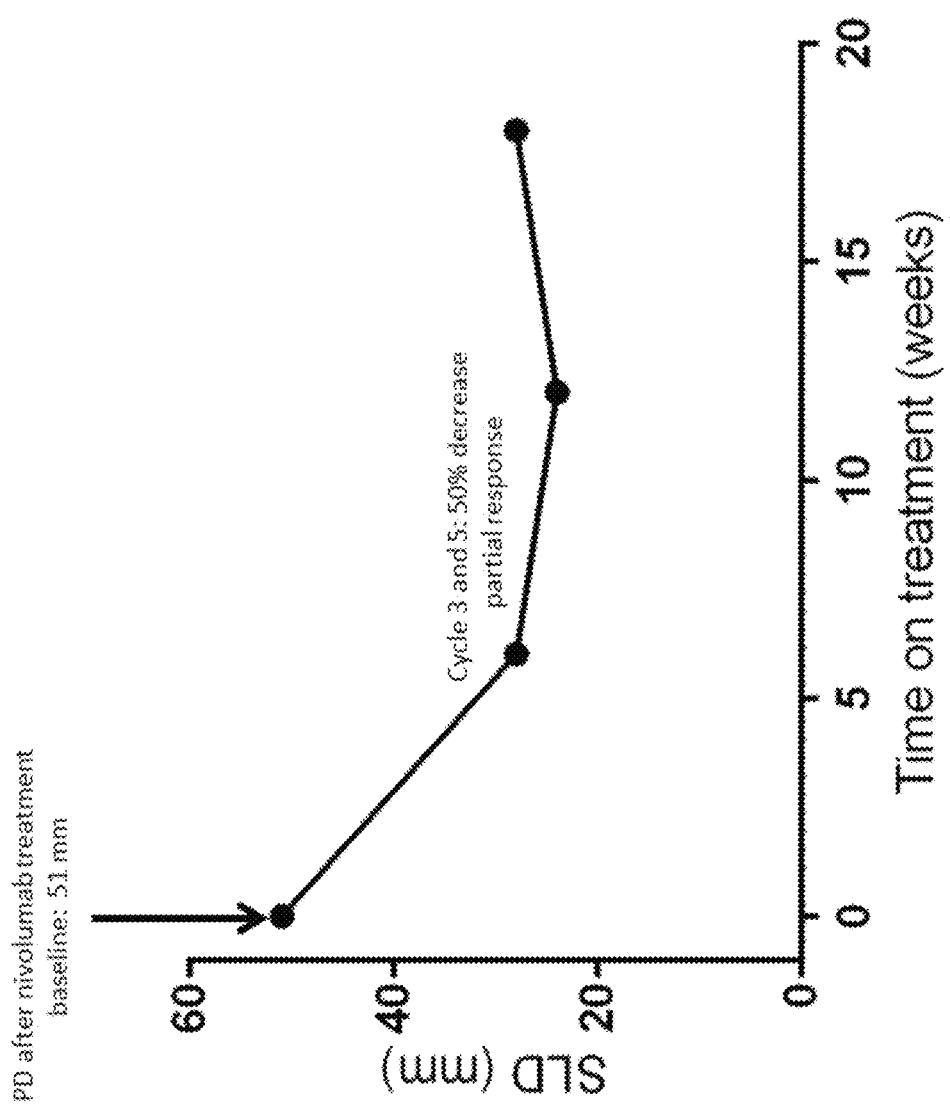
FIG. 3: Emactuzumab in combination with atezolizumab after treatment failure with nivolumab monotherapy: Readout according to RECIST 1.1. criteria. Sum of the longest diameters (SLD) are shown A partial response could be determined in a non-small cell lung cancer patient previously progressive on nivolumab monotherapy.

The patient then entered clinical study BP29428 and received combination treatment of anti-CSF1R antibody emactuzumab (1000 mg) and atezolizumab (1200 mg) every 3 weeks. Under this regimen the patient showed a PR. Results are shown in FIG. 3.

Example 4.2: Combination of Anti-CSF-1R Antibody and Anti-PDL1 Antibody after Anti-PD1 Antibody Treatment Failure in Non-Small Cell Lung Cancer (NSCLC)

The example presents the case of a 62 y/o female patient diagnosed with NSCLC in June 2014. Initially, the patient received radiotherapy of the brain and lung. The patient then received 16 cycles of carboplatine and pemetrexed and another 14 cycles of pemetrexed only as first line treatment for metastatic disease (best RECIST response: SD); and 12 cycles of pembrolizumab as a second line treatment for metastatic disease under which the patient experienced a SD but ultimately developed progressive disease. The patient also received palliative radiosurgery for brain metastases.

Example 5: Combination of Anti-CSF-1R Antibody and Anti-PD-L1 Antibody after Anti-PD-L1 Antibody Treatment Failure in Renal Cell Carcinoma (RCC), Head and Neck Squamous Cell Carcinoma (HNSCC), or Lymphomas (e.g. B-Cell Diffuse Large Cell Lymphoma (DLCL))

Analogously as described in Examples 1 to 4, patients suffering from renal cell carcinoma (RCC), head and neck squamous cell carcinoma (HNSCC), or lymphomas (e.g. B-cell diffuse large cell lymphoma (DLCL) which show progression under anti-PD-L1 treatment (atezolizumab or durvalumab or avelumab), receive a combination treatment of anti-CSF1R antibody emactuzumab (1000 mg) and atezolizumab (1200 mg) every 3 weeks. Responses are determined as described in Examples 1 to 4.

Example 6: Combination of Anti-CSF-1R Antibody and Anti-PD-L1 Antibody after Anti-PD1 Antibody Treatment Failure in Renal Cell Carcinoma (RCC), Head and Neck Squamous Cell Carcinoma (HNSCC), or Lymphomas (e.g. B-Cell Diffuse Large Cell Lymphoma (DLCL))

Analogously as described in Examples 1 to 4, patients suffering from renal cell carcinoma (RCC), head and neck squamous cell carcinoma (HNSCC), or lymphomas (e.g. B-cell diffuse large cell lymphoma (DLCL) which show progression under anti-PD1 treatment (pembrolizumab or nivolumab), receive a combination treatment of anti-CSF1R antibody emactuzumab (1000 mg) and atezolizumab (1200 mg) every 3 weeks. Responses are determined as described in Examples 1 to 5.

The invention claimed is:

1. A method of treating cancer comprising administering to a human patient suffering from cancer a therapeutically effective amount of an anti-colony stimulating factor 1 receptor (CSF-1R) antibody in combination with a therapeutically effective amount of an anti-programmed death ligand 1 (PD-L1) antibody; wherein
   the cancer is urinary bladder cancer (UCB) or non-small cell lung (NSCL) cancer, and comprises tumor cells and infiltrating CSF-1R-expressing M2-like tumor-associated macrophages;
   the patient was previously treated with a programmed death ligand 1/programmed cell death protein 1 (PD-L1/PD11 inhibitor selected from the group consisting of atezolizumab, pembrolizumab, and nivolumab;
   the prior treatment of the patient with the PD-L1/PD1 inhibitor failed according to response evaluation criteria in solid tumors (RECIST) 1.1 criteria;
   both the anti-CSF-1R antibody and the anti-PD-L1 antibody are monoclonal antibodies that comprise a constant region capable of activating antibody-dependent cell-mediated cytotoxicity;
   the anti-CSF-1R antibody comprises a heavy chain variable domain VH of SEQ ID NO:1 and a light chain variable domain VL of SEQ ID NO:2; and
   the anti-PD-L1 antibody comprises a heavy chain variable domain VH of SEQ ID NO:3 and a light chain variable domain VL of SEQ ID NO:4.

2. The method of claim 1, wherein in the anti-CSF-1R antibody is emactuzumab and the anti-PD-L1 antibody is atezolizumab.

3. The method of claim 1, wherein the PD-L1/PD1 inhibitor used in the prior treatment of the patient is atezolizumab.

4. The method of claim 1, wherein the PD-L1/PD1 inhibitor used in the prior treatment of the patient is pembrolizumab.

5. The method of claim 1, wherein the PD-L1/PD1 inhibitor used in the prior treatment of the patient is nivolumab.

6. The method of claim 1, wherein the anti-PD-L1 antibody is administered at a dose of 1100-1300 mg.

7. The method of claim 1, wherein the anti-CSF-1R antibody is administered at a dose of 900-1100 mg.

8. The method of claim 1, wherein the combination treatment results in a complete response or a partial response according to response evaluation criteria in solid tumors (RECIST) 1.1 criteria.

9. The method of claim 1, wherein the combination treatment results in at least stable disease according to response evaluation criteria in solid tumors (RECIST) 1.1 criteria.

10. The method of claim 1, wherein the cancer is urinary bladder cancer (UCB).

11. The method of claim 1, wherein the cancer is non-small cell lung (NSCL) cancer.

12. The method of claim 1, wherein the anti-CSF-1R antibody and the anti-PD-L1 antibody are monoclonal antibodies of the human IgG1 isotype.

* * * * *